United States Patent
Zhu et al.

(10) Patent No.: US 6,545,055 B1
(45) Date of Patent: Apr. 8, 2003

(54) INHIBITORS OF FACTOR XA

(75) Inventors: Bing-Yan Zhu, Belmont, CA (US); Ting Su, Belmont, CA (US); Zhaozhong Jon Jia, South San Francisco, CA (US); Robert M. Scarborough, Half Moon Bay, CA (US); Yonghong Song, Foster City, CA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/576,638

(22) Filed: May 24, 2000

Related U.S. Application Data

(60) Provisional application No. 60/135,820, filed on May 24, 1999.

(51) Int. Cl.$^7$ .................. A61K 31/18; A61K 31/155; A61K 31/16; C07C 303/00; C07C 233/00
(52) U.S. Cl. .................. 514/613; 514/602; 514/617; 514/631; 514/637; 514/638; 564/84; 564/123; 564/161
(58) Field of Search ............... 514/602, 613, 514/617, 631, 637, 638; 564/84, 123, 161

(56) References Cited

U.S. PATENT DOCUMENTS

| | | | |
|---|---|---|---|
| 4,070,176 A | 1/1978 | Oshio et al. .................. | 21/103 |
| 5,886,191 A | 3/1999 | Dominguez et al. ........ | 598/491 |

FOREIGN PATENT DOCUMENTS

| | | | |
|---|---|---|---|
| EP | 0 976 722 A1 | | 2/2000 |
| EP | 1 020 434 A1 | | 7/2000 |
| WO | 98/31661 | | 7/1998 |
| WO | 9831661 | * | 7/1998 |
| WO | 9847876 | * | 10/1998 |
| WO | 99/11657 | | 3/1999 |
| WO | 99/11658 | | 3/1999 |
| WO | 99/12903 | | 3/1999 |
| WO | 99/10316 | | 4/1999 |

OTHER PUBLICATIONS

U.S. patent application Ser. No. 60/135,820, Zhu et al., filed May 1999.*
U.S. patent application Ser. No. 60/135,845, Zhu et al., filed May 1999.*
U.S. patent application Ser. No. 60/135,849, Zhu et al., filed May 1999.*
U.S. patent application Ser. No. 09/577,131 Zhu et al., filed May 2000.*
R. Karaman, et al., "A Novel N–Dealkylation Reaction of N,N–Dialkylarylcarboxamides Promoted by Electron Transfer from Alkali Metals," Tetrahedron Letters, vol. 31, No. 7, pp. 941–944, (1990).
P. O. Burke, et al., "Basicity of Nitrogen–Sulphur ($_{v1}$) Compounds. Part 6.$^1$ Ionization of NN–Di–and N–Mono-substituted Sulphamides and Dihydro–2,1,3–benzothiadia-zoline and Benzothiadiazine 2,2–Dioxides (Cyclic Sulpha-mides)", J. Chem. Soc. Perkin Trans. II, pp. 1851–1854 (1984).
STN, Caplus accession No. 1984: 165506, XP002166636 abstract; RN 6876–65–9 & JP 58 205795 A (Fuji Photo Film Co., Ltd.).
STN, Caplus accession No. 1989–511018, XP002166637 abstract; RN 13143–43–6 & JP 63 316703 A (Hokko Chemi-cal Industry Co., Ltd.).

* cited by examiner

Primary Examiner—Richard L. Raymond
Assistant Examiner—Sudhaker B. Patel
(74) Attorney, Agent, or Firm—Townsend and Townsend and Crew LLP

(57) ABSTRACT

Novel compounds, their salts and compositions related thereto having activity against mammalian factor Xa are disclosed. The compounds are useful in vitro or in vivo for preventing or treating coagulation disorders.

6 Claims, No Drawings

INHIBITORS OF FACTOR XA

RELATED APPLICATIONS

This application claims benefit of priority under 35 USC §119(e) to U.S. Provisional Application No. 60/135,820 filed on May 24, 1999, which is herein incorporated in its entirety by reference.

FIELD OF THE INVENTION

This invention relates to novel compounds which are potent and highly selective inhibitors of isolated factor Xa or when assembled in the prothrombinase complex. These compounds show selectivity for factor Xa versus other proteases of the coagulation (e.g. thrombin, fVIIa, fIXa) or the fibrinolytic cascades (e.g. plasminogen activators, plasmin). In another aspect, the present invention relates to novel monoamidino-containing compounds, their pharmaceutically acceptable salts, and pharmaceutically acceptable compositions thereof which are useful as potent and specific inhibitors of blood coagulation in mammals. In yet another aspect, the invention relates to methods for using these inhibitors as therapeutic agents for disease states in mammals characterized by coagulation disorders.

BACKGROUND OF THE INVENTION

Hemostasis, the control of bleeding, occurs by surgical means, or by the physiological properties of vasoconstriction and coagulation. This invention is particularly concerned with blood coagulation and ways in which it assists in maintaining the integrity of mammalian circulation after injury, inflammation, disease, congenital defect, dysfumction or other disruption. Although platelets and blood coagulation are both involved in thrombus formation, certain components of the coagulation cascade are primarily responsible for the amplification or acceleration of the processes involved in platelet aggregation and fibrin deposition.

Thrombin is a key enzyme in the coagulation cascade as well as in hemostasis. Thrombin plays a central role in thrombosis through its ability to catalyze the conversion of fibrinogen into fibrin and through its potent platelet activation activity. Direct or indirect inhibition of thrombin activity has been the focus of a variety of recent anticoagulant strategies as reviewed by Claeson, G., "Synthetic Peptides and Peptidomimetics as Substrates and Inhibitors of Thrombin and Other Proteases in the Blood Coagulation System", Blood Coag. Fibrinol. 5, 411–436 (1994). Several classes of anticoagulants currently used in the clinic directly or indirectly affect thrombin (i.e. heparins, low-molecular weight heparins, heparin-like compounds and coumarins).

A prothrombinase complex, including Factor Xa (a serine protease, the activated form of its Factor X precursor and a member of the calcium ion binding, gamma carboxy-glutamyl (Gla)-containing, vitamin K dependent, blood coagulation glycoprotein family), converts the zymogen prothrombin into the active procoagulant thrombin. Unlike thrombin, which acts on a variety of protein substrates as well as at a specific receptor, factor Xa appears to have a single physiologic substrate, namely prothrombin. Since one molecule of factor Xa may be able to generate up to 138 molecules of thrombin (Elodi et al., *Thromb. Res.* 15, 617–619 (1979)), direct inhibition of factor Xa as a way of indirectly inhibiting the formation of thrombin may be an efficient anticoagulant strategy. Therefore, it has been suggested that compounds which selectively inhibit factor Xa may be useful as in vitro diagnostic agents, or for therapeutic administration in certain thrombotic disorders, see e.g., WO 94/13693.

Polypeptides derived from hematophagous organisms have been reported which are highly potent and specific inhibitors of factor Xa. U.S. Pat. No. 4,588,587 describes anticoagulant activity in the saliva of the Mexican leech, *Haementeria officinalis*. A principal component of this saliva was shown to be the polypeptide factor Xa inhibitor, antistasin (ATS), by Nutt, E. et al., "The Amino Acid Sequence of Antistasin, a Potent Inhibitor of Factor Xa Reveals a Repeated Internal Structure", J. Biol. Chem., 20, 10162–10167 (1988). Another potent and highly specific inhibitor of Factor Xa, called tick anticoagulant peptide (TAP), has been isolated from the whole body extract of the soft tick *Ornithidoros moubata*, as reported by Waxman, L., et al., "Tick Anticoagulant Peptide (TAP) is a Novel Inhibitor of Blood Coagulation Factor Xa" Science, 248, 593–596 (1990).

Factor Xa inhibitory compounds which are not large polypeptide-type inhibitors have also been reported including: Tidwell, R. R. et al., "Strategies for Anticoagulation With Synthetic Protease Inhibitors. Xa Inhibitors Versus Thrombin Inhibitors", Thromb. Res., 19, 339–349 (1980); Turner, A. D. et al., "p-Amidino Esters as Irreversible Inhibitors of Factor IXa and Xa and Thrombin", Biochemistry, 25, 4929–4935 (1986); Hitomi, Y. et al., "Inhibitory Effect of New Synthetic Protease Inhibitor (FUT-175) on the Coagulation System", Haemostasis, 15, 164–168 (1985); Sturzebecher, J. et al., "Synthetic Inhibitors of Bovine Factor Xa and Thrombin. Comparison of Their Anticoagulant Efficiency", Thromb. Res., 54, 245–252 (1989); Kam, C. M. et al., "Mechanism Based Isocoumarin Inhibitors for Trypsin and Blood Coagulation Serine Proteases: New Anticoagulants", Biochemistry, 27, 2547–2557 (1988); Hauptmann, J. et al., "Comparison of the Anticoagulant and Antithrombotic Effects of Synthetic Thrombin and Factor Xa Inhibitors", Thromb. Haemost., 63, 220–223 (1990); and the like.

Others have reported Factor Xa inhibitors which are small molecule organic compounds, such as nitrogen containing heterocyclic compounds which have amidino substituent groups, wherein two functional groups of the compounds can bind to Factor Xa at two of its active sites. For example, WO 98/28269 describes pyrazole compounds having a terminal C(=NH)—NH$_2$ group; WO 97/21437 describes benzimidazole compounds substituted by a basic radical which are connected to a naththyl group via a straight or branched chain alkylene,—C(=O) or —S(=O)$_2$ bridging group; WO 99/10316 describes compounds having a 4-phenyl-N-alkylamidino-piperidine and 4-phenoxy-N-alkylamidino-piperidine group connected to a 3-amidinophenyl group via a carboxamidealkyleneamino bridge; and EP 798295 describes compounds having a 4-phenoxy-N-alkylamidino-piperidine group connected to an amidinonaphthyl group via a substituted or unsubstituted sulfonamide or carboxamide bridging group.

There exists a need for effective therapeutic agents for the regulation of hemostasis, and for the prevention and treatment of thrombus formation and other pathological processes in the vasculature induced by thrombin such as restenosis and inflammation. In particular, there continues to be a need for compounds which selectively inhibit factor Xa or its precursors. Compounds that have different combinations of bridging groups and functional groups than compounds previously discovered are needed, particularly compounds which selectively or preferentially bind to Factor Xa. Compounds with a higher degree of binding to Factor Xa than to thrombin are desired, especially those compounds having good bioavailability and/or solubility.

SUMMARY OF THE INVENTION

The present invention relates to novel compounds which inhibit factor Xa, their pharmaceutically acceptable isomers, salts, hydrates, solvates and prodrug derivatives, and pharmaceutically acceptable compositions thereof which have particular biological properties and are useful as potent and specific inhibitors of blood coagulation in mammals. In another aspect, the invention relates to methods of using these inhibitors as diagnostic reagents or as therapeutic agents for disease states in mammals which have coagulation disorders, such as in the treatment or prevention of any thrombotically mediated acute coronary or cerebrovascular syndrome, any thrombotic syndrome occurring in the venous system, any coagulopathy, and any thrombotic complications associated with extracorporeal circulation or instrumentation, and for the inhibition of coagulation in biological samples.

In certain embodiments, this invention relates to novel compounds which are potent and highly selective inhibitors of isolated factor Xa when assembled in the prothrombinase complex. These compounds show selectivity for factor Xa versus other proteases of the coagulation cascade (e.g. thrombin, etc.) or the fibrinolytic cascade, and are useful as diagnostic reagents as well as antithrombotic agents.

In a preferred embodiment, the present invention provides a compound of the formula I:

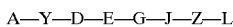

A—Y—D—E—G—J—Z—L wherein:
A is selected from:
  (a) $C_1$–$C_6$-alkyl;
  (b) $C_3$–$C_8$-cycloalkyl;
  (c) phenyl, which is independently substituted with 0–2 $R^1$ substituents;
  (d) naphthyl, which is independently substituted with 0–2 $R^1$ substituents; and
  (e) a monocyclic or fused bicyclic heterocyclic ring system having from 5 to 10 ring atoms, wherein 1–4 ring atoms of the ring system are selected from N, O and S, and wherein the ring system may be substituted from 0–2 $R^1$ substituents;

$R^1$ is selected from:
  Halo, $C_{1-4}$alkyl, $C_{2-6}$alkenyl, $C_{2-6}$alkynyl, $C_{3-8}$cycloalkyl, $C_{0-4}$alkyl$C_{3-8}$-cycloalkyl, —CN, —$NO_2$, $(CH_2)_m NR^2 R^3$, $SO_2 NR^2 R^3$, $SO_2 R^2$, $CF_3$, $OR^2$, and a 5–6 membered aromatic heterocyclic system containing from 1–4 heteroatoms selected from N, O and S, wherein from 1–4 hydrogen atoms on the aromatic heterocyclic system may be independently replaced with a member selected from the group consisting of halo, $C_1$–$C_4$-alkyl, —CN $C_{1-4}$alkyl, $C_{2-6}$alkenyl, $C_{2-6}$alkynyl, $C_{1-8}$cycloalkyl, $C_{1-4}$alkyl$C_{3-8}$cycloalkyl and —$NO_2$;

$R^2$ and $R^3$ are independently selected from the group consisting of:
  H, $C_{1-4}$alkyl, $C_{2-6}$alkenyl, $C_{2-4}$alkynyl, $C_{3-8}$cycloalkyl, $C_{0-4}$alkyl$C_{3-8}$cycloalkyl, $C_{0-4}$alkylphenyl and $C_{0-4}$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-4}$alkenyl, $C_{2-6}$alkynyl, $C_{3-8}$cycloalkyl, $C_{0-4}$alkyl$C_{3-8}$cycloalkyl, —CN, and —$NO_2$;

m is an integer of 0–2;
Y is a member selected from the group consisting of:
  a direct link, —C(=O)—, —N($R^4$)—, —C(=O)—N($R^4$)—, —N($R^4$)—C(=O)—, —$SO_2$—, —O—, —$SO_2$—N($R^4$)— and —N($R^4$)—$SO_2$—;

$R^4$ is selected from:
  H, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, $C_{0-4}$alkylphenyl and $C_0$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN, and —$NO_2$;

D is a direct link or is a member selected from the group consisting of:
  (a) phenyl, which is independently substituted with 0–2 $R^{1a}$ substituents;
  (b) naphthyl, which is independently substituted with 0–2 $R^{1a}$ substituents; and
  (c) a monocyclic or fused bicyclic heterocyclic ring system having from 5 to 10 ring atoms, wherein 1–4 ring atoms of the ring system are selected from N, O and S, and wherein the ring system may be substituted from 0–2 $R^{1a}$ substituents;

$R^{1a}$ is selected from:
  Halo, $C_{1-4}$alkyl, $C_{2-6}$alkenyl, $C_{2-6}$alkynyl, $C_{3-8}$cycloalkyl, $C_{0-4}$alkyl$C_{3-8}$-cycloalkyl, —CN, —$NO_2$, $(CH_2)_m NR^{2a} R^{3a}$, $SO_2 NR^{2a} R^{3a}$, $SO_2 R^{2a}$, $CF_3$, $OR^{2a}$, and a 5–6 membered aromatic heterocyclic system containing from 1–4 heteroatoms selected from N, O and S, wherein from 1–4 hydrogen atoms on the aromatic heterocyclic system may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN and —$NO_2$;

$R^{2a}$ and $R^{3a}$ are independently selected from the group consisting of:
  H, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, $C_{0-4}$alkylphenyl and $C_{1-4}$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN and —$NO_2$;

E is a member selected from the group consisting of:
  —N($R^5$)—C(=O)—, —C(=O)—N($R^5$)—, —N($R^5$)—C(=O)—N($R^6$)—, —$SO_2$—N($R^5$)—, —N($R^5$)—$SO_2$—N($R^6$)— and —N($R^5$)—$SO_2$—N($R^6$)—C(=O)—;

$R^5$ and $R^6$ are independently selected from:
  H, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, $C_{0-4}$alkylphenyl, $C_{1-4}$alkylnaphthyl, $C_{0-4}$alkylheteroaryl, $C_{1-4}$alkylCOOH and $C_{1-4}$alkylCOO$C_{1-4}$alkyl, wherein from 1–4 hydrogen atoms on the ring atoms of the phenyl, naphthyl and heteroaryl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN and —$NO_2$;

G is selected from:
  —$CR^7 R^8$— and $CR^{7a} R^{8a}$—$CR^{7b} R^{8b}$— wherein $R^7$, $R^8$, $R^{7a}$, $R^{8a}$, $R^{7a}$ and $R^{8b}$ are independently a member selected from from the group consisting of: hydrogen, $C_{1-4}$alkyl, $C_{2-6}$alkenyl, $C_{2-6}$alkynyl, $C_{3-8}$cycloalkyl, $C_{1-4}$alkyl-$C_{3-8}$cycloalkyl, $C_{0-4}$alkylphenyl, $C_{0-4}$alkylnaphthyl
—$C_{0-4}$alkylCOOR$^9$, —$C_{0-4}$alkylC(=O)NR$^9$R$^{10}$,
—$C_0$alkylC(=O)NR$^9$—CH$_2$—CH$_2$—O—R$^{10}$,
—$C_{0-4}$alkylC(=O)NR$^9$(—CH$_2$—CH$_2$—O—
R$^{10}$—)$_2$, —N(R$^9$)COR$^{10}$, —N(R$^9$)C(=O)R$^{10}$,
—N(R$^9$)SO$_2$R$^{10}$, and a naturally occurring or synthetic amino acid side chain, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl-$C_{3-8}$cycloalkyl, —CN and —NO$_2$;

R$^9$ and R$^{10}$ are independently selected from:
H, $C_{1-4}$alkyl, $C_{0-4}$alkylphenyl and $C_{0-4}$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl-$C_{3-8}$cycloalkyl, —CN and —NO$_2$, and wherein R$^9$ and R$^{10}$ taken together can form a 5–8 membered heterocylic ring;

J is a member selected from the group consisting of:
a direct link, —C(=O)—N(R$^{11}$)—(CH$_2$)$_{0-2}$, —N(R$^{11}$)—(CH$_2$)$_{0-2}$—C(=O)—, and —N(R$^{11}$)—(CH$_2$)$_{0-2}$;

R$^{11}$ is a member selected from the group consisting of:
hydrogen, $C_{1-4}$alkyl, $C_{2-6}$alkenyl, $C_{2-6}$alkynyl, $C_{3-8}$cycloalkyl, $C_{0-4}$alkyl-$C_{3-8}$cycloalkyl, $C_{0-4}$alkylphenyl, $C_{0-4}$alkylnaphthyl, $C_{0-4}$alkylheterocyclic ring having from 1 to 4 hetero ring atoms selected from the group consisting of N, O and S, CH$_2$COOC$_{1-4}$alkyl, CH$_2$COOC$_{1-4}$alkylphenyl and CH$_2$COOC$_{1-4}$alkylnaphthyl;

Z is a member selected from the group consisting of:
(a) phenyl, which is independently substituted with 0–2 R$^{1b}$ substituents;
(b) naphthyl, which is independently substituted with 0–2 R$^{1b}$ substituents; and
(c) a monocyclic or fused bicyclic heterocyclic ring system having from 5 to 10 ring atoms, wherein 1–4 ring atoms of the ring system are selected from N, O and S, and wherein the ring system may be subsituted from 0–2 R$^{1b}$ substituents;

R$^{1b}$ is selected from:
Halo, $C_{1-4}$alkyl, $C_{2-6}$alkenyl, $C_{2-6}$alkynyl, $C_{3-8}$cycloalkyl, $C_{0-4}$alkylC$_{3-8}$cycloalkyl, —CN, —NO$_2$, NR$^{2b}$R$^{3b}$, SO$_2$NR$^{2b}$R$^{3b}$, SO$_2$R$^{2b}$, CF$_3$, OR$^{2b}$, O—CH$_2$-Ph, O—CH$_2$—OPh, O—CH$_2$—CH$_2$—OR$^{2b}$, O—CH$_2$COOR$^{2b}$, N(R$^2$b)—CH$_2$—CH$_2$—OR$^{2b}$, N(—CH$_2$—CH$_2$—OR$^2$)$_2$, N(R$^{2b}$)—C(=O)R$^{3b}$, N(R$^{2b}$)—SO$_2$R$^{3b}$, and a 5–6 membered aromatic heterocyclic system containing from 1–4 heteroatoms selected from N, O and S, wherein from 1–4 hydrogen atoms on the aromatic heterocyclic system may be independently replaced with a member selected from the group consisting of halo, $C_{1-4}$alkyl, $C_{2-6}$alkenyl, $C_{2-4}$alkynyl, $C_{3-8}$cycloalkyl, $C_{0-4}$alkylC$_{3-8}$cycloalkyl, —CN and —NO$_2$;

R$^{2b}$ and R$^{3b}$ are independently selected from the group consisting of:
H, $C_{1-4}$alkyl, $C_{2-6}$alkenyl, $C_{2-6}$alkynyl, $C_{3-8}$cycloalkyl, $C_{0-4}$alkylC$_{3-8}$cycloalkyl, $C_{1-4}$alkylphenyl and $C_{0-4}$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{1-4}$alkylC$_{3-8}$cycloalkyl, —CN and —NO$_2$;

L is selected from:
H, —CN, C(=O)NR$^{12}$R$^{13}$, (CH$_2$)$_n$NR$^{12}$R$^{13}$, C(=NR$^{12}$)NR$^{12}$R$^{13}$, OR$^{12}$, NR$^{12}$R$^{13}$, —NR$^{12}$C(=NR$^{12}$)NR$^{12}$R$^{13}$, and NR$^{12}$C(=NR$^{12}$)—R$^{13}$;

R$^{12}$ and R$^{13}$ are independently selected from:
hydrogen, —OR$^{14}$, —NR$^{14}$R$^{15}$, $C_{1-4}$alkyl, $C_{0-4}$alkylphenyl, $C_{0-4}$alkylnaphthyl, COOC$_{1-4}$alkyl, COO—$C_{0-4}$alkylphenyl and COO—$C_{0-4}$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkylC$_{3-8}$cycloalkyl, —CN, and —NO$_2$;

R$^{14}$ and R$^{15}$ are independently selected from:
H, $C_{1-4}$alkyl, $C_{2-6}$alkenyl, $C_{2-6}$alkynyl, $C_{3-8}$cycloalkyl, $C_{0-4}$alkylC$_{3-8}$cycloalkyl, $C_{0-4}$alkylphenyl and $C_{0-4}$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{1-4}$alkylC$_{3-8}$cycloalkyl, —CN, and —NO$_2$;

and all pharmaceutically acceptable isomers, salts, hydrates, solvates and prodrug derivatives thereof.

In certain aspects of this invention, compounds are provided which are useful as diagnostic reagents. In another aspect, the present invention includes pharmaceutical compositions comprising a pharmaceutically effective amount of the compounds of this invention and a pharmaceutically acceptable carrier. In yet another aspect, the present invention includes methods comprising using the above compounds and pharmaceutical compositions for preventing or treating disease states characterized by undesired thrombosis or disorders of the blood coagulation process in mammals, or for preventing coagulation in biological samples such as, for example, stored blood products and samples. Optionally, the methods of this invention comprise administering the pharmaceutical composition in combination with an additional therapeutic agent such as an antithrombotic and/or a thrombolytic agent and/or an anticoagulant.

The preferred compounds also include their pharmaceutically acceptable isomers, hydrates, solvates, salts and prodrug derivatives.

DETAILED DESCRIPTION OF THE INVENTION

Definitions

In accordance with the present invention and as used herein, the following terms are defined with the following meanings, unless explicitly stated otherwise.

The term "alkenyl" refers to a trivalent straight chain or branched chain unsaturated aliphatic radical. The term "alkinyl" (or "alkynyl") refers to a straight or branched chain aliphatic radical that includes at least two carbons joined by a triple bond. If no number of carbons is specified alkenyl and alkinyl each refer to radicals having from 2–12 carbon atoms.

The term "alkyl" refers to saturated aliphatic groups including straight-chain, branched-chain and cyclic groups having the number of carbon atoms specified, or if no number is specified, having up to 12 carbon atoms. The term "cycloalkyl" as used herein refers to a mono-, bi-, or tricyclic aliphatic ring having 3 to 14 carbon atoms and preferably 3 to 7 carbon atoms.

As used herein, the terms "carbocyclic ring structure" and "$C_{3-16}$carbocyclic mono, bicyclic or tricyclic ring structure" or the like are each intended to mean stable ring structures having only carbon atoms as ring atoms wherein the ring structure is a substituted or unsubstituted member selected from the group consisting of: a stable monocyclic ring which is aromatic ring ("aryl") having six ring atoms; a stable monocyclic non-aromatic ring having from 3 to 7 ring atoms in the ring; a stable bicyclic ring structure having a total of from 7 to 12 ring atoms in the two rings wherein the bicyclic ring structure is selected from the group consisting of ring structures in which both of the rings are aromatic, ring structures in which one of the rings is aromatic and ring structures in which both of the rings are non-aromatic; and a stable tricyclic ring structure having a total of from 10 to 16 atoms in the three rings wherein the tricyclic ring structure is selected from the group consisting of: ring structures in which three of the rings are aromatic, ring structures in which two of the rings are aromatic and ring structures in which three of the rings are non-aromatic. In each case, the non-aromatic rings when present in the monocyclic, bicyclic or tricyclic ring structure may independently be saturated, partially saturated or fully saturated. Examples of such carbocyclic ring structures include, but are not limited to, cyclopropyl, cyclobutyl, cyclopentyl, cyclohexyl, adamantyl, cyclooctyl, [3.3.0]bicyclooctane, [4.3.0]bicyclononane, [4.4.0]bicyclodecane (decalin), 2.2.2] bicyclooctane, fluorenyl, phenyl, naphthyl, indanyl, adamantyl, or tetrahydronaphthyl (tetralin). Moreover, the ring structures described herein may be attached to one or more indicated pendant groups via any carbon atom which results in a stable structure. The term "substituted" as used in conjunction with carbocyclic ring structures means that hydrogen atoms attached to the ring carbon atoms of ring structures described herein may be substituted by one or more of the substituents indicated for that structure if such substitution(s) would result in a stable compound.

The term "aryl" which is included with the term "carbocyclic ring structure" refers to an unsubstituted or substituted aromatic ring, substituted with one, two or three substituents selected from loweralkoxy, loweralkyl, loweralkylamino, hydroxy, halogen, cyano, hydroxyl, mercapto, nitro, thioalkoxy, carboxaldehyde, carboxyl, carboalkoxy and carboxamide, including but not limited to carbocyclic aryl, heterocyclic aryl, and biaryl groups and the like, all of which may be optionally substituted. Preferred aryl groups include phenyl, halophenyl, loweralkylphenyl, napthyl, biphenyl, phenanthrenyl and naphthacenyl.

The term "arylalkyl" which is included with the term "carbocyclic aryl" refers to one, two, or three aryl groups having the number of carbon atoms designated, appended to an alkyl group having the number of carbon atoms designated. Suitable arylalkyl groups include, but are not limited to, benzyl, picolyl, naphthylmethyl, phenethyl, benzyhydryl, trityl, and the like, all of which may be optionally substituted.

As used herein, the term "heterocyclic ring" or "heterocyclic ring system" is intended to mean a substituted or unsubstituted member selected from the group consisting of stable monocyclic ring having from 5–7 members in the ring itself and having from 1 to 4 hetero ring atoms selected from the group consisting of N, O and S; a stable bicyclic ring structure having a total of from 7 to 12 atoms in the two rings wherein at least one of the two rings has from 1 to 4 hetero atoms selected from N, O and S, including bicyclic ring structures wherein any of the described stable monocyclic heterocyclic rings is fused to a hexane or benzene ring; and a stable tricyclic heterocyclic ring structure having a total of from 10 to 16 atoms in the three rings wherein at least one of the three rings has from 1 to 4 hetero atoms selected from the group consisting of N, O and S. Any nitrogen and sulfur atoms present in a heterocyclic ring of such a heterocyclic ring structure may be oxidized. Unless indicated otherwise the terms "heterocyclic ring" or "heterocyclic ring system" include aromatic rings, as well as non-aromatic rings which can be saturated, partially saturated or fully saturated non-aromatic rings. Also, unless indicated otherwise the term "heterocyclic ring system" includes ring structures wherein all of the rings contain at least one hetero atom as well as structures having less than all of the rings in the ring structure containing at least one hetero atom, for example bicyclic ring structures wherein one ring is a benzene ring and one of the rings has one or more hetero atoms are included within the term "heterocyclic ring systems" as well as bicyclic ring structures wherein each of the two rings has at least one hetero atom. Moreover, the ring structures described herein may be attached to one or more indicated pendant groups via any hetero atom or carbon atom which results in a stable structure. Further, the term "substituted" means that one or more of the hydrogen atoms on the ring carbon atom(s) or nitrogen atom(s) of the each of the rings in the ring structures described herein may be replaced by one or more of the indicated substituents if such replacement(s) would result in a stable compound. Nitrogen atoms in a ring structure may be quaternized, but such compounds are specifically indicated or are included within the term "a pharmaceutically acceptable salt" for a particular compound. When the total number of O and S atoms in a single heterocyclic ring is greater than 1, it is preferred that such atoms not be adjacent to one another. Preferably, there are no more that 1 O or S ring atoms in the same ring of a given heterocyclic ring structure.

Examples of monocylic and bicyclic heterocylic ring systems, in alphabetical order, are acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolinyl, indolizinyl, indolyl, 3H-indolyl, isobenzofuiranyl, isochromanyl, isoindazolyl, isoindolinyi, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl,. purinyl, pyranyl, pyrazinyl, pyroazolidinyl, pyrazolinyl, pyrazolyl, pyridazinyl, pryidooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuiranyl, tetrahydroisoquinolinyl, tetrahydroquinolinyl, 6H-1,2,5-thiadazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2, 3-triazolyl, 1,2,4-triazolyl, 1,2,5-triazolyl, 1,3,4-triazolyl and xanthenyl. Preferred heterocyclic ring structures include, but are not limited to, pyridinyl, furanyl, thienyl, pyrrolyl, pyrazolyl, pyrrolidinyl, imidazolyl, indolyl, benzimidazolyl, 1H-indazolyl, oxazolinyl, or isatinoyl. Also included are fused ring and spiro compounds containing, for example, the above heterocylic ring structures.

As used herein the term "aromatic heterocyclic ring system" has essentially the same definition as for the monocyclic and bicyclic ring systems except that at least one ring of the ring system is an aromatic heterocyclic ring or the bicyclic ring has an aromatic or non-aromatic heterocyclic ring fused to an aromatic carbocyclic ring structure.

The terms "halo" or "halogen" as used herein refer to Cl, Br, F or I substituents. The term "haloalkyl", and the like, refer to an aliphatic carbon radicals having at least one hydrogen atom replaced by a Cl, Br, F or I atom, including, mixtures of different halo atoms. Trihaloalkyl includes trifluoromethyl and the like as preferred radicals, for example.

The term "methylene" refers to —$CH_2$—.

The term "pharmaceutically acceptable salts" includes salts of compounds derived from the combination of a compound and an organic or inorganic acid. These compounds are useful in both free base and salt form. In practice, the use of the salt form amounts to use of the base form; both acid and base addition salts are within the scope of the present invention. "Pharmaceutically acceptable acid addition salt" refers to salts retaining the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts. Salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly preferred organic nontoxic bases are isopropylamine, diethylamine, ethanolamine, trimethamine, dicyclohexylamine, choline, and caffeine.

"Biological property" for the purposes herein means an in vivo effector or antigenic function or activity that is directly or indirectly performed by a compound of this invention that are often shown by in vitro assays. Effector ftmctions include receptor or ligand binding, any enzyme activity or enzyme modulatory activity, any carrier binding activity, any hormonal activity, any activity in promoting or inhibiting adhesion of cells to an extracellular matrix or cell surface molecules, or any structural role. Antigenic functions include possession of an epitope or antigenic site that is capable of reacting with antibodies raised against it.

In the compounds of this invention, carbon atoms bonded to four non-identical substituents are asymmetric. Accordingly, the compounds may exist as diastereoisomers, enantiomers or mixtures thereof. The syntheses described herein may employ racemates, enantiomers or diastereomers as starting materials or intermediates. Diastereomeric products resulting from such syntheses may be separated by chromatographic or crystallization methods, or by other methods known in the art. Likewise, enantiomeric product mixtures may be separated using the same techniques or by other methods known in the art. Each of the asymmetric carbon atoms, when present in the compounds of this invention, may be in one of two configurations (R or S) and both are within the scope of the present invention.

Preferred Embodiments

In a preferred embodiment, the present invention provides a compound according to the formula I:

wherein:
A is selected from:
(a) $C_1$–$C_6$-alkyl;
(b) $C_3$—$C_8$-cycloalkyl;
(c) phenyl, which is independently substituted with 0–2 $R^1$ substituents;
(d) naphthyl, which is independently substituted with 0–2 $R^1$ substituents; and
(e) a monocyclic or fused bicyclic heterocyclic ring system having from 5 to 10 ring atoms, wherein 1–4 ring atoms of the ring system are selected from N, O and S, and wherein the ring system may be substituted from 0–2 $R^1$ substituents;

$R^1$ is selected from:
halo, $C_{1-4}$alkyl, —CN, $(CH_2)_mNR^2R^3$, $SO_2NR^2R^3$, $SO_2R^2$, $CF_3$, $OR^2$, and a 5–6 membered aromatic heterocyclic system containing from 1–4 heteroatoms selected from N, O and S;

$R^2$ and $R^3$ are independently selected from the group consisting of:
H, $C_{1-4}$alkyl and $C_{0-4}$alkylaryl, m is an integer of 0–2;

Y is a member selected from the group consisting of:
a direct link, —C(=O)—, —N($R^4$)—, —C(=O)—N ($R^4$)—, —N($R^4$)—C(=O)—, —$SO_2$—, —O—, —$SO_2$—N($R^4$)— and —N($R^4$)—$SO_2$—;

$R^4$ is selected from:
H, $C_{1-4}$alkyl and $C_{0-4}$alkylaryl;.

D is absent or is a member selected from the group consisting of:
(a) aryl, which is independently substituted with 0–2 $R^{1a}$ substituents; and
(b) a monocyclic or fused bicyclic heterocyclic ring system having from 5 to 10 ring atoms, wherein 1–4 ring atoms of the ring system are selected from N, O and S, and wherein the ring system may be substituted from 0–2 $R^{1a}$ substituents;

$R^{1a}$ is selected from:
Halo, $C_{1-4}$alkyl, —CN, —$NO_2$, $(CH_2)_mNR^2R^{3a}$, $SO_2NR^{2a}R^{3a}$, $SO_2R^{2a}$, $CF_3$, $OR^{2a}$, and a 5–6 membered aromatic heterocyclic ring containing from 1–4 heteroatoms selected from N, O and S;

$R^{2a}$ and $R^{3a}$ are independently selected from the group consisting of:
  H, $C_{1-4}$alkyl and $C_{1-4}$alkylaryl;
E is a member selected from the group consisting of:
  —N($R^5$)—C(=O)—, —C(=O)—N($R^5$)—, —N($R^5$)—C(=O)—N($R^6$)—, —SO$_2$—N($R^5$)—, —N($R^5$)—SO$_2$—N($R^6$)— and —N($R^5$)—SO$_2$—N($R^6$)C(=O)—;
$R^1$ and $R^6$ are independently selected from:
  H, $C_{1-4}$alkyl, $C_{0-4}$alkylaryl, $C_{0-4}$alkylheteroaryl, $C_{1-4}$alkylCOOH and $C_{1-4}$alkylCOOC$_{1-4}$alkyl;
G is selected from:
  —C$R^7R^8$— and C$R^{7a}R^{8a}$C$R^{7b}R^{8b}$—
wherein $R^7$, $R^8$, $R^{7a}$, $R^{8a}$, $R^{7b}$ and $R^{8b}$ are independently a member selected from from the group consisting of:
  hydrogen, $C_{1-4}$alkyl, $C_{1-4}$alkyl-$C_{3-8}$cycloalkyl, $C_{0-4}$alkylaryl, —$C_{1-4}$alkylCOO$R^9$, —$C_{0-4}$alkylC(=O)N$R^9R^{10}$, —N($R^9$)CO$R^{10}$, —N($R^9$)C(=O)$R^{10}$, —N($R^9$)SO$_2R^{10}$, and common amino acid side chains;
$R^9$ and $R^{10}$ are independently selected from:
  H, $C_{1-4}$alkyl and $C_{0-4}$alkylaryl;
J is a member selected from the group consisting of:
  a direct link, —C(=O)—N($R^{11}$)—(CH$_2$)$_{0-2}$, —N($R^{11}$)—(CH$_2$)$_{0-2}$—C(=O)—, and —N($R^{11}$)—(CH$_2$)$_{0-2}$;
$R^{11}$ is a member selected from the group consisting of:
  hydrogen, $C_{1-4}$alkyl, $C_{2-6}$alkenyl, $C_{2-6}$alkynyl, $C_{3-8}$cycloalkyl, $C_{0-4}$alkylkaryl, $C_{0-4}$alkylheterocyclics, CH$_2$COOC$_{1-4}$alkyl, CH$_2$COOC$_{1-4}$alkylaryl;
Z is a member selected from the group consisting of:
  (a) aryl, which is independently substituted with 0–2 $R^{1b}$ substituents; and
  (b) a monocyclic or fused bicyclic heterocyclic ring system having from 5 to 10 ring atoms, wherein 1–4 ring atoms of the ring system are selected from N, O and S, and wherein the ring system may be subsituted from 0–2 $R^{1b}$ substituents;
$R^{1b}$ is selected from:
  halo, $C_{1-4}$alkyl, —CN, —NO$_2$, N$R^{2b}R^{3b}$, SO$_2$N$R^{2b}R^{3b}$, SO$_2$O$R^{2b}R^{3b}$, CF$_3$, O$R^{2b}$, O—CH$_2$—CH$_2$—O$R^{2b}$, O—CH$_2$COO$R^{2b}$, N($R^{2b}$)—CH$_2$—CH$_2$—O$R^{2b}$, N(—CH$_2$—CH$_2$—O$R^{2b}$)$_2$, N($R^{2b}$)C(=O)$R^{3b}$, N($R^{2b}$)—SO$_2R^{3b}$, and a 5–6 membered aromatic heterocyclic ring containing from 1–4 heteroatoms selected from N, O and S;
$R^{2b}$ and $R^{3b}$ are independently selected from the group consisting of:
  H, $C_{1-4}$alkyl and $C_{0-4}$alkylaryl;
L is selected from:
  H, —CN, C(=O)N$R^{12}R^{13}$, (CH$_2$)$_n$N$R^{12}R^{13}$, C(=N$R^{12}$)N$R^{12}R^{13}$, O$R^{12}$, —N$R^{12}$C(=N$R^{12}$)N$R^{12}R^{13}$ and N$R^{12}$C(=N$R^{12}$)—$R^{13}$;
$R^{12}$ and $R^{13}$ are independently selected from: hydrogen, —O$R^{14}$, —N$R^{14}R^{15}$, $C_{1-4}$alkyl, $C_{0-4}$alkylaryl COOC$_{1-4}$alkyl, and COO—$C_{0-4}$alkylaryl;
$R^{14}$ and $R^{15}$ are independently selected from:
  H and $C_{1-4}$alkyl; and
all pharmaceutically acceptable isomers, salts, hydrates, solvates and prodrug derivatives thereof.

In a further preferred embodiment, the present invention provides a compound according to the formula I:

A—Y—D—E—G—J—Z—L wherein:
A is selected from:
  (a) phenyl, which is independently substituted with 0–2 $R^1$ substituents; and
  (b) a monocyclic or fused bicyclic heterocyclic ring system having from 5 to 10 ring atoms, wherein 1–4 ring atoms of the ring system are selected from N, O and S, and wherein the ring system may be subsituted from 0–2 $R^1$ substituents;
$R^1$ is selected from:
  halo, (CH$_2$)$_m$N$R^2R^3$, SO$_2$N$R^2R^3$ and SO$_2R^2$;
$R^2$ and $R^3$ are independently selected from the group consisting of:
  H and $C_{1-4}$alkyl;
Y is a member selected from the group consisting of:
  a direct link, —C(=O)—, —SO$_2$— and —O—;
D is a member selected from the group consisting of:
  (a) phenyl, which is independently substituted with 0–2 $R^{1a}$ substituents; and
  (b) a monocyclic or fused bicyclic heterocyclic ring system having from 5 to 10 ring atoms, wherein 1–4 ring atoms of the ring system are selected from N, O and S, and wherein the ring system may be subsituted from 0–2 $R^{1a}$ substituents;
$R^{1a}$ is selected from:
  Halo and $C_{1-4}$alkyl;
$R^{2a}$ and $R^{3a}$ are independently selected from the group consisting of:
  H, $C_{1-4}$alkyl, $C_{0-4}$alkylaryl;
E is a member selected from the group consisting of:
  —N($R^5$)—C(=O)— and —C(=O)—N($R^5$)—;
$R^1$ and $R^6$ are independently selected from:
  H, $C_{1-4}$alkyl, $C_{1-4}$alkylaryl and $C_{0-4}$alkylheteroaryl;
G is selected from:
  —C$R^7R^8$— and —C$R^{7a}R^{8a}$—C$R^{7b}R^{8b}$—
wherein $R^7$, $R^{78}$, $R^{7a}$, $R^{8a}$, $R^{7b}$ and $R^{8b}$ are independently a member selected from from the group consisting of:
  hydrogen, $C_{1-4}$alkyl, $C_{0-4}$alkyl-$C_{3-8}$cycloalkyl, $C_{1-4}$alkylaryl, —$C_{0-4}$alkylCOO$R^9$, —$C_{0-4}$alkylC(=O)N$R^9R^{10}$, $C_{0-4}$alkylC(=O)N$R^9$—CH$_2$—CH$_2$—O—$R^{10}$, —$C_{0-4}$alkylC(=O)N$R^9$(—CH$_2$—CH$_2$—O—$R^{10}$—)$_2$, —N($R^9$)CO$R^{10}$, —N($R^5$)C(=O)$R^{10}$, —N($R^9$)SO$_2R^{10}$, and common amino acid side chains;
$R^9$ and $R^{10}$ are independently selected from:
  H and $C_{1-4}$alkyl, wherein the N$R^9R^{10}$ group of $R^7$, $R^8$, $R^{7a}$, $R^{8a}$, $R^{7b}$ and $R^{8b}$ is optionally cyclized to form a 5–8 membered heterocyclic group;
J is a member selected from the group consisting of:
  a direct link, —C(=O)—N($R^{11}$)—(CH$_2$)$_{0-2}$, —N($R^{11}$)—(CH$_2$)$_{0-2}$—C(=O)—, and —N($R^{11}$)—(CH$_2$)$_{0-2}$;
$R^{11}$ is a member selected from the group consisting of:
  hydrogen, $C_{1-4}$alkyl, $C_{2-6}$alkenyl, $C_{0-4}$alkylaryl and a $C_{1-4}$alkylheterocyclic ring;
Z is a member selected from the group consisting of:
  (a) phenyl, which is independently substituted with 0–2 $R^{1b}$ substituents;
  (b) an aromatic heterocyclic ring having from 5 to 10 ring atoms, wherein 1–4 ring atoms are selected from N, O and S, and wherein the ring may be subsituted independently by from 0–2 $R^{1b}$ substituents; and
  (c) a fused aromatic bicyclic heterocyclic ring system having from 5 to 10 ring atoms, wherein 1–4 ring atoms of the ring system are selected from N, O and S, wherein the bicyclic ring system may be subsituted from 0–2 $R^{1b}$ substituents;

$R^{1b}$ is selected from:
halo, $C_{1-4}$alkyl, OH, OBn, O—$CH_2$—$CH_2$—OH, O—$CH_2$—$CH_2$—$OCH_3$, O—$CH_2$—COOH, O—$CH_2$—C(=O)—O—$CH_3$, $NH_2$, NH—$CH_2$—$CH_2$—O—$CH_3$, NH—C(=O)—O—$CH_3$, and NH—$SO_2$—$CH_3$;

L is selected from:
H, C(=O)$NR^{12}R^{13}$, $(CH_2)_n NR^{12}R^{13}$ and C(=$NR^{12}$)$NR^{12}R^{13}$;

$R^{12}$ and $R^{13}$ are independently selected from:
hydrogen and $C_{1-4}$alkyl;

and all pharmaceutically acceptable isomers, salts, hydrates, solvates and prodrug derivatives thereof.

In a further preferred embodiment, the present invention provides a compound according to formula I:

A—D—E—G—J—Z—L

Wherein:
A is a member selected from the group consisting of:

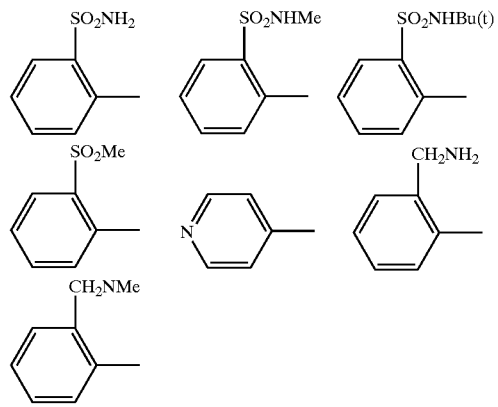

D is a member selected from the group consisting of:

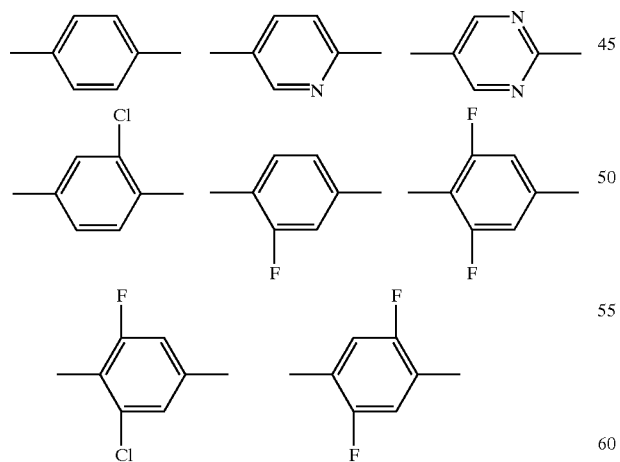

E is a member selected from the group consisting of:
—C(=O)—NH—, —C(=O)—N(—$CH_3$)—, C(=O)—N(-Bn)—, —NH—C(—O)—, —N(—$CH_3$)C(=O)— and —N(-Bn)C(=O)—;

G is selected from:

—CH(—$NH_2$)—$CH_2$—, —CH—(—NH(C(=O)—$CH_3$))—$CH_2$—, —CH—(—NH(C(=O)-Ph))—$CH_2$—, —CH—(C(=O)—$OR^8$)—, —CH(—$R^7$)—, —$CH_2$—CH(C(=O)—$OR^8$)—, and —$CH_2$—CH(C(=O)—N(—$R^8$, —$R^8$))—;

$R^7$ is a member selected from the group consisting of:
H, phenyl, Bn, and cycohexyl;

$R^8$ is a member selected from the group consisting of:
H, $C_{1-6}$alkyl, and $C_{3-6}$cycloalkyl;

J is a member selected from the group consisting of;
—C(=O)—N($R^{11}$)—$(CH_2)_{0-2}$, —N($R^{11}$)—$(CH_2)_{0-2}$—C(=O)—, and —N($R^{11}$)—$(CH_2)_{0-2}$;

$R^{11}$ is a member selected from the group consisting of:
H, methyl, phenyl and benzyl; and Z and L taken together are a member selected from the group consisting of:

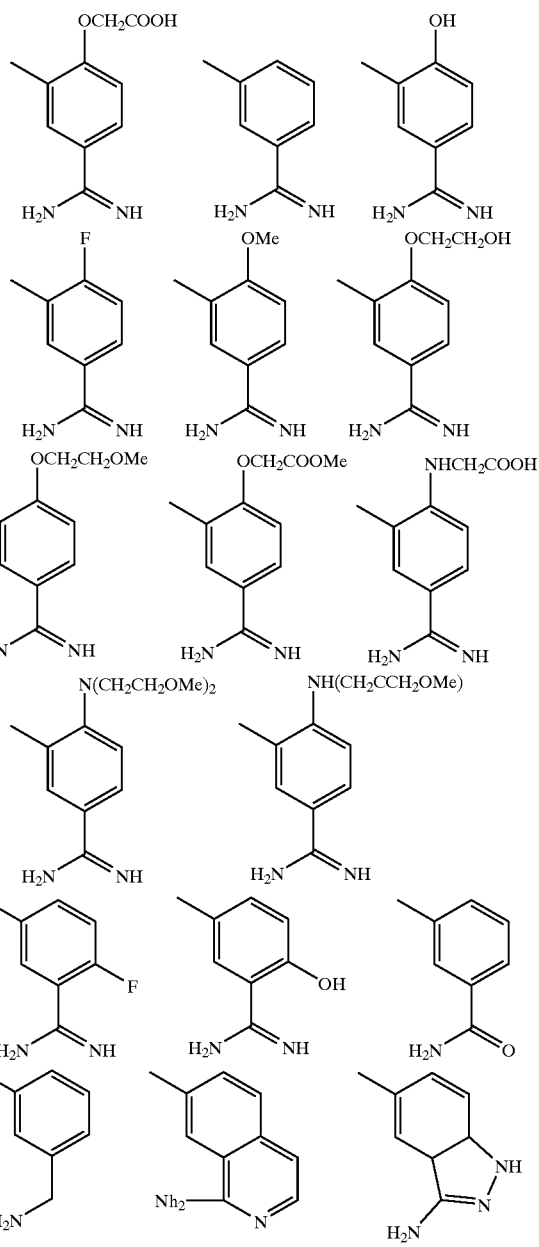

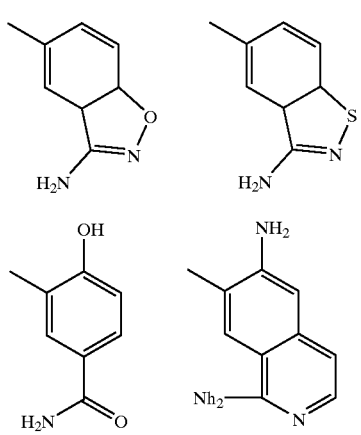
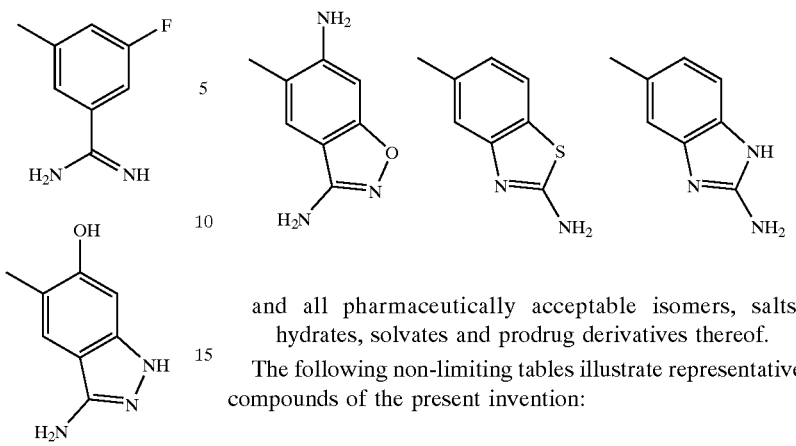

and all pharmaceutically acceptable isomers, salts, hydrates, solvates and prodrug derivatives thereof.

The following non-limiting tables illustrate representative compounds of the present invention:

TABLE 1

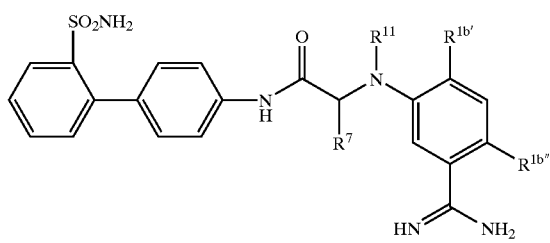

Formula II

| $R^7$ | $R^{11}$ | $R^{1b'}$ | $R^{1b''}$ |
|---|---|---|---|
| H | H | H | H |
| Me | Me | H | OH |
| 3-methylphenyl | phenyl | F | H |
| 4-hydroxy-3-methylphenyl | benzyl | —OH | F |
| cyclohexyl | 3-hydroxybenzyl | Br | OH |
| benzyl | 3-methoxybenzyl | —NH2 | OH |

TABLE 1-continued
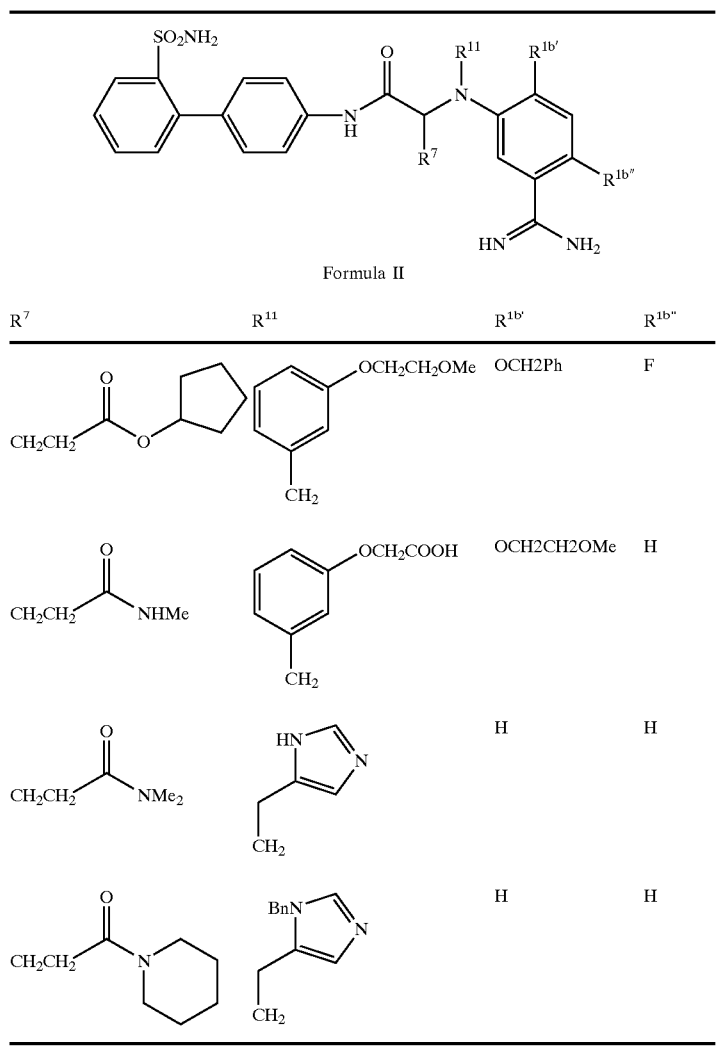
Formula II
TABLE 2
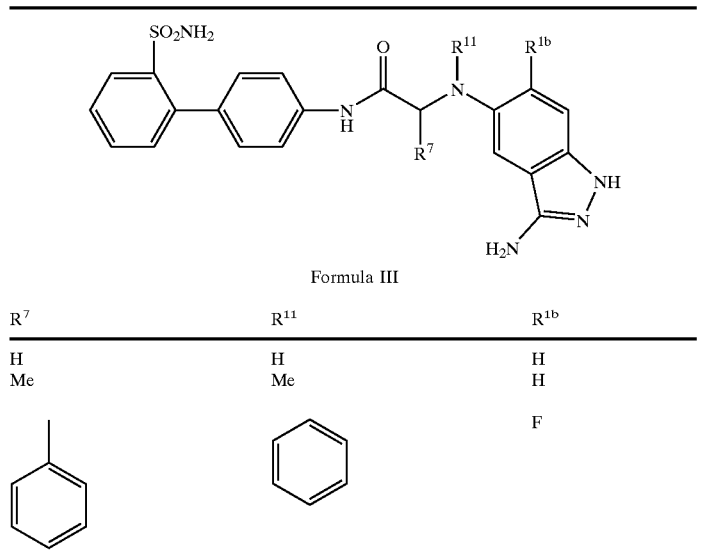
Formula III
| R⁷ | R¹¹ | R¹ᵇ |
|---|---|---|
| H | H | H |
| Me | Me | H |
| (tolyl-CH₂) | (phenyl) | F |

TABLE 2-continued
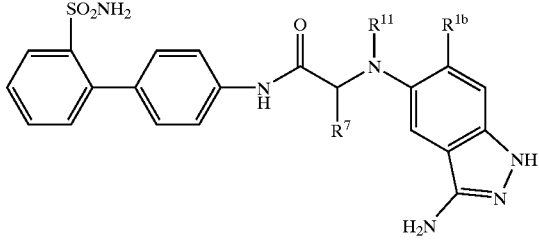
Formula III
| R⁷ | R¹¹ | R¹ᵇ |
|---|---|---|
| 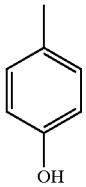 | 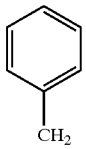 | —OH |
| 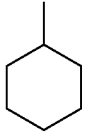 | 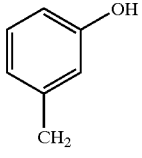 | Br |
| 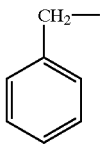 | 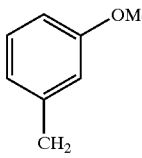 | —NH2 |
| 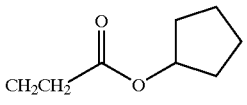 | 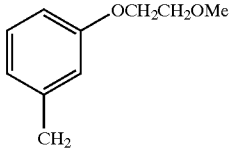 | OCH2Ph |
| 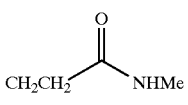 | 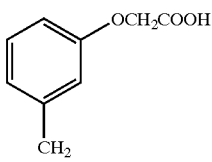 | OCH2CH2OMe |
| 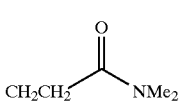 | 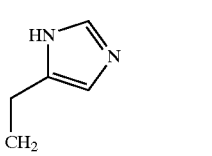 | H |
| 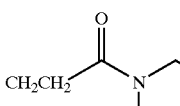 |  | H |

TABLE 3
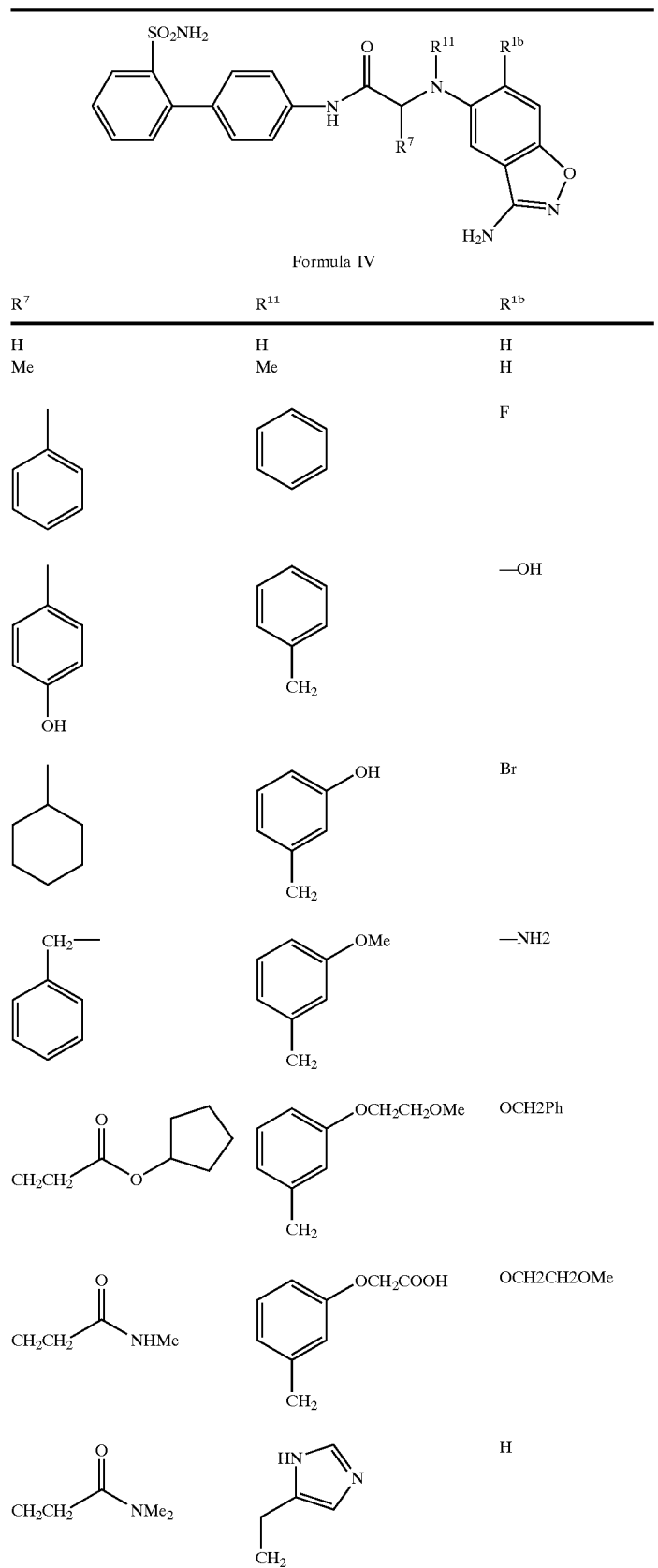
Formula IV
| R⁷ | R¹¹ | R¹ᵇ |
|---|---|---|
| H | H | H |
| Me | Me | H |
| 4-methylphenyl | phenyl | F |
| 4-hydroxyphenyl | benzyl (PhCH₂) | —OH |
| cyclohexyl | 3-hydroxybenzyl | Br |
| benzyl (PhCH₂) | 3-methoxybenzyl | —NH2 |
| CH₂CH₂C(O)O-cyclopentyl | 3-(OCH₂CH₂OMe)benzyl | OCH2Ph |
| CH₂CH₂C(O)NHMe | 3-(OCH₂COOH)benzyl | OCH2CH2OMe |
| CH₂CH₂C(O)NMe₂ | (1H-imidazol-5-yl)methyl | H |

TABLE 3-continued
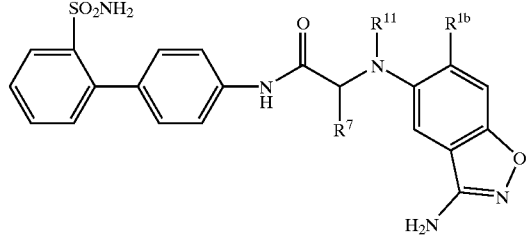
Formula IV
| R⁷ | R¹¹ | R¹ᵇ |
|---|---|---|
| 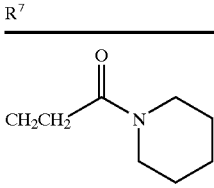 | 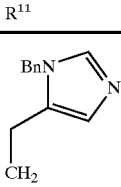 | H |
TABLE 4
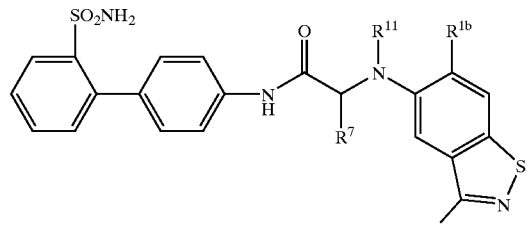
Formula V
| R⁷ | R¹¹ | R¹ᵇ |
|---|---|---|
| H | H | H |
| Me | Me | H |
| 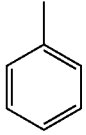 |  | F |
| 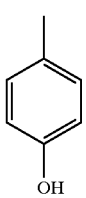 | 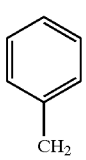 | —OH |
| 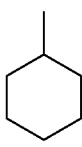 | 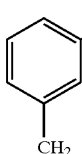 | Br |
| 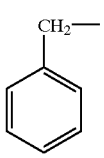 | 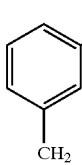 | —NH2 |

TABLE 4-continued
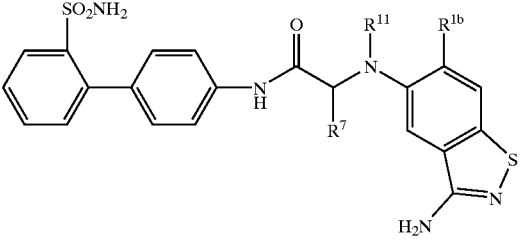
Formula V
| R⁷ | R¹¹ | R¹ᵇ |
|---|---|---|
| 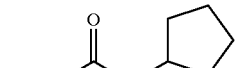 | 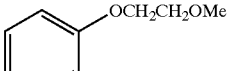 | OCH2Ph |
|  | 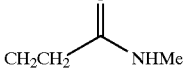 | OCH2CH2OMe |
| 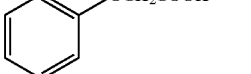 |  | H |
| 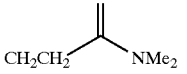 | 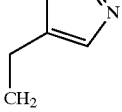 | H |
TABLE 5
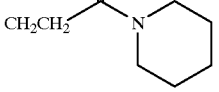
Formula VI
| R⁷ | R¹¹ | R¹ᵇ |
|---|---|---|
| H | H | H |
| Me | Me | H |
| 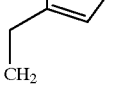 | 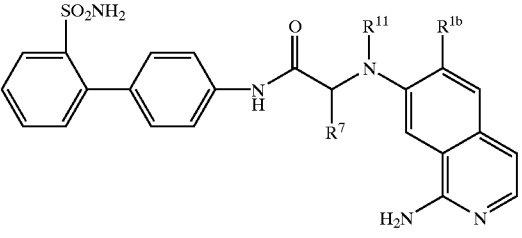 | F |

TABLE 5-continued
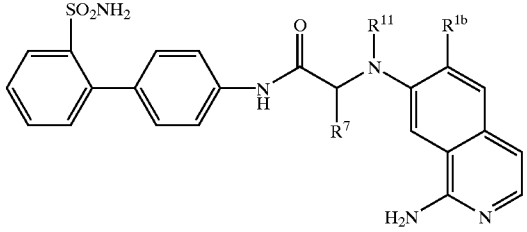
Formula VI
| R⁷ | R¹¹ | R¹ᵇ |
|---|---|---|
|  | 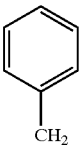 | —OH |
| 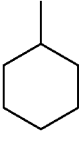 | 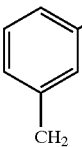 | Br |
| 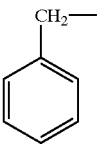 | 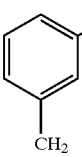 | —NH2 |
| 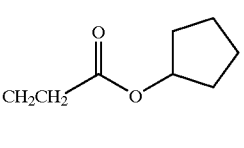 | 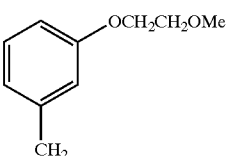 | OCH2Ph |
| 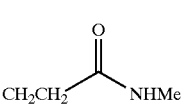 | 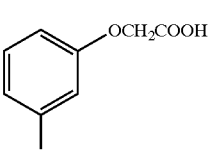 | OCH2CH2OMe |
| 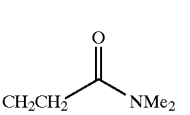 | 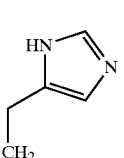 | H |
| 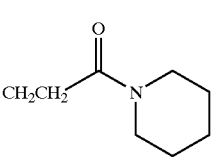 |  | H |

TABLE 6
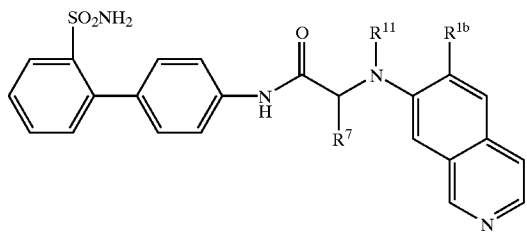
Formula VII
| R⁷ | R¹¹ | R¹ᵇ |
|---|---|---|
| H | H | H |
| Me | Me | H |
|  (4-methylphenyl) |  (phenyl) | F |
|  (4-hydroxyphenyl, OH) | 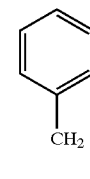 (CH₂-phenyl) | —OH |
|  (cyclohexyl) | 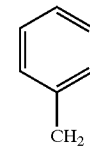 (3-hydroxybenzyl, OH, CH₂) | Br |
|  (CH₂-phenyl) | 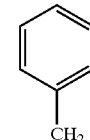 (3-methoxybenzyl, OMe, CH₂) | —NH2 |
| 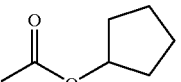 (CH₂CH₂-C(O)O-cyclopentyl) | 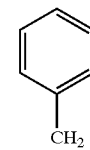 (3-(OCH₂CH₂OMe)benzyl, CH₂) | OCH2Ph |
| 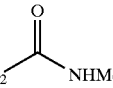 (CH₂CH₂C(O)NHMe) | 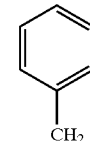 (3-(OCH₂COOH)benzyl, CH₂) | OCH2CH2OMe |
| 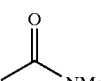 (CH₂CH₂C(O)NMe₂) | 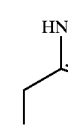 (imidazolyl-CH₂) | H |

TABLE 6-continued
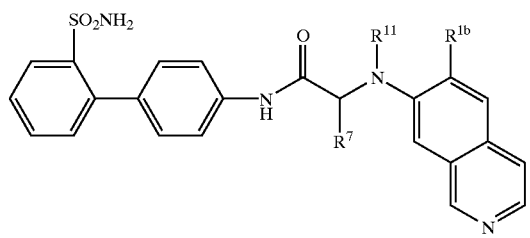
Formula VII
| R⁷ | R¹¹ | R¹ᵇ |
|---|---|---|
| 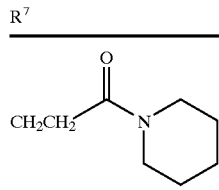 | 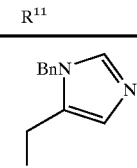 | H |
TABLE 7
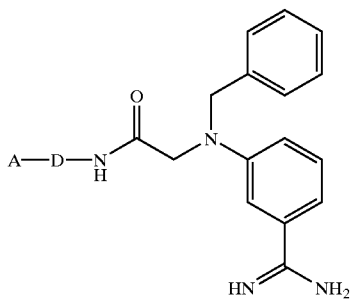
Formula VIII
| A | D |
|---|---|
| 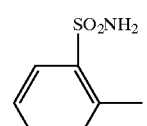 | 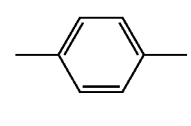 |
| 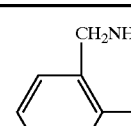 | 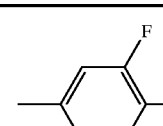 |
| 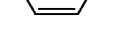 |  |
| 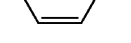 | 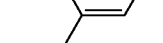 |
TABLE 7-continued
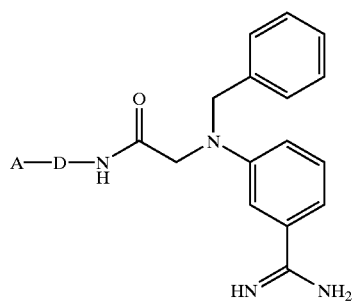
Formula VIII
| A | D |
|---|---|
|  | 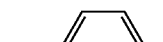 |
|  | 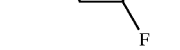 |
| 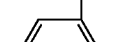 | 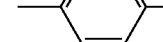 |
| 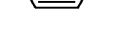 |  |

TABLE 7-continued

Formula VIII

TABLE 8

Formula IX

TABLE 8-continued
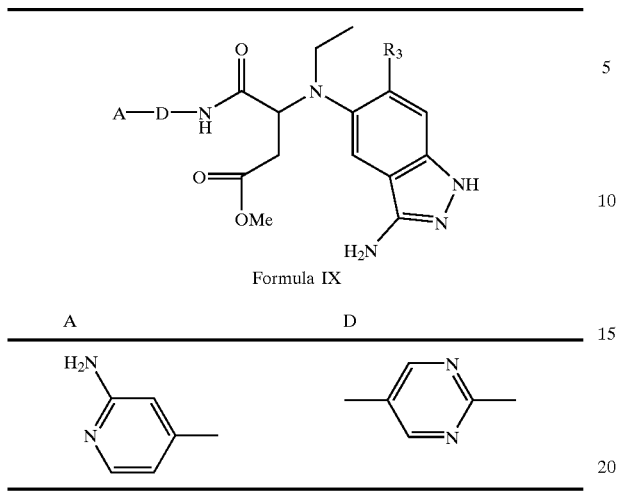
Formula IX
wherein R3 is a member selected from the group consisting of H, F, —OH, Br, Cl, —NH₂, —O—CH₂—O—Ph and —O—CH₂—CH₂—O—CH₃,
TABLE 9
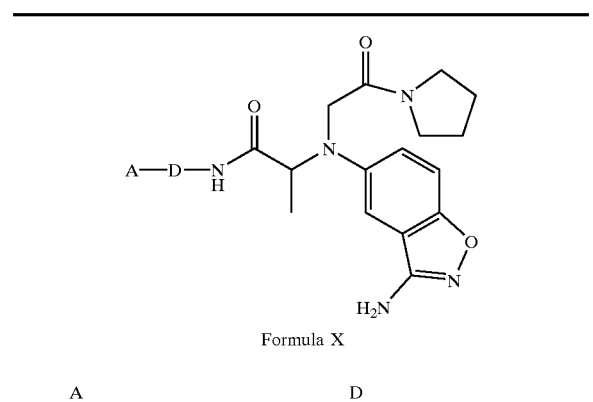
Formula X
TABLE 9-continued
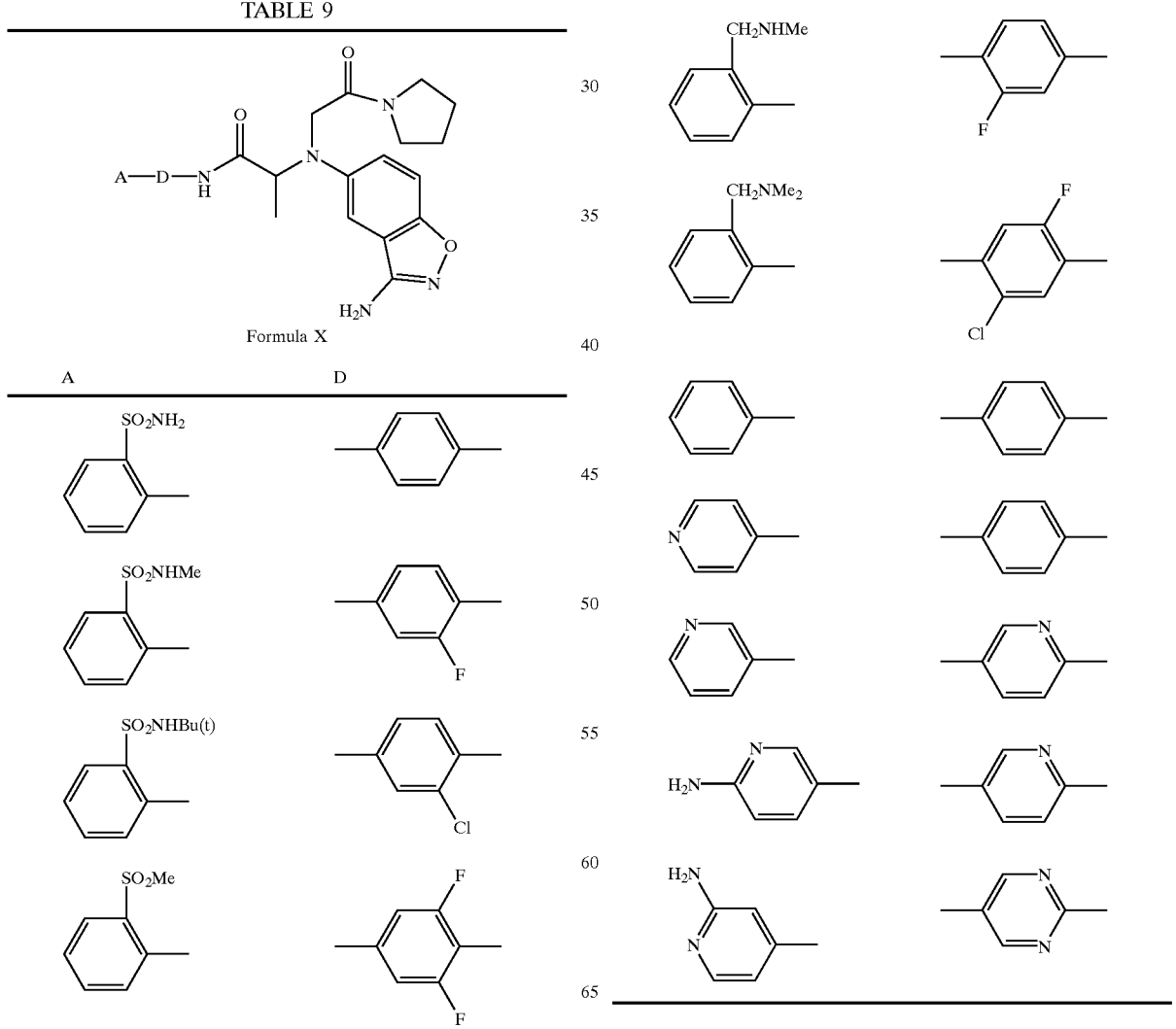
Formula X TABLE 10
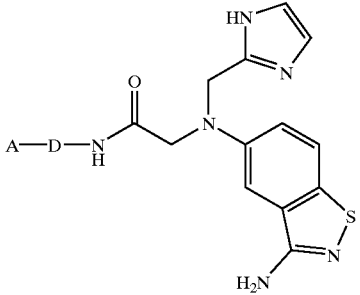
Formula XI
| A | D |
|---|---|
| 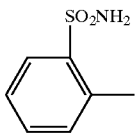 | 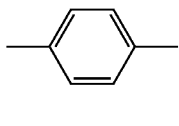 |
| 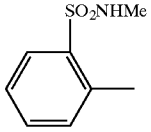 | 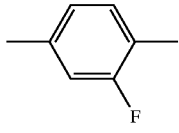 |
| 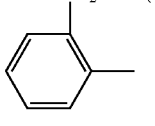 | 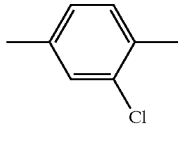 |
| 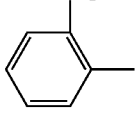 | 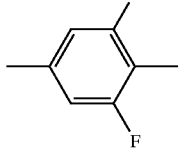 |
| 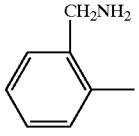 | 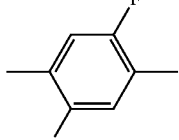 |
| 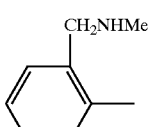 | 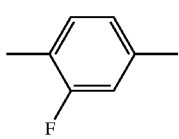 |
| 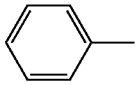 |  |
| 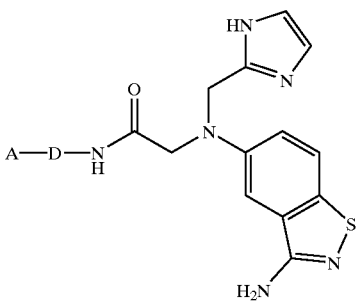 | 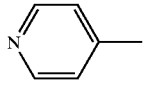 |
TABLE 10-continued
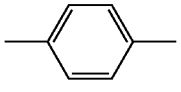
Formula XI
| A | D |
|---|---|
| 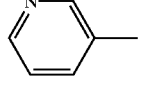 | 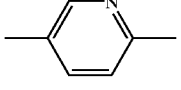 |
| 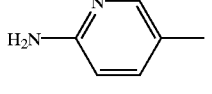 | 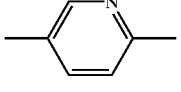 |
| 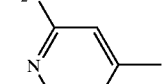 | 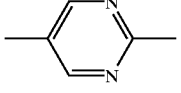 |
| 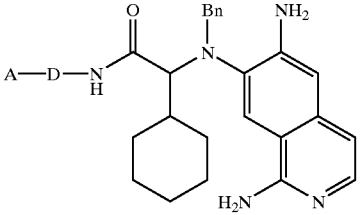 | 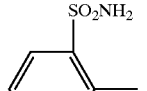 |
TABLE 11
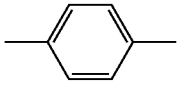
Formula XII
| A | D |
|---|---|
| 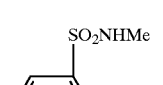 | |
| 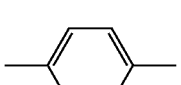 | |

TABLE 11-continued

Formula XII (chemical structure with substituents A—D—NH, Bn, NH₂, cyclohexyl, H₂N, N on isoquinoline ring system)

| A | D |
|---|---|
| 2-methylphenyl-SO₂NHBu(t) | 4-methyl-2-chlorophenyl |
| 2-methylphenyl-SO₂Me | 2,5-difluoro-4-methylphenyl |
| 2-methylphenyl-CH₂NH₂ | 2,5-difluoro-4-methylphenyl |
| 2-methylphenyl-CH₂NHMe | 3-fluoro-4-methylphenyl |
| 2-methylphenyl-CH₂NMe₂ | 2-fluoro-5-chloro-4-methylphenyl |
| phenyl | 4-methylphenyl |
| 4-pyridyl | 4-methylphenyl |
| 3-pyridyl | 2,5-pyridyl |
| 2-amino-5-pyridyl | 2,5-pyridyl |

TABLE 11-continued

Formula XII (chemical structure as above)

| A | D |
|---|---|
| 2-amino-4-methylpyridyl | 2,5-dimethylpyrimidyl |

TABLE 12

Formula XIII (chemical structure with A—D—NH, 4-hydroxybenzyl, benzotriazole ring system)

| A | D |
|---|---|
| 2-methylphenyl-SO₂NH₂ | 4-methylphenyl |
| 2-methylphenyl-SO₂NHMe | 3-fluoro-4-methylphenyl |
| 2-methylphenyl-SO₂NHBu(t) | 3-chloro-4-methylphenyl |
| 3-methylpyridyl-SO₂Me | 2,5-difluoro-4-methylphenyl |

TABLE 12-continued
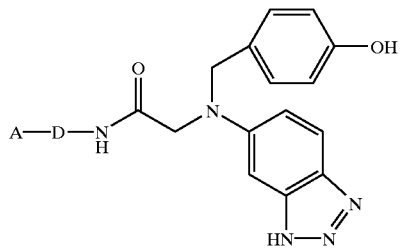
Formula XIII
| A | D |
|---|---|
| 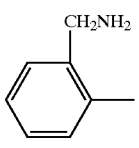 | 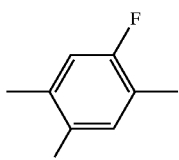 |
| 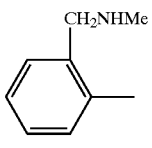 | 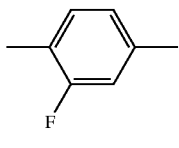 |
| 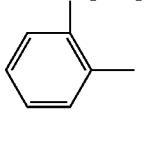 | 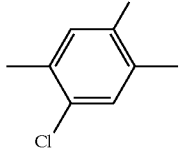 |
| 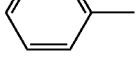 | 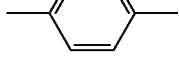 |
| 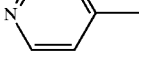 | 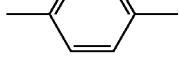 |
| 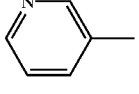 | 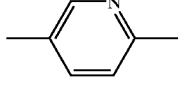 |
| 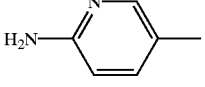 | 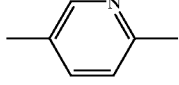 |
| 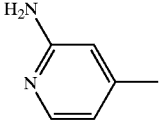 | 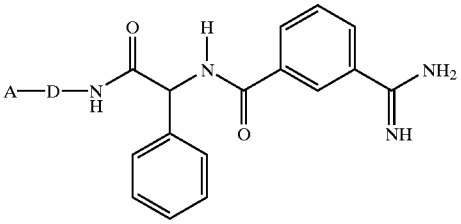 |
TABLE 13
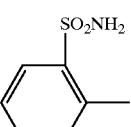
Formula XIV
| A | D |
|---|---|
| 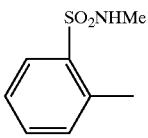 | 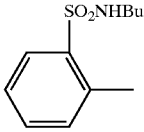 |
| 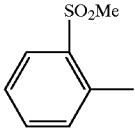 | 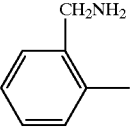 |
| 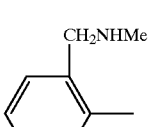 | 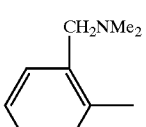 |
| 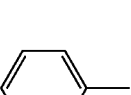 | |

TABLE 13-continued
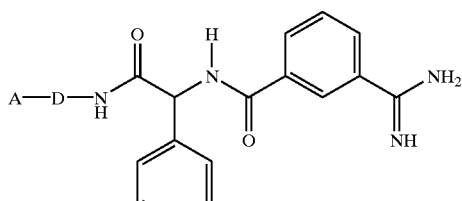
Formula XIV
TABLE 14
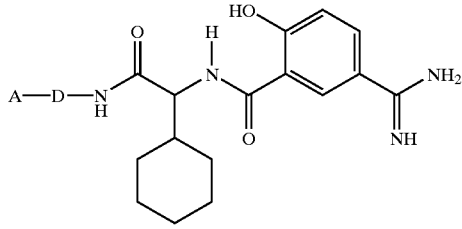
Formula XV
TABLE 14-continued
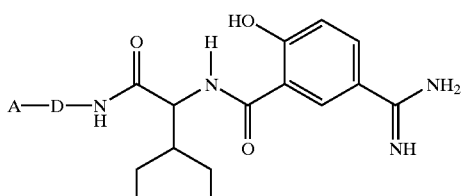
Formula XV

TABLE 15
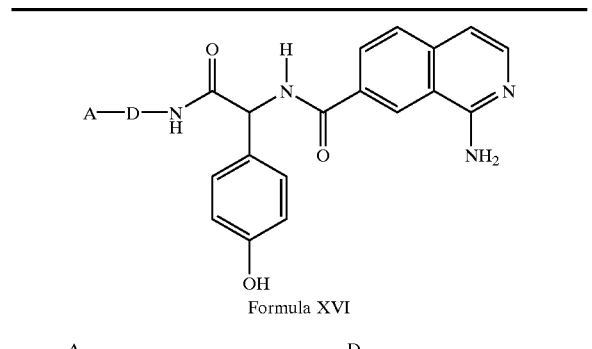
Formula XVI
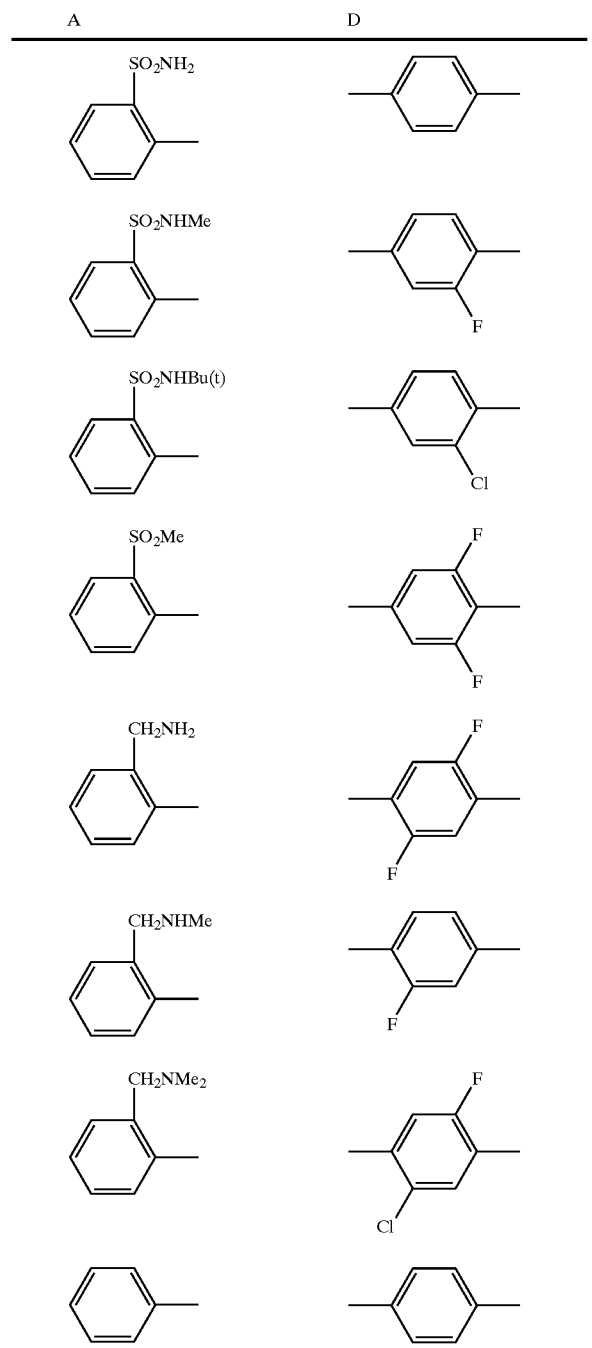
TABLE 15-continued
Formula XVI
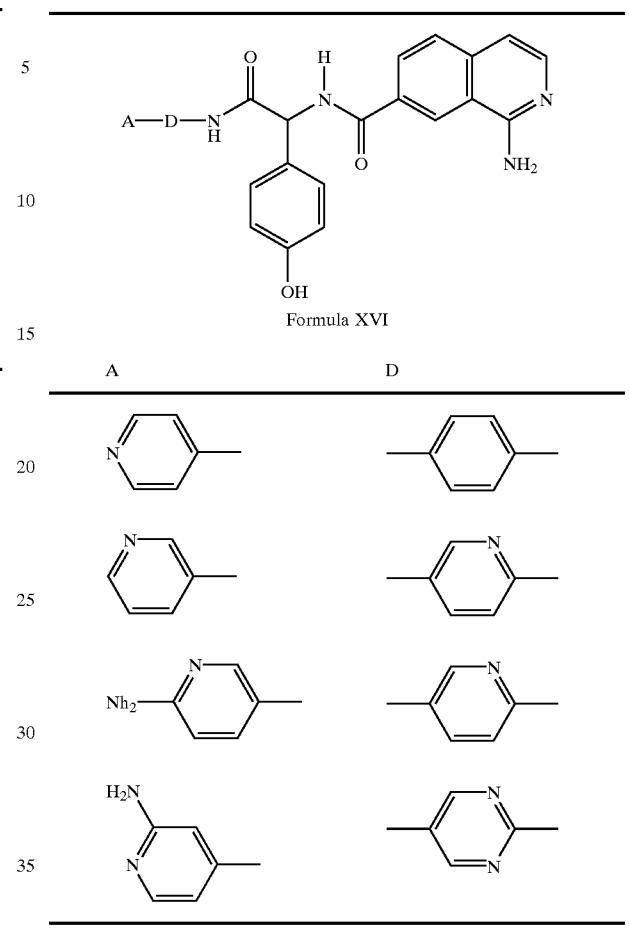
TABLE 16
Formula XVII
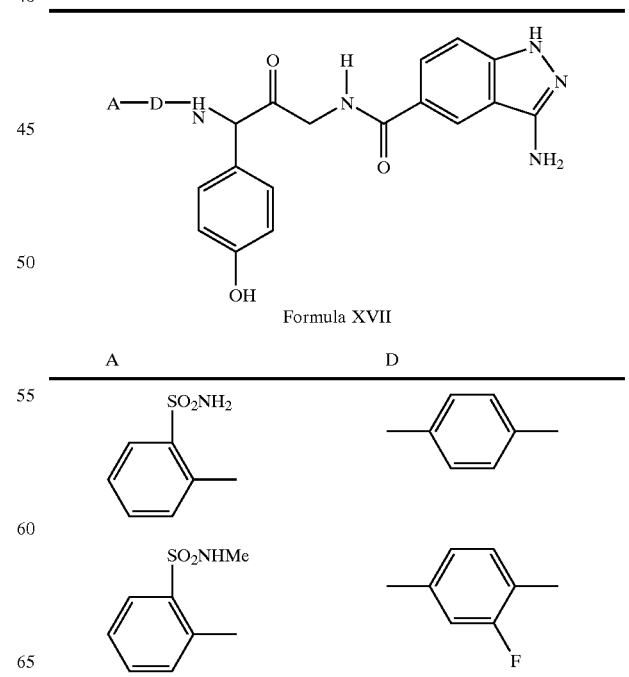

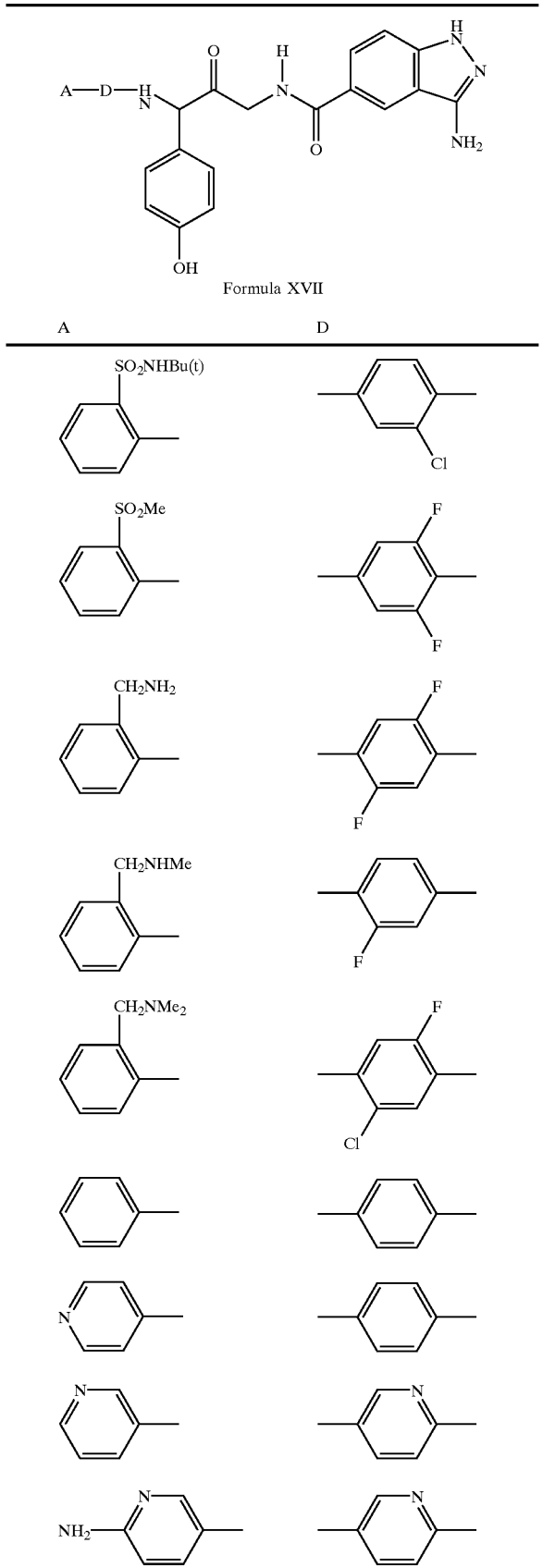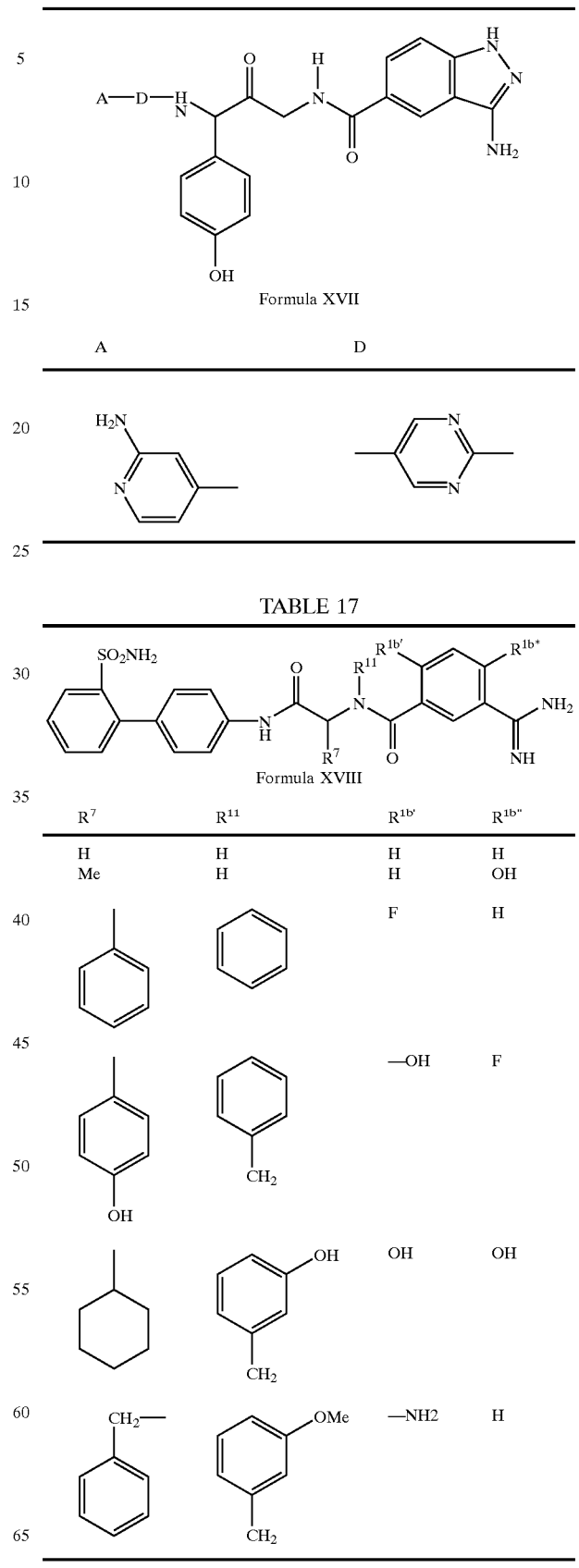

TABLE 18
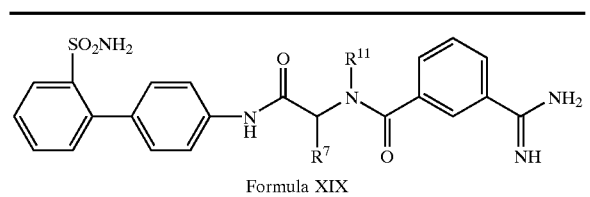
Formula XIX
| R⁷ | R¹¹ |
|---|---|
| H | H |
| Me | H |
| 4-methylphenyl | phenyl |
| 4-hydroxyphenyl | benzyl |
| cyclohexyl | 3-hydroxybenzyl |
| benzyl | 3-methoxybenzyl |
TABLE 19
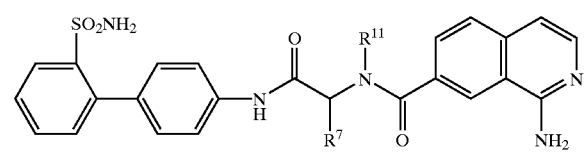
Formula XX
| R⁷ | R¹¹ |
|---|---|
| H | H |
| Me | H |
TABLE 19-continued
Formula XX
| R⁷ | R¹¹ |
|---|---|
| 4-methylphenyl | phenyl |
| 4-hydroxyphenyl | benzyl |
| cyclohexyl | 3-hydroxybenzyl |
| benzyl | 3-methoxybenzyl |
TABLE 20
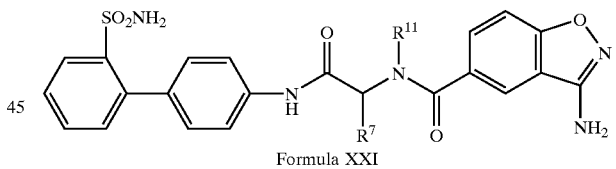
Formula XXI
| R⁷ | R¹¹ |
|---|---|
| H | H |
| Me | H |
| 4-methylphenyl | phenyl |
| 4-hydroxyphenyl | benzyl |

TABLE 20-continued

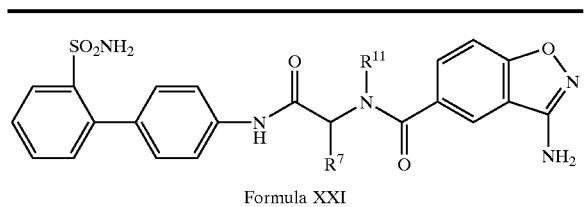

Formula XXI

| R[7] | R[11] |
|---|---|
| cyclohexyl | 3-hydroxybenzyl |
| benzyl | 3-methoxybenzyl |

TABLE 21

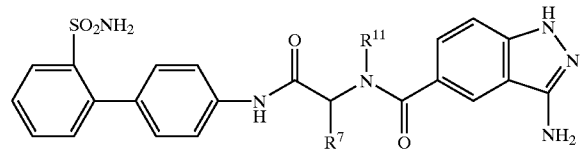

Formula XXII

| R[7] | R[11] |
|---|---|
| H | H |
| Me | H |
| 4-methylphenyl | phenyl |
| 4-hydroxy-4-methylphenyl | benzyl |
| cyclohexyl | 3-hydroxybenzyl |

TABLE 21-continued

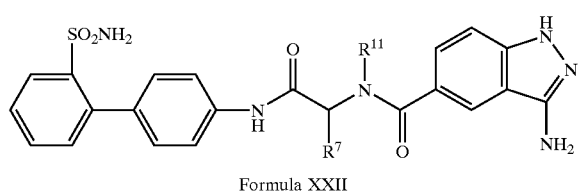

Formula XXII

| R[7] | R[11] |
|---|---|
| benzyl | 3-methoxybenzyl |

TABLE 22

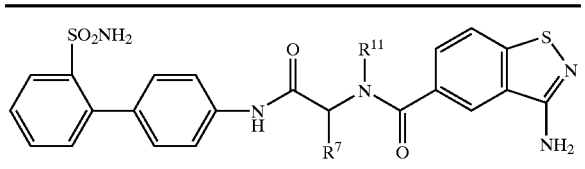

Formula XXIII

| R[7] | R[11] |
|---|---|
| H | H |
| Me | H |
| 4-methylphenyl | phenyl |
| 4-hydroxy-4-methylphenyl | benzyl |
| cyclohexyl | 3-hydroxybenzyl |
| benzyl | 3-methoxybenzyl |

TABLE 23
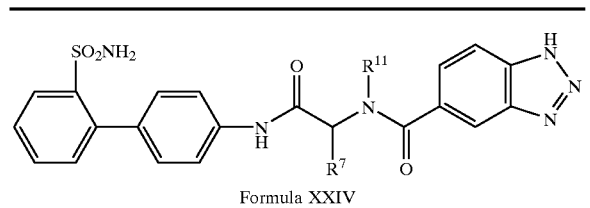
Formula XXIV
| R⁷ | R¹¹ |
|---|---|
| H | H |
| Me | H |
(additional R⁷/R¹¹ substituent pairs shown as structures)
TABLE 24
Formula XXV
| R⁷ | R¹¹ |
|---|---|
| H | H |
| Me | H |
TABLE 24-continued
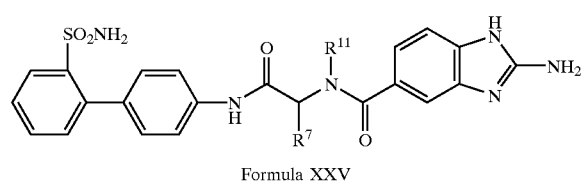
Formula XXV
| R⁷ | R¹¹ |
|---|---|
(substituent structures shown)
TABLE 25
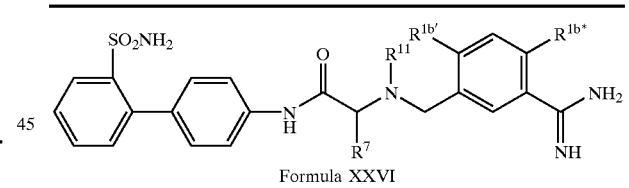
Formula XXVI
| R⁷ | R¹¹ | R¹ᵇ' | R¹ᵇ" |
|---|---|---|---|
| H | H | H | H |
| Me | H | H | OH |
| | | F | H |
| | | —OH | F |
(additional substituent structures shown)

TABLE 25-continued

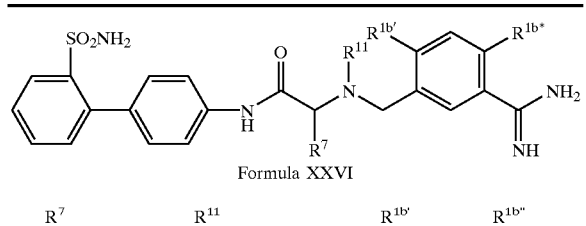
Formula XXVI

| R[7] | R[11] | R[1b'] | R[1b"] |
|---|---|---|---|
| cyclohexyl | 3-hydroxybenzyl | OH | OH |
| benzyl | 3-methoxybenzyl | —NH2 | H |

TABLE 26

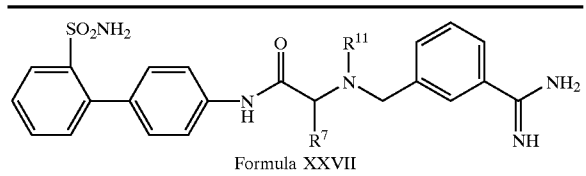
Formula XXVII

| R[7] | R[11] |
|---|---|
| H | H |
| Me | H |
| phenyl | benzyl |
| 4-hydroxyphenyl | benzyl |
| cyclohexyl | 3-hydroxybenzyl |
| benzyl | 3-methoxybenzyl |

TABLE 27

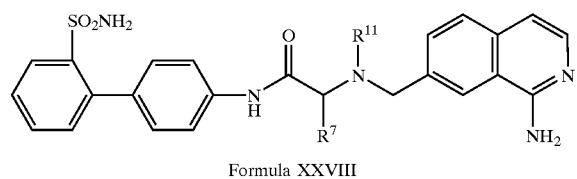
Formula XXVIII

| R[7] | R[11] |
|---|---|
| H | H |
| Me | H |
| phenyl | phenyl |
| 4-hydroxyphenyl | benzyl |
| cyclohexyl | 3-hydroxybenzyl |
| benzyl | 3-methoxybenzyl |

TABLE 28

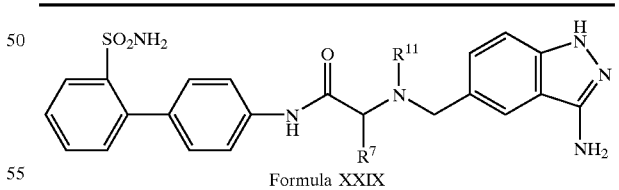
Formula XXIX

| R[7] | R[11] |
|---|---|
| H | H |
| Me | H |
| phenyl | phenyl |

TABLE 28-continued
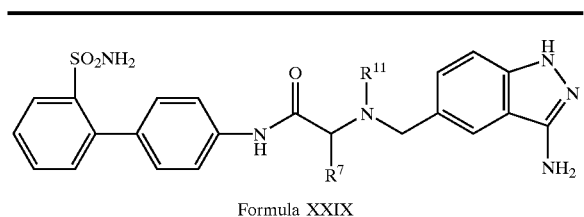
Formula XXIX
| R[7] | R[11] |
|---|---|
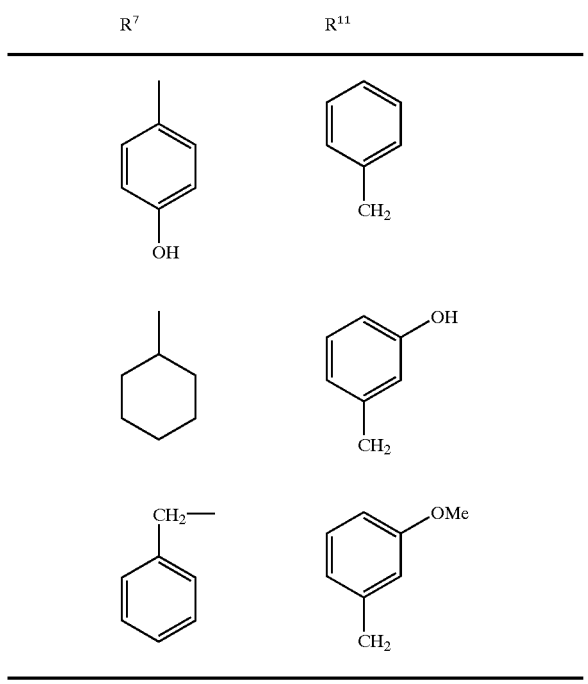
TABLE 29
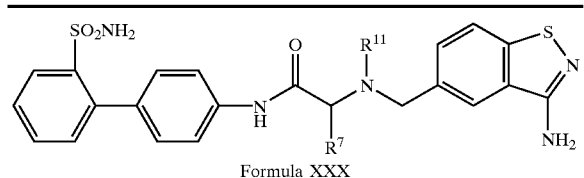
Formula XXX
| R[7] | R[11] |
|---|---|
| H | H |
| Me | H |
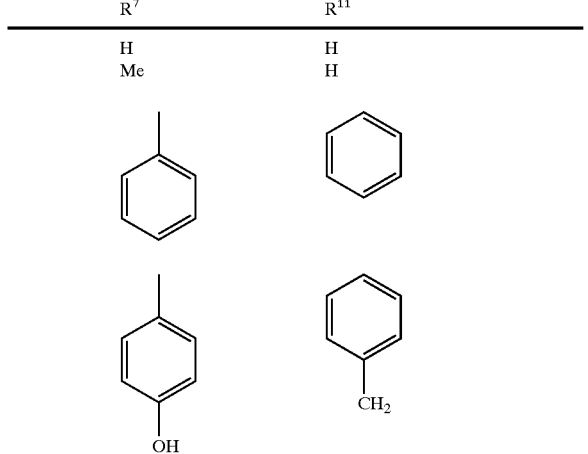
TABLE 29-continued
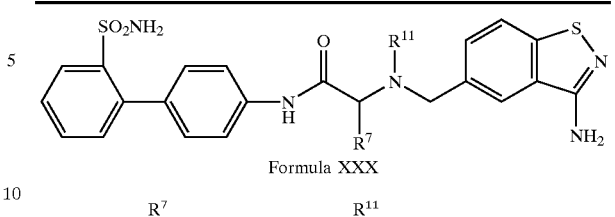
Formula XXX
| R[7] | R[11] |
|---|---|
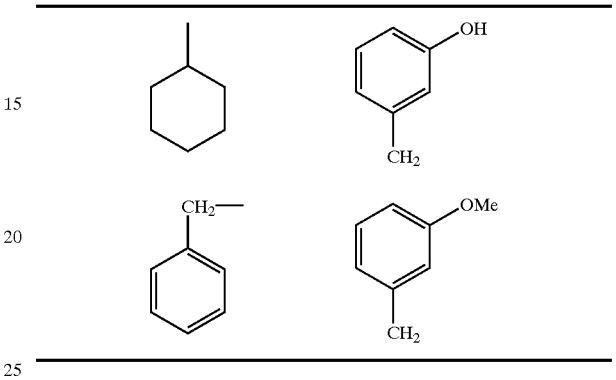
TABLE 30
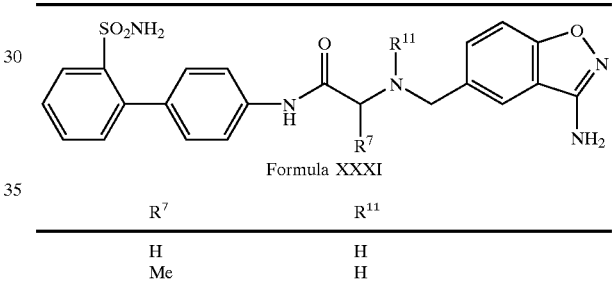
Formula XXXI
| R[7] | R[11] |
|---|---|
| H | H |
| Me | H |
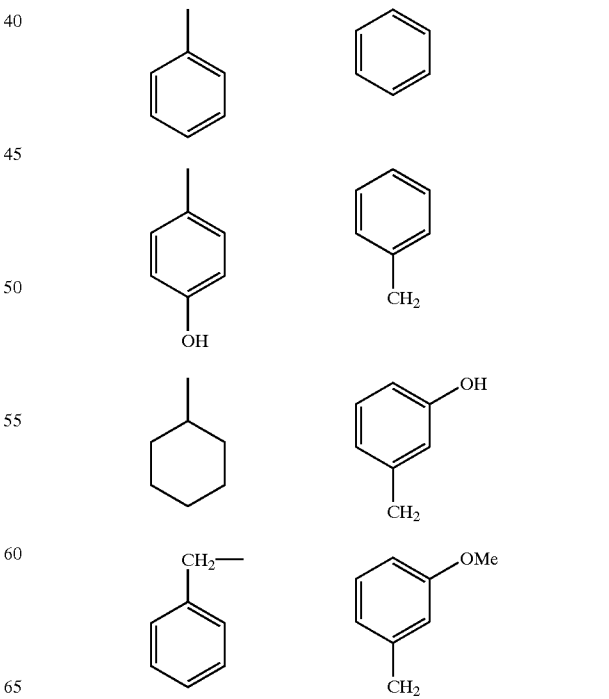

TABLE 31
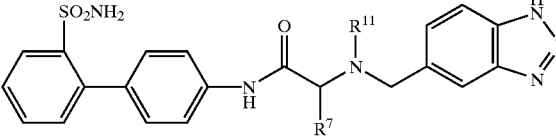
Formula XXXII
| R⁷ | R¹¹ |
|---|---|
| H | H |
| Me | H |
| 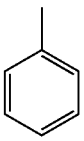 | 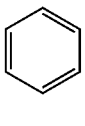 |
| 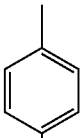 | 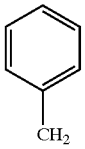 |
| 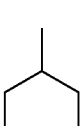 | 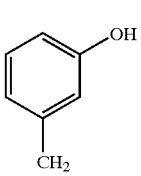 |
| 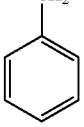 | 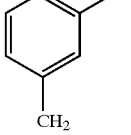 |
TABLE 32
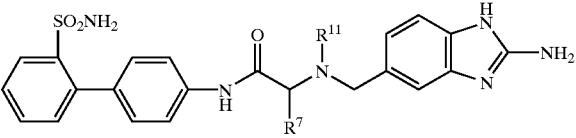
Formula XXXIII
| R⁷ | R¹¹ |
|---|---|
| H | H |
| Me | H |
| 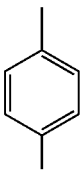 | 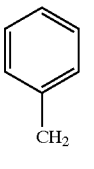 |
TABLE 32-continued
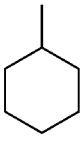
Formula XXXIII
| R⁷ | R¹¹ |
|---|---|
| 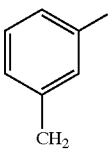 | 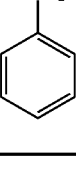 |
| 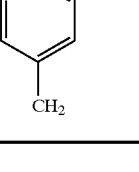 | 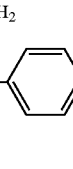 |
| 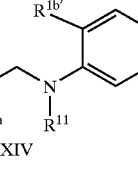 | 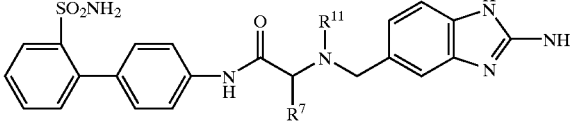 |
TABLE 33
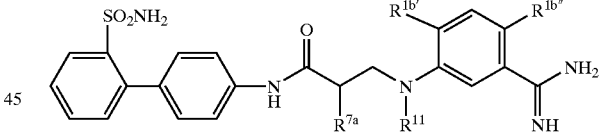
Formula XXXIV
| R⁷ᵃ | R¹¹ | R¹ᵇ' | R¹ᵇ'' |
|---|---|---|---|
| H | H | H | H |
| Me | H | H | OH |
|  |  | F | H |
| 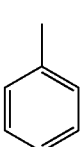 | 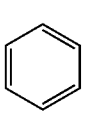 |  |  |
|  |  | —OH | F |
| 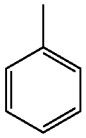 | 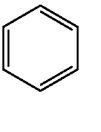 |  |  |

TABLE 33-continued

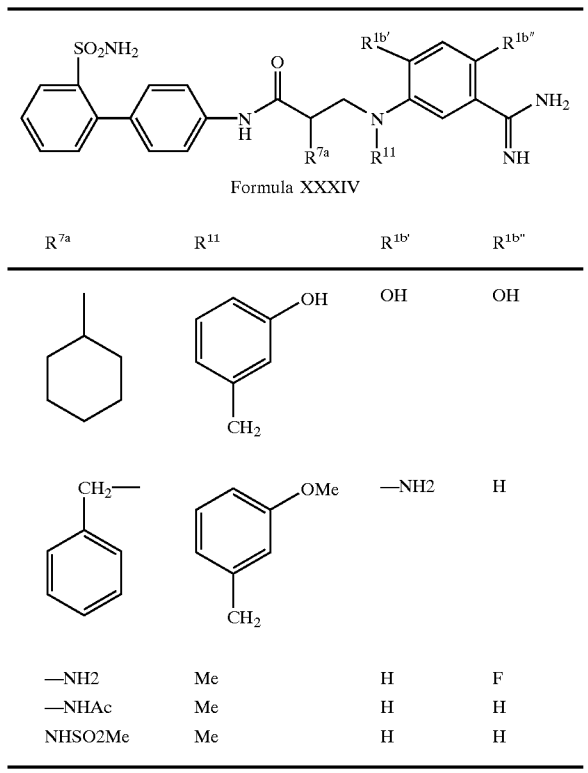

Formula XXXIV

| R7a | R11 | R1b' | R1b" |
|---|---|---|---|
| (cyclohexyl) | (3-hydroxybenzyl) | OH | OH |
| (benzyl) | (3-methoxybenzyl) | —NH2 | H |
| —NH2 | Me | H | F |
| —NHAc | Me | H | H |
| NHSO2Me | Me | H | H |

TABLE 34

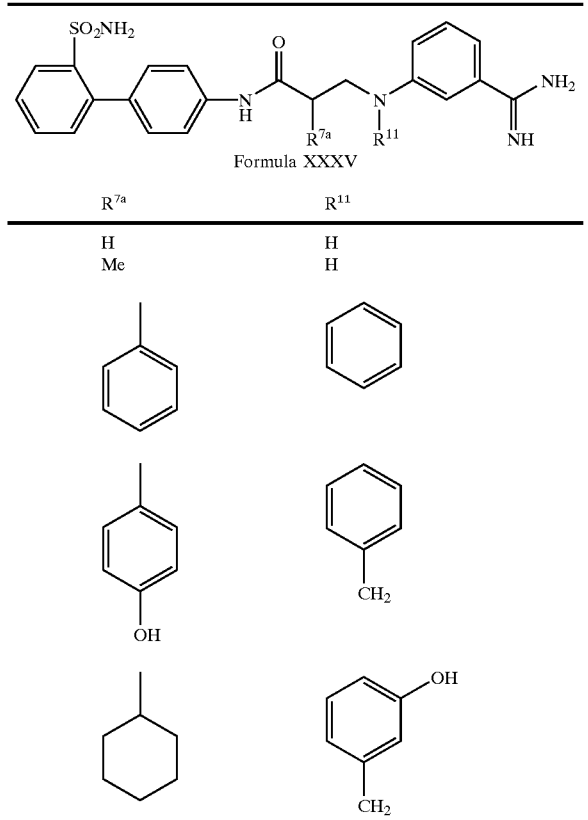

Formula XXXV

| R7a | R11 |
|---|---|
| H | H |
| Me | H |
| (3-methylphenyl) | (phenyl) |
| (4-hydroxyphenyl) | (benzyl) |
| (cyclohexyl) | (3-hydroxybenzyl) |

TABLE 34-continued

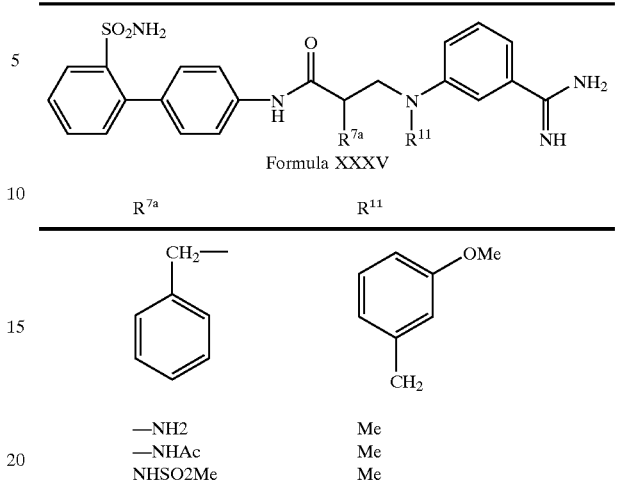

Formula XXXV

| R7a | R11 |
|---|---|
| (benzyl) | (3-methoxybenzyl) |
| —NH2 | Me |
| —NHAc | Me |
| NHSO2Me | Me |

TABLE 35

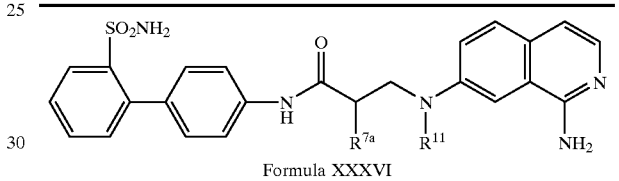

Formula XXXVI

| R7a | R11 |
|---|---|
| H | H |
| Me | H |
| (3-methylphenyl) | (phenyl) |
| (4-hydroxyphenyl) | (benzyl) |
| (cyclohexyl) | (3-hydroxybenzyl) |
| (benzyl) | (3-methoxybenzyl) |
| —NH2 | Me |
| —NHAc | Me |
| NHSO2Me | Me |

TABLE 36
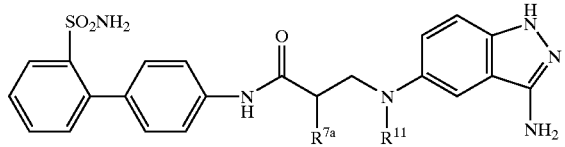
Formula XXXVII
| $R^{7a}$ | $R^{11}$ |
|---|---|
| H | H |
| Me | H |
| 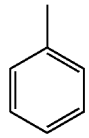 |  |
| 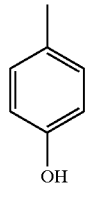 | 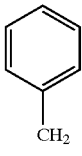 |
| 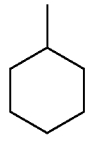 | 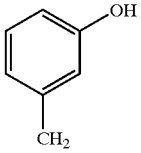 |
| 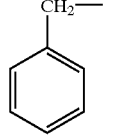 | 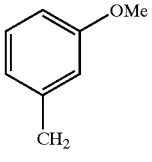 |
| —NH2 | Me |
| —NHAc | Me |
| NHSO2Me | Me |
TABLE 37
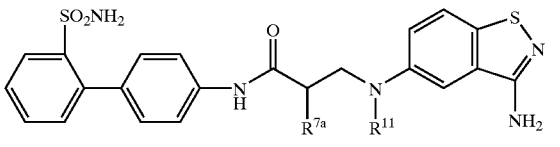
Formula XXXVIII
| $R^{7a}$ | $R^{11}$ |
|---|---|
| H | H |
| Me | H |
| 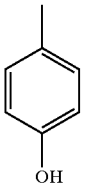 | 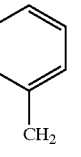 |
TABLE 37-continued
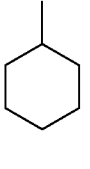
Formula XXXVIII
| $R^{7a}$ | $R^{11}$ |
|---|---|
| 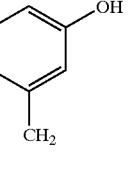 | 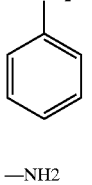 |
| 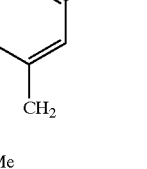 |  |
| 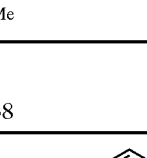 | 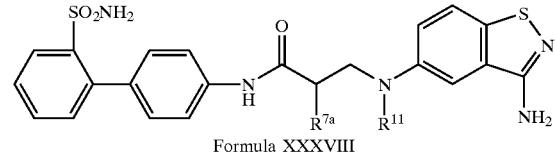 |
| —NH2 | Me |
| —NHAc | Me |
| NHSO2Me | Me |
TABLE 38
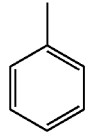
Formula XXIX
| $R^{7a}$ | $R^{11}$ |
|---|---|
| H | H |
| Me | H |
|  | 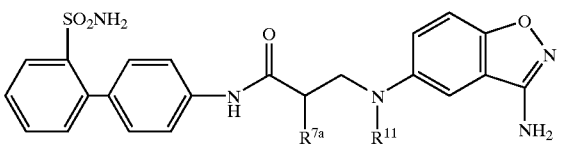 |
| 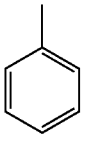 | 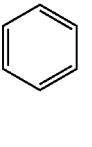 |

TABLE 38-continued

Formula XXIX (structure: biphenyl-SO₂NH₂ with amide linker, R⁷a, R¹¹, connected to 3-amino-1,2-benzisoxazol-5-yl group)

| R⁷a | R¹¹ |
|---|---|
| cyclohexyl | 3-hydroxybenzyl (CH₂-C₆H₄-OH) |
| benzyl (CH₂-C₆H₅) | 3-methoxybenzyl (CH₂-C₆H₄-OMe) |
| —NH2 | Me |
| —NHAc | Me |
| NHSO2Me | Me |

TABLE 39

Formula XXXX (structure: biphenyl-SO₂NH₂ with amide linker, R⁷a, R¹¹, connected to 1H-benzotriazol-5-yl group)

| R⁷a | R¹¹ |
|---|---|
| H | H |
| Me | H |
| 3-methylphenyl | phenyl |
| 4-hydroxyphenyl | benzyl (CH₂-C₆H₅) |
| cyclohexyl | 3-hydroxybenzyl (CH₂-C₆H₄-OH) |

TABLE 39-continued

Formula XXXX

| R⁷a | R¹¹ |
|---|---|
| benzyl (CH₂-C₆H₅) | 3-methoxybenzyl (CH₂-C₆H₄-OMe) |
| —NH2 | Me |
| —NHAc | Me |
| NHSO2Me | Me |

TABLE 40

Formula XXXXI (structure: biphenyl-SO₂NH₂ with amide linker, R⁷a, R¹¹, connected to 2-amino-1H-benzimidazol-5-yl group)

| R⁷a | R¹¹ |
|---|---|
| H | H |
| Me | H |
| 3-methylphenyl | phenyl |
| 4-hydroxyphenyl | benzyl (CH₂-C₆H₅) |
| cyclohexyl | 3-hydroxybenzyl (CH₂-C₆H₄-OH) |
| benzyl (CH₂-C₆H₅) | 3-methoxybenzyl (CH₂-C₆H₄-OMe) |
| —NH2 | Me |
| —NHAc | Me |
| NHSO2Me | Me |

TABLE 41
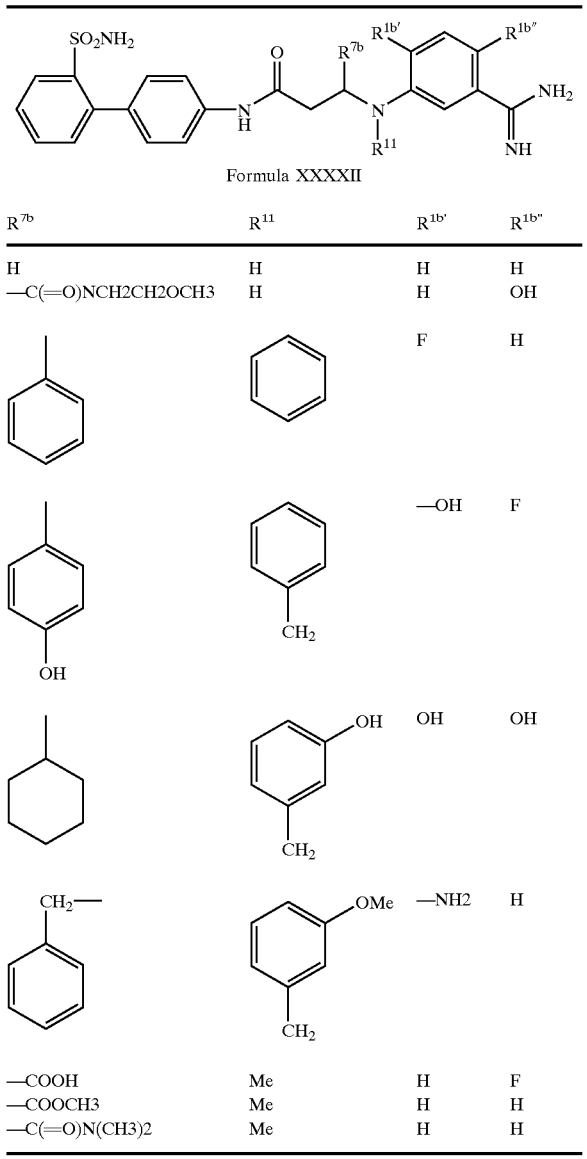
TABLE 42
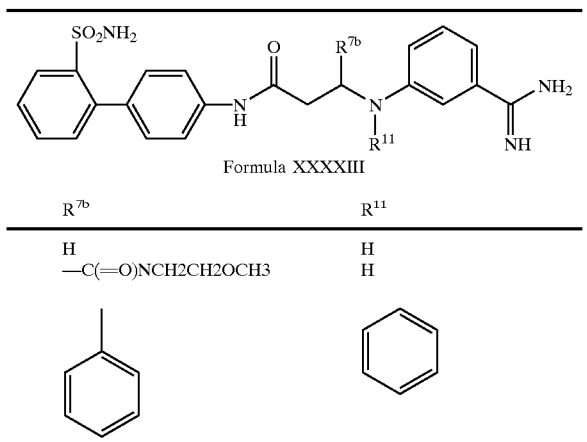
TABLE 42-continued
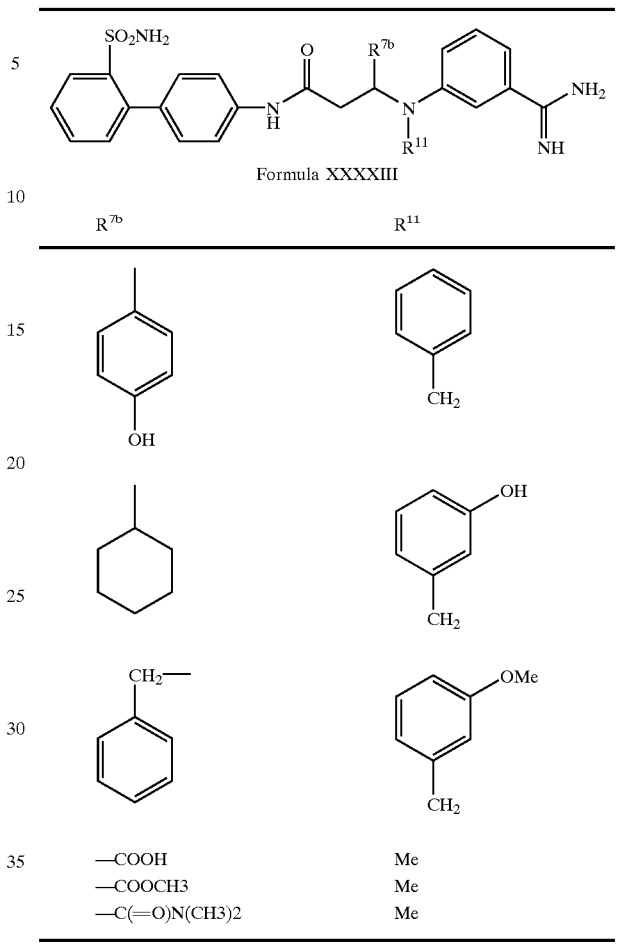
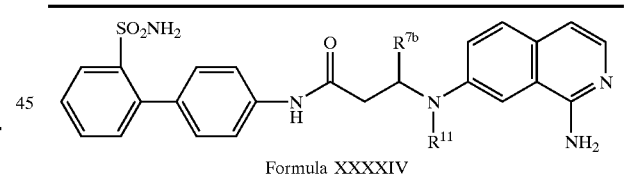
TABLE 43
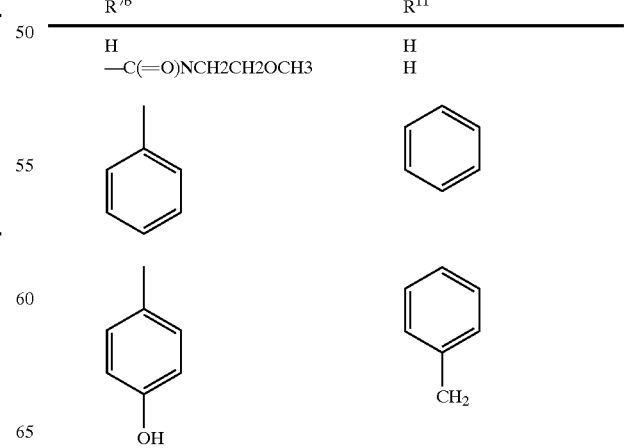

TABLE 43-continued
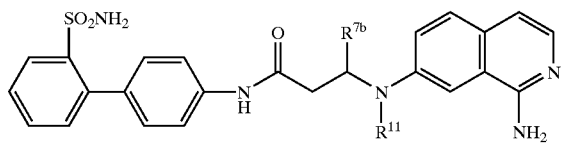
Formula XXXXIV
| $R^{7b}$ | $R^{11}$ |
|---|---|
| 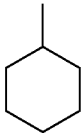 | 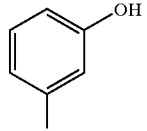 |
| 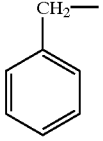 | 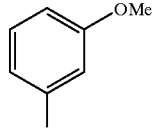 |
| —COOH | Me |
| —COOCH3 | Me |
| —C(=O)N(CH3)2 | Me |
TABLE 44
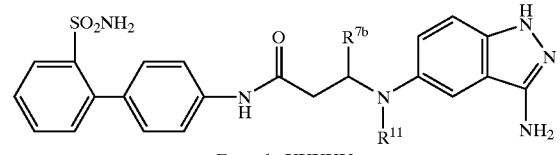
Formula XXXXV
| $R^{7b}$ | $R^{11}$ |
|---|---|
| H | H |
| —C(=O)NCH2CH2OCH3 | H |
| 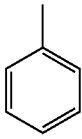 | 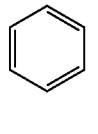 |
| 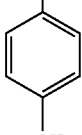 | 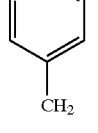 |
| 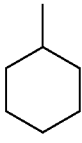 | 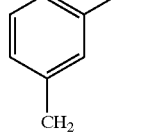 |
TABLE 44-continued
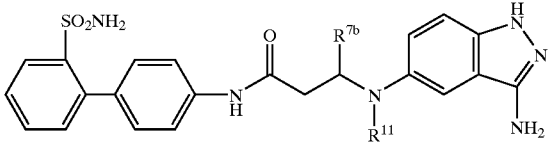
Formula XXXXV
| $R^{7b}$ | $R^{11}$ |
|---|---|
| 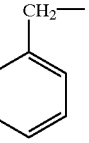 | 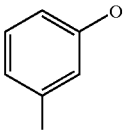 |
| —COOH | Me |
| —COOCH3 | Me |
| —C(=O)N(CH3)2 | Me |
TABLE 45
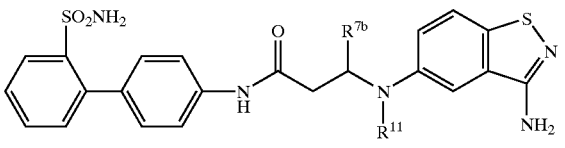
Formula XXXXVI
| $R^{7b}$ | $R^{11}$ |
|---|---|
| H | H |
| —C(=O)NCH2CH2OCH3 | H |
| 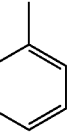 | 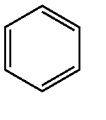 |
| 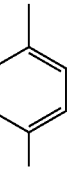 | 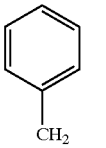 |
| 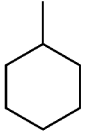 | 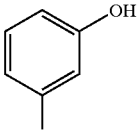 |
| 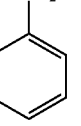 | 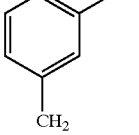 |
| —COOH | Me |
| —COOCH3 | Me |
| —C(=O)N(CH3)2 | Me |

TABLE 46
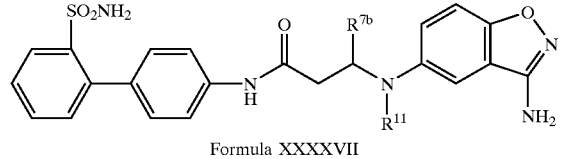
Formula XXXXVII
| R⁷ᵇ | R¹¹ |
|---|---|
| H | H |
| —C(=O)NCH2CH2OCH3 | H |
| 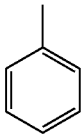 |  |
| 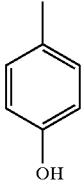 | 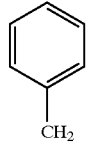 |
| 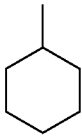 | 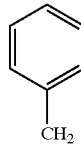 |
| 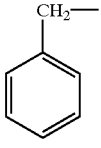 | 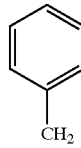 |
| —COOH | Me |
| —COOCH3 | Me |
| —C(=O)N(CH3)2 | Me |
TABLE 47
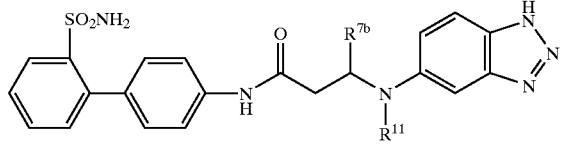
Formula XXXXVIII
| R⁷ᵇ | R¹¹ |
|---|---|
| H | H |
| —C(=O)NCH2CH2OCH3 | H |
| 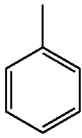 |  |
TABLE 47-continued
Formula XXXXVIII
| R⁷ᵇ | R¹¹ |
|---|---|
|  | 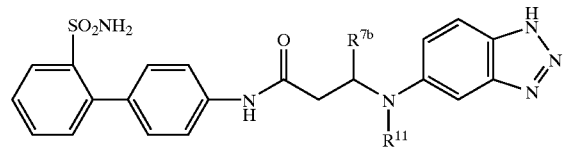 |
| 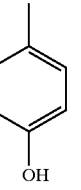 | 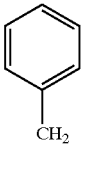 |
| 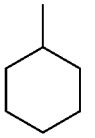 | 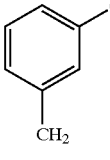 |
| —COOH | Me |
| —COOCH3 | Me |
| —C(=O)N(CH3)2 | Me |
TABLE 48
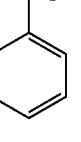
Formula XXXXIX
| R⁷ᵇ | R¹¹ |
|---|---|
| H | H |
| —C(=O)NCH2CH2OCH3 | H |
| 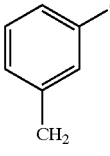 | 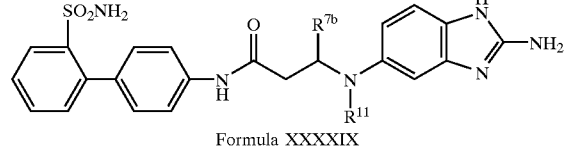 |
| 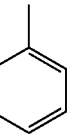 | 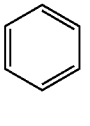 |

TABLE 48-continued

Formula XXXXIX: 2-amino-benzimidazole-substituted biphenyl sulfonamide with R7b and R11 substituents.

| R7b | R11 |
|---|---|
| cyclohexyl | 3-hydroxybenzyl (CH2-C6H4-OH) |
| benzyl (CH2-C6H5) | 3-methoxybenzyl (CH2-C6H4-OMe) |
| —COOH | Me |
| —COOCH3 | Me |
| —C(=O)N(CH3)2 | Me |

TABLE 49

Formula L

| R5 | R7 | R11 | R1b |
|---|---|---|---|
| H | H | H | H |
| Me | Me | H | H |
| 2-methylbenzyl | phenyl | Me | F |
| 4-pyridylmethyl (H2C-4-pyridyl) | 3-methylbenzyl (CH2-C6H4) | Bn | OH |
| cyclohexyl | 3-hydroxybenzyl (CH2-C6H4-OH) | 4-pyridylmethyl (H2C-4-pyridyl) | OMe |

TABLE 49-continued

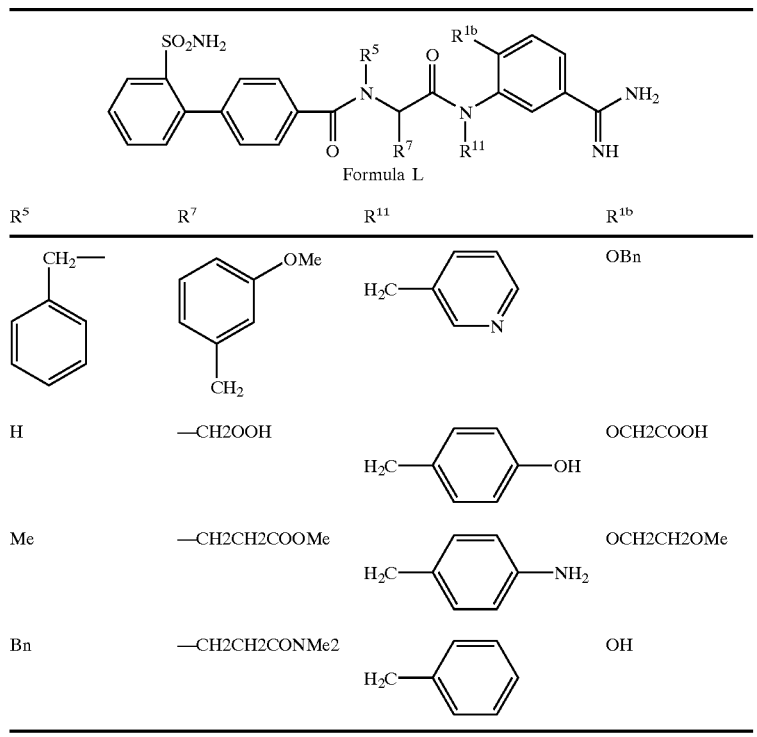

Formula L

| R⁵ | R⁷ | R¹¹ | R¹ᵇ |
|---|---|---|---|
| CH₂-Ph | 3-OMe-C₆H₄-CH₂ | 3-pyridyl-CH₂ | OBn |
| H | —CH2OOH | 4-HO-C₆H₄-CH₂ | OCH2COOH |
| Me | —CH2CH2COOMe | 4-H₂N-C₆H₄-CH₂ | OCH2CH2OMe |
| Bn | —CH2CH2CONMe2 | Ph-CH₂ | OH |

TABLE 50

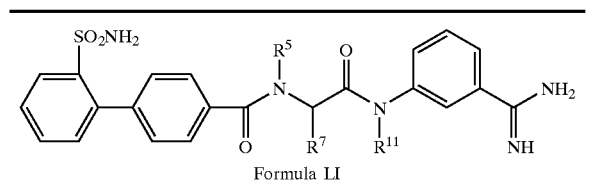

Formula LI

| R⁵ | R⁷ | R¹¹ |
|---|---|---|
| H | H | H |
| Me | Me | H |
| 4-Me-C₆H₄- | Ph | Me |
| 4-pyridyl-CH₂ | 3-HO-C₆H₄-CH₂ | Bn |
| cyclohexyl-CH₂ | 3-HO-C₆H₄-CH₂ | 4-pyridyl-CH₂ |

TABLE 50-continued

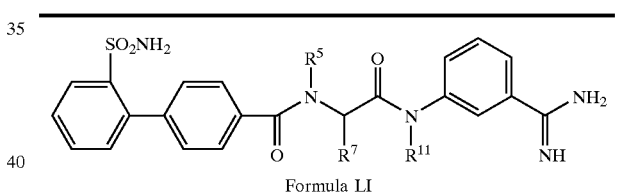

Formula LI

| R⁵ | R⁷ | R¹¹ |
|---|---|---|
| Ph-CH₂ | 3-OMe-C₆H₄-CH₂ | 3-pyridyl-CH₂ |
| H | —CH2OOH | 4-HO-C₆H₄-CH₂ |
| Me | —CH2CH2COOMe | 4-H₂N-C₆H₄-CH₂ |
| Bn | —CH2CH2CONMe2 | Ph-CH₂ |

TABLE 51

Formula LII: [2'-sulfamoylbiphenyl-4-carbonyl]-N(R5)-CH(R7)-C(O)-N(R11)-(1-aminoisoquinolin-7-yl)

| R⁵ | R⁷ | R¹¹ |
|---|---|---|
| H | H | H |
| Me | Me | H |
| 2-methylphenyl | phenyl | Me |
| 4-pyridylmethyl (H₂C-4-pyridyl) | 3-methylphenyl (benzyl-3-Me) | Bn |
| cyclohexyl | 3-hydroxybenzyl (H₂C-C₆H₄-3-OH) | 4-pyridylmethyl |
| benzyl (CH₂-Ph) | 3-methoxybenzyl (H₂C-C₆H₄-3-OMe) | 3-pyridylmethyl |
| H | —CH2OOH | 4-hydroxybenzyl (H₂C-C₆H₄-4-OH) |
| Me | —CH2CH2COOMe | 4-aminobenzyl (H₂C-C₆H₄-4-NH₂) |
| Bn | —CH2CH2CONMe2 | benzyl (H₂C-Ph) |

TABLE 52

Formula LIII: [2'-sulfamoylbiphenyl-4-carbonyl]-N(R5)-CH(R7)-C(O)-N(R11)-(3-amino-1H-indazol-5-yl)

| R⁵ | R⁷ | R¹¹ |
|---|---|---|
| H | H | H |
| Me | Me | H |

TABLE 52-continued

| R⁵ | R⁷ | R¹¹ |
|---|---|---|
|  |  | Me |
| 2-methylphenyl | phenyl |  |
| 4-pyridylmethyl | 3-methylbenzyl | Bn |
| cyclohexyl | 3-hydroxybenzyl | 4-pyridylmethyl |
| benzyl | 3-methoxybenzyl | 3-pyridylmethyl |
| H | —CH2OOH | 4-hydroxybenzyl |
| Me | —CH2CH2COOMe | 4-aminobenzyl |
| Bn | —CH2CH2CONMe2 | benzyl |

TABLE 53

Formula LIV: [2'-sulfamoylbiphenyl-4-carbonyl]-N(R5)-CH(R7)-C(O)-N(R11)-(3-aminobenzo[d]isothiazol-5-yl)

| R⁵ | R⁷ | R¹¹ |
|---|---|---|
| H | H | H |
| Me | Me | H |

TABLE 53-continued

Formula LIV: biphenyl-SO2NH2 with C(=O)-N(R5)-C(R7)-C(=O)-N(R11)-[benzisothiazole-3-amine]

| R⁵ | R⁷ | R¹¹ |
|---|---|---|
| phenyl (tolyl-CH attachment) | phenyl | Me |
| 4-pyridyl-CH2 | 3-methyl-benzyl (CH2-Ph-CH2) | Bn |
| cyclohexyl-CH | 3-hydroxybenzyl (CH2-Ph-OH) | 4-pyridyl-CH2 |
| benzyl (CH2-Ph) | 3-methoxybenzyl (CH2-Ph-OMe) | 3-pyridyl-CH2 |
| H | —CH2OOH | 4-hydroxybenzyl (H2C-Ph-OH) |
| Me | —CH2CH2COOMe | 4-aminobenzyl (H2C-Ph-NH2) |
| Bn | —CH2CH2CONMe2 | benzyl (H2C-Ph) |

TABLE 54

Formula LV: biphenyl-SO2NH2 with C(=O)-N(R5)-C(R7)-C(=O)-N(R11)-[benzisoxazole-3-amine]

| R⁵ | R⁷ | R¹¹ |
|---|---|---|
| H | H | H |
| Me | Me | H |

TABLE 54-continued

Formula LV: biphenyl-SO2NH2 with C(=O)-N(R5)-C(R7)-C(=O)-N(R11)-[benzisoxazole-3-amine]

| R⁵ | R⁷ | R¹¹ |
|---|---|---|
| phenyl (tolyl-CH attachment) | phenyl | Me |
| 4-pyridyl-CH2 | 3-methyl-benzyl | Bn |
| cyclohexyl-CH | 3-hydroxybenzyl | 4-pyridyl-CH2 |
| benzyl (CH2-Ph) | 3-methoxybenzyl | 3-pyridyl-CH2 |
| H | —CH2OOH | 4-hydroxybenzyl |
| Me | —CH2CH2COOMe | 4-aminobenzyl |
| Bn | —CH2CH2CONMe2 | benzyl |

TABLE 55

Formula LVI: biphenyl-SO2NH2 with C(=O)-N(R5)-C(R7)-C(=O)-N(R11)-[benzotriazole]

| R⁵ | R⁷ | R¹¹ |
|---|---|---|
| H | H | H |
| Me | Me | H |

TABLE 55-continued
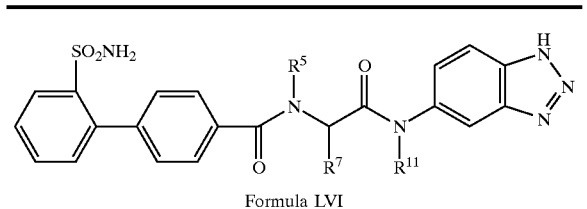
Formula LVI
| R⁵ | R⁷ | R¹¹ |
|---|---|---|
|  |  | Me |
| 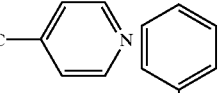 |  | Bn |
|  | 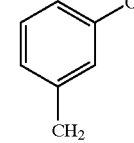 | 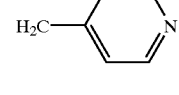 |
| 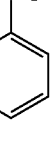 | 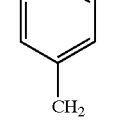 | 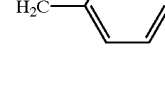 |
| H | —CH2OOH | 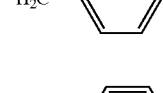 |
| Me | —CH2CH2COOMe | 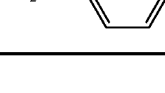 |
| Bn | —CH2CH2CONMe2 |  |
TABLE 56
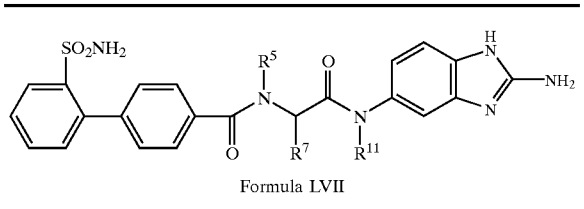
Formula LVII
| R⁵ | R⁷ | R¹¹ |
|---|---|---|
| H | H | H |
| Me | Me | H |
|  |  | Me |
|  |  | Bn |
|  |  |  |
|  |  |  |
| H | —CH2OOH |  |
| Me | —CH2CH2COOMe |  |
| Bn | —CH2CH2CONMe2 |  |

TABLE 57

Formula LVIII

| R⁵ | R⁷ᵃ | R¹¹ | R¹ᵇ |
|---|---|---|---|
| H | H | H | H |
| Me | Me | H | H |
| 2-methylphenyl-CH₂ | phenyl | Me | F |
| 4-pyridyl-CH₂ | 3-methylphenyl-CH₂ | Bn | OH |
| cyclohexyl | 3-hydroxyphenyl-CH₂ | 4-pyridyl-CH₂ | OMe |
| benzyl (CH₂-Ph) | 3-methoxyphenyl-CH₂ | 3-pyridyl-CH₂ | OBn |
| H | —CH2OOH | 4-hydroxyphenyl-CH₂ | OCH2COOH |
| Me | —CH2CH2COOMe | 4-aminophenyl-CH₂ | OCH2CH2OMe |
| Bn | —CH2CH2CONMe2 | benzyl-CH₂ | OH |

TABLE 58

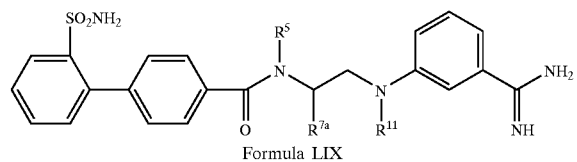

Formula LIX

| R⁵ | R⁷ᵃ | R¹¹ |
|---|---|---|
| H | H | H |

TABLE 58-continued

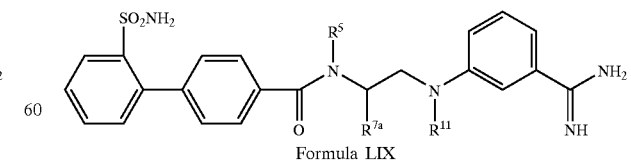

Formula LIX

| R⁵ | R⁷ᵃ | R¹¹ |
|---|---|---|
| Me | Me | H |

TABLE 58-continued
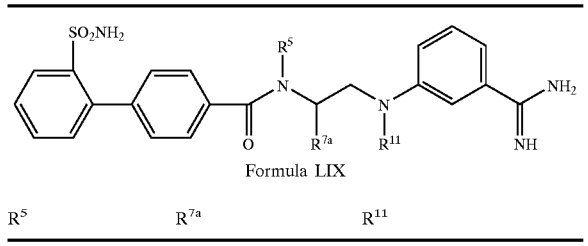
Formula LIX
| R⁵ | R⁷ᵃ | R¹¹ |
|---|---|---|
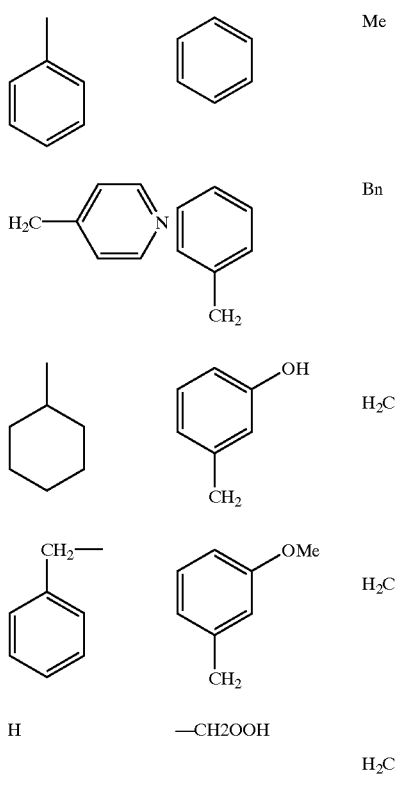
TABLE 59
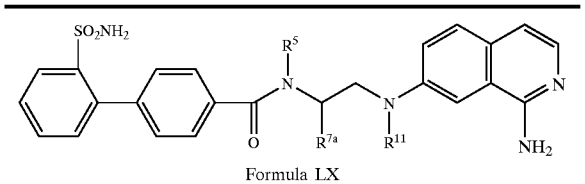
Formula LX
| R⁵ | R⁷ᵃ | R¹¹ |
|---|---|---|
| H | H | H |
| Me | Me | H |
TABLE 59-continued
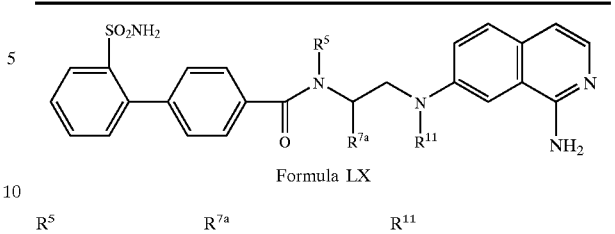
Formula LX
| R⁵ | R⁷ᵃ | R¹¹ |
|---|---|---|
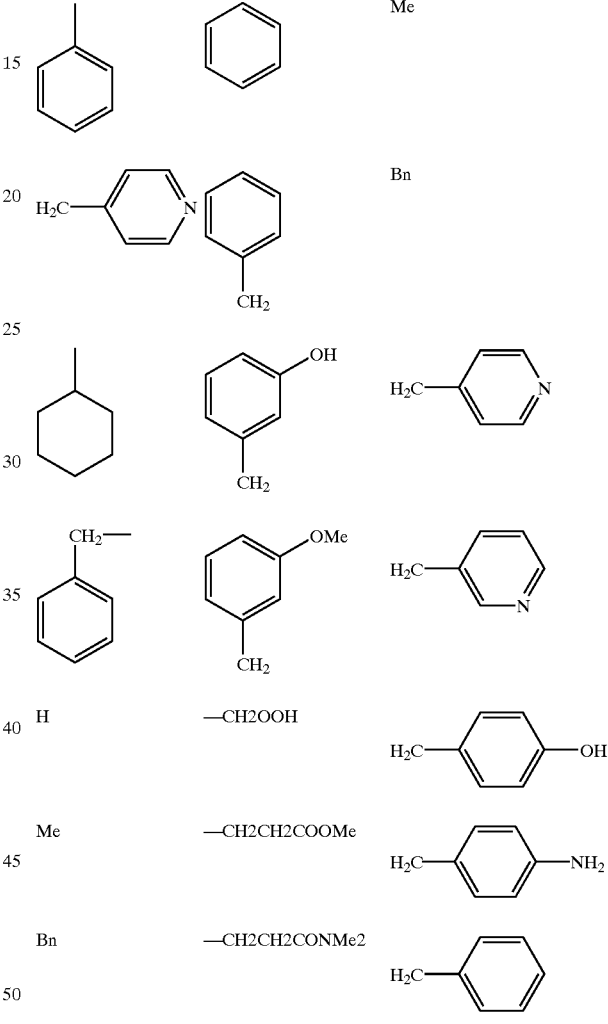
TABLE 60
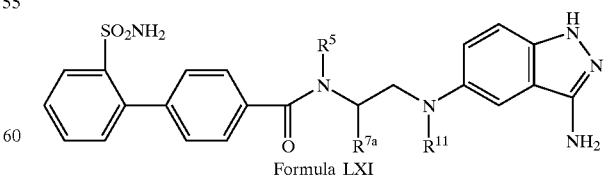
Formula LXI
| R⁵ | R⁷ᵃ | R¹¹ |
|---|---|---|
| H | H | H |
| Me | Me | H |

TABLE 60-continued

Formula LXI: 2-sulfamoyl-biphenyl-4-carboxamide with N(R⁵)–C(R⁷ᵃ)H–CH₂–N(R¹¹)–[1H-indazol-5-yl]-3-amine

| R⁵ | R⁷ᵃ | R¹¹ |
|---|---|---|
| (o-tolyl-CH—) | phenyl | Me |
| 4-pyridyl-CH₂— | 3-(phenyl-CH₂)-phenyl | Bn |
| cyclohexyl-CH— | 3-hydroxy-phenyl-CH₂— | 4-pyridyl-CH₂— |
| benzyl (PhCH₂—) | 3-methoxy-phenyl-CH₂— | 3-pyridyl-CH₂— |
| H | —CH2OOH | 4-hydroxy-phenyl-CH₂— |
| Me | —CH2CH2COOMe | 4-amino-phenyl-CH₂— |
| Bn | —CH2CH2CONMe2 | phenyl-CH₂— |

TABLE 61

Formula LXII: 2-sulfamoyl-biphenyl-4-carboxamide with N(R⁵)–C(R⁷ᵃ)H–CH₂–N(R¹¹)–[benzo[d]isothiazol-5-yl]-3-amine

| R⁵ | R⁷ᵃ | R¹¹ |
|---|---|---|
| H | H | H |
| Me | Me | H |

TABLE 61-continued

Formula LXII: 2-sulfamoyl-biphenyl-4-carboxamide with N(R⁵)–C(R⁷ᵃ)H–CH₂–N(R¹¹)–[benzo[d]isothiazol-5-yl]-3-amine

| R⁵ | R⁷ᵃ | R¹¹ |
|---|---|---|
| (o-tolyl-CH—) | phenyl | Me |
| 4-pyridyl-CH₂— | 3-(phenyl-CH₂)-phenyl | Bn |
| cyclohexyl-CH— | 3-hydroxy-phenyl-CH₂— | 4-pyridyl-CH₂— |
| benzyl (PhCH₂—) | 3-methoxy-phenyl-CH₂— | 3-pyridyl-CH₂— |
| H | —CH2OOH | 4-hydroxy-phenyl-CH₂— |
| Me | —CH2CH2COOMe | 4-amino-phenyl-CH₂— |
| Bn | —CH2CH2CONMe2 | phenyl-CH₂— |

TABLE 62

Formula LXIII: 2-sulfamoyl-biphenyl-4-carboxamide with N(R⁵)–C(R⁷ᵃ)H–CH₂–N(R¹¹)–[benzo[d]isoxazol-5-yl]-3-amine

| R⁵ | R⁷ᵃ | R¹¹ |
|---|---|---|
| H | H | H |
| Me | Me | H |

TABLE 62-continued
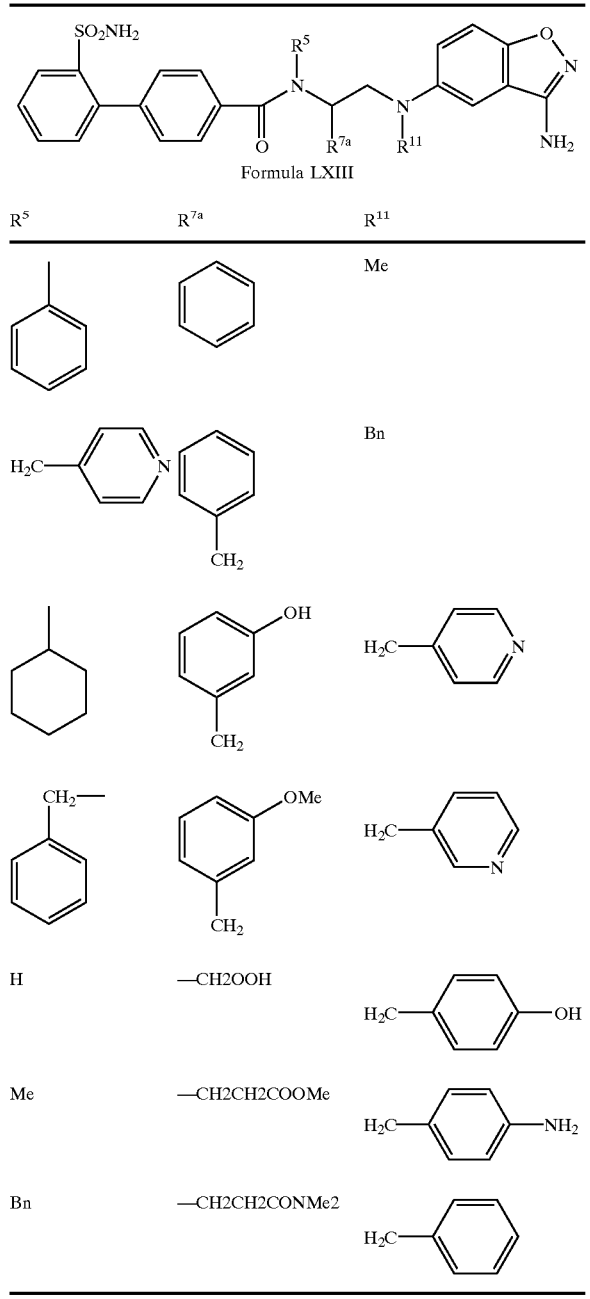
TABLE 63
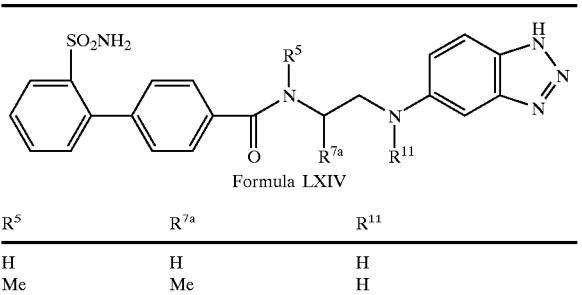
| R[5] | R[7a] | R[11] |
|---|---|---|
| H | H | H |
| Me | Me | H |
TABLE 63-continued
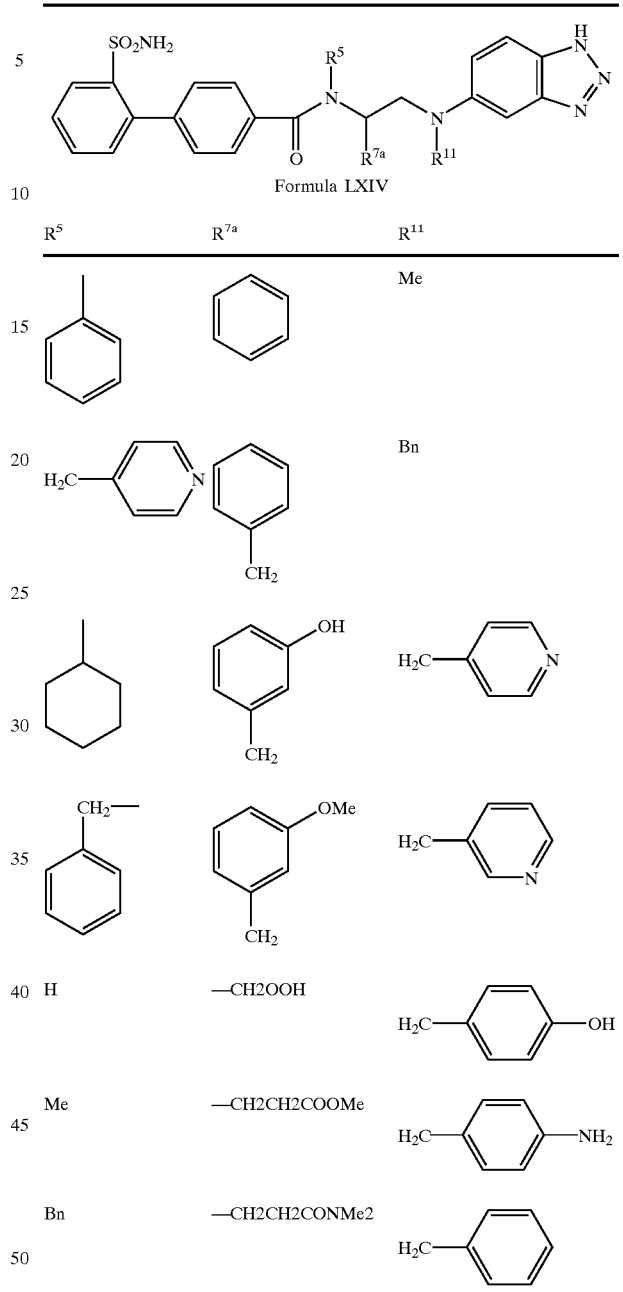
TABLE 64
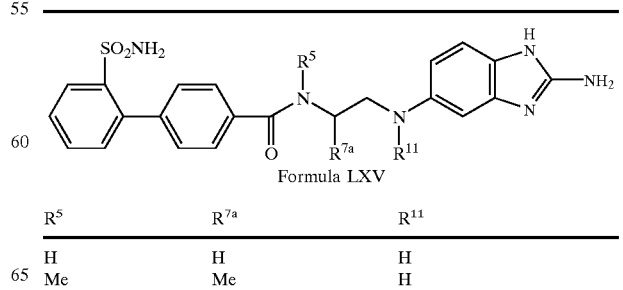
| R[5] | R[7a] | R[11] |
|---|---|---|
| H | H | H |
| Me | Me | H |

TABLE 64-continued

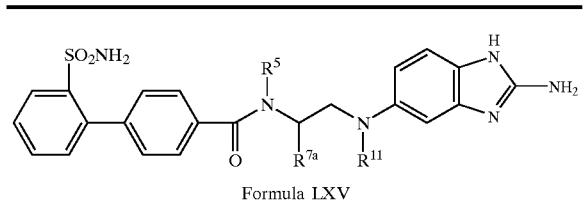

Formula LXV

| R⁵ | R⁷ᵃ | R¹¹ |
|---|---|---|
| (o-tolyl) | (phenyl) | Me |
| (4-pyridylmethyl) | (3-methylphenyl) | Bn |
| (cyclohexyl/methylcyclohexyl) | (3-hydroxybenzyl) | (4-pyridylmethyl) |

TABLE 64-continued

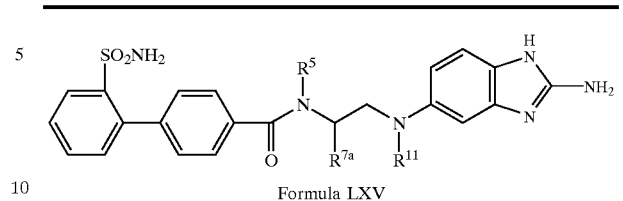

Formula LXV

| R⁵ | R⁷ᵃ | R¹¹ |
|---|---|---|
| (benzyl) | (3-methoxybenzyl) | (3-pyridylmethyl) |
| H | —CH2OOH | (4-hydroxybenzyl) |
| Me | —CH2CH2COOMe | (4-aminobenzyl) |
| Bn | —CH2CH2CONMe2 | (benzyl) |

TABLE 65

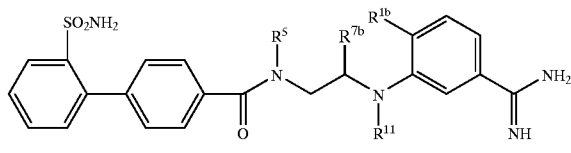

Formula LXVI

| R⁵ | R⁷ᵇ | R¹¹ | R¹ᵇ |
|---|---|---|---|
| H | H | H | H |
| Me | Me | H | H |
| (o-tolyl) | (phenyl) | Me | F |
| (4-pyridylmethyl) | (3-methylbenzyl) | Bn | OH |

TABLE 65-continued

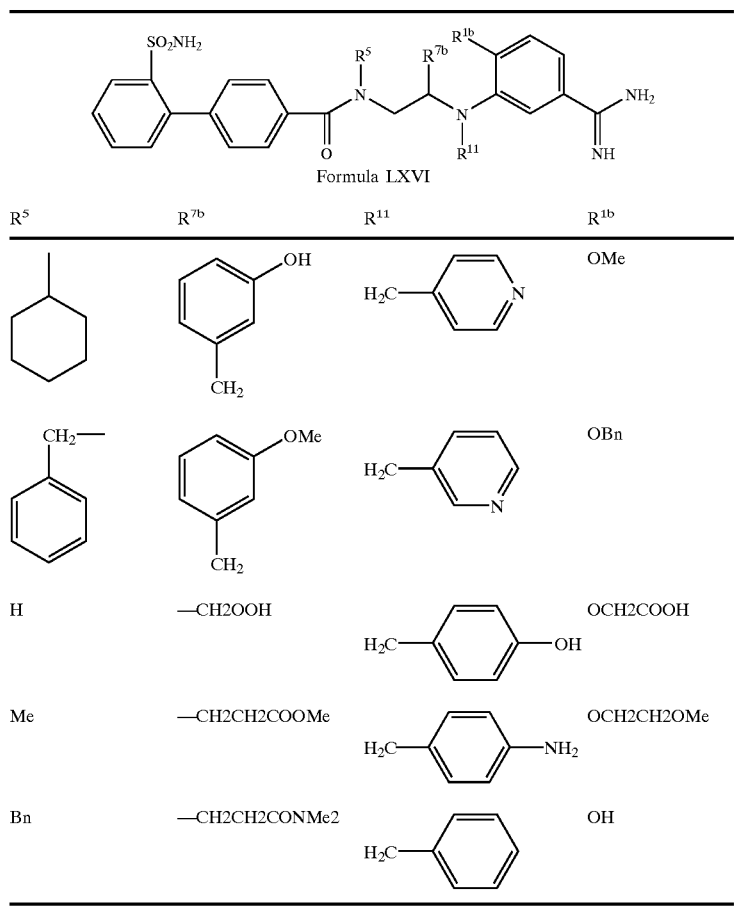

Formula LXVI

| R⁵ | R⁷ᵇ | R¹¹ | R¹ᵇ |
|---|---|---|---|
| cyclohexyl | 3-hydroxybenzyl | 4-pyridylmethyl | OMe |
| Bn (CH₂-phenyl) | 3-methoxybenzyl | 3-pyridylmethyl | OBn |
| H | —CH2OOH | 4-hydroxybenzyl | OCH2COOH |
| Me | —CH2CH2COOMe | 4-aminobenzyl | OCH2CH2OMe |
| Bn | —CH2CH2CONMe2 | benzyl | OH |

TABLE 66

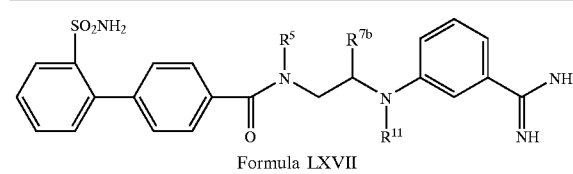

Formula LXVII

| R⁵ | R⁷ᵇ | R¹¹ |
|---|---|---|
| H | H | H |
| Me | Me | H |
| 4-methylphenyl | phenyl | Me |
| 4-pyridylmethyl | 3-methylphenyl | Bn |

TABLE 66-continued

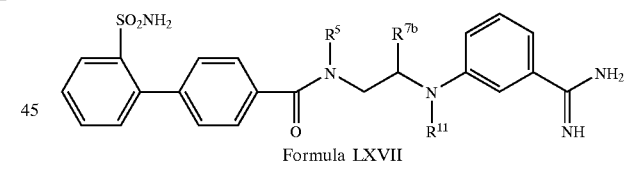

Formula LXVII

| R⁵ | R⁷ᵇ | R¹¹ |
|---|---|---|
| cyclohexyl | 3-hydroxybenzyl | 4-pyridylmethyl |
| Bn (CH₂-phenyl) | 3-methoxybenzyl | 3-pyridylmethyl |
| H | —CH2OOH | 4-hydroxybenzyl |

TABLE 66-continued

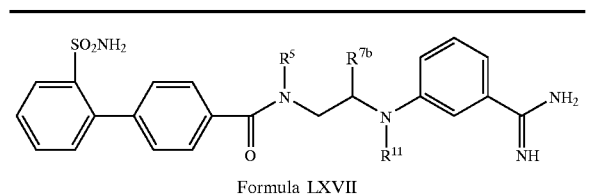

Formula LXVII

| R⁵ | R⁷ᵇ | R¹¹ |
|---|---|---|
| Me | —CH2CH2COOMe | 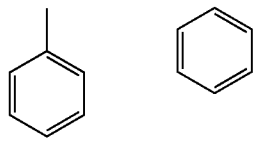 |
| Bn | —CH2CH2CONMe2 | (benzyl) |

TABLE 67

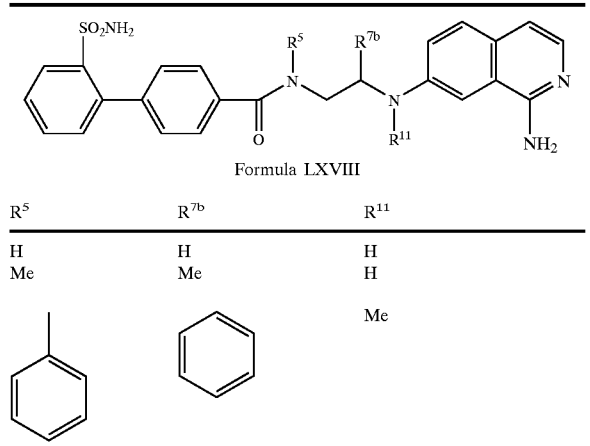

Formula LXVIII

| R⁵ | R⁷ᵇ | R¹¹ |
|---|---|---|
| H | H | H |
| Me | Me | H |
| (tolyl) | (phenyl) | Me |

TABLE 67-continued

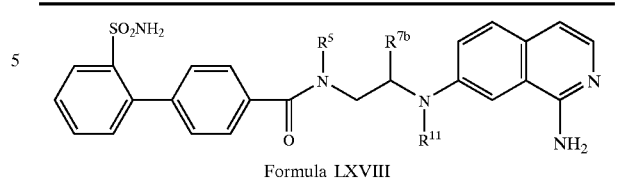

Formula LXVIII

| R⁵ | R⁷ᵇ | R¹¹ |
|---|---|---|
| 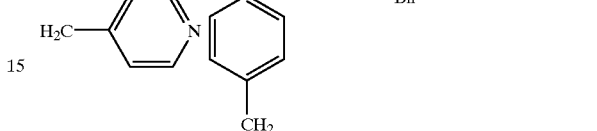 (4-pyridylmethyl) | (3-tolyl) | Bn |
| (cyclohexyl) | 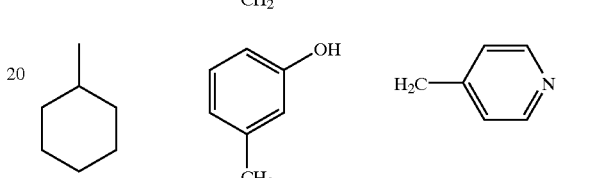 (3-hydroxybenzyl) | (4-pyridylmethyl) |
| (benzyl) | 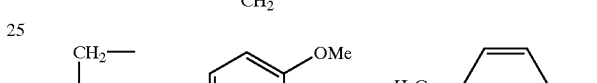 (3-methoxybenzyl) | (3-pyridylmethyl) |
| H | —CH2OOH | (4-hydroxybenzyl) |
| Me | —CH2CH2COOMe | (4-aminobenzyl) |
| Bn | —CH2CH2CONMe2 | (benzyl) |

TABLE 68

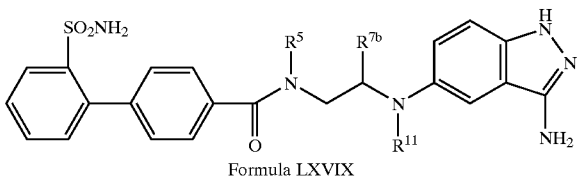

Formula LXVIX

| R⁵ | R⁷ᵇ | R¹¹ |
|---|---|---|
| H | H | H |
| Me | Me | H |
| 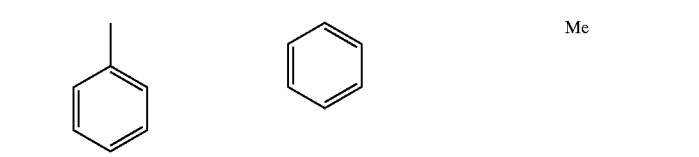 (tolyl) | (phenyl) | Me |

TABLE 68-continued
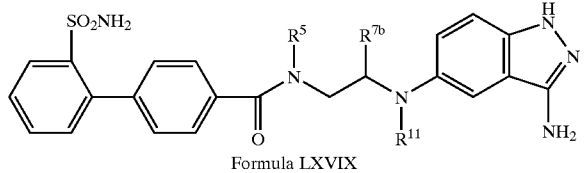
Formula LXVIX
| R⁵ | R⁷ᵇ | R¹¹ |
|---|---|---|
| 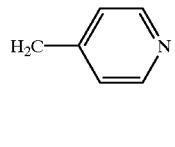 | 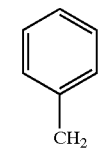 | Bn |
|  | 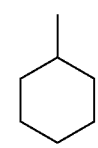 | 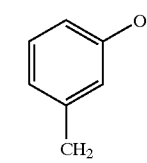 |
| 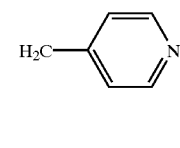 | 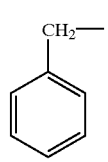 | 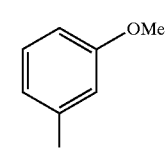 |
| H | —CH2OOH | 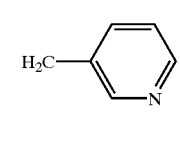 |
| Me | —CH2CH2COOMe | 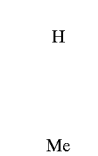 |
| Bn | —CH2CH2CONMe2 | 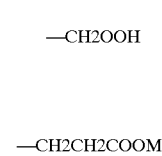 |
TABLE 69
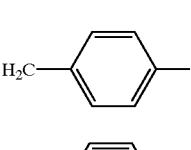
Formula LXX
| R⁵ | R⁷ᵇ | R¹¹ |
|---|---|---|
| H | H | H |
| Me | Me | H |
| 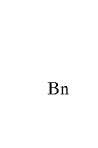 | 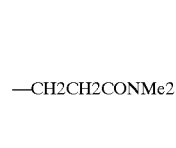 | Me |

TABLE 69-continued

Formula LXX: biphenyl with SO₂NH₂ substituent, connected via C(=O)-N(R⁵)-CH₂-CH(R⁷ᵇ)-N(R¹¹)- to 3-amino-benzisothiazol-5-yl

| R⁵ | R⁷ᵇ | R¹¹ |
|---|---|---|
| 4-pyridylmethyl (H₂C-4-pyridyl) | benzyl (PhCH₂) | Bn |
| cyclohexylmethyl | 3-hydroxybenzyl | 4-pyridylmethyl |
| benzyl (CH₂-Ph) | 3-methoxybenzyl | 3-pyridylmethyl |
| H | —CH2OOH | 4-hydroxybenzyl |
| Me | —CH2CH2COOMe | 4-aminobenzyl |
| Bn | —CH2CH2CONMe2 | benzyl (H₂C-Ph) |

TABLE 70

Formula LXXI: biphenyl with SO₂NH₂ substituent, connected via C(=O)-N(R⁵)-CH₂-CH(R⁷ᵇ)-N(R¹¹)- to 3-amino-benzisoxazol-5-yl

| R⁵ | R⁷ᵇ | R¹¹ |
|---|---|---|
| H | H | H |
| Me | Me | H |
| | 4-methylcyclohexa-1,3-dienyl | Me |
| | phenyl | |

TABLE 70-continued
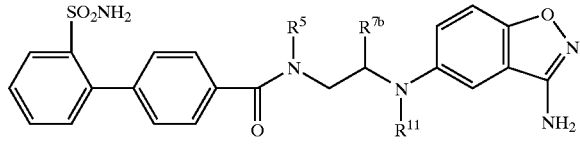
Formula LXXI
| R⁵ | R⁷ᵇ | R¹¹ |
|---|---|---|
| 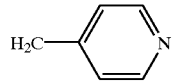 | 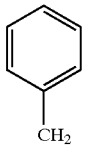 | Bn |
|  | 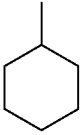 | 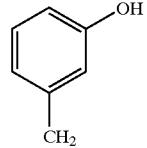 |
| 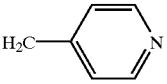 | 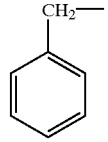 | 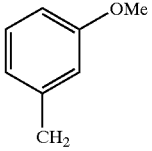 |
| H | —CH2OOH | 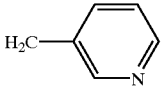 |
| Me | —CH2CH2COOMe |  |
| Bn | —CH2CH2CONMe2 | 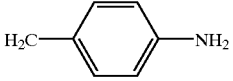 |
TABLE 71
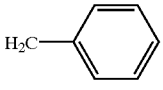
Formula LXXII
| R⁵ | R⁷ᵇ | R¹¹ |
|---|---|---|
| H | H | H |
| Me | Me | H |
| 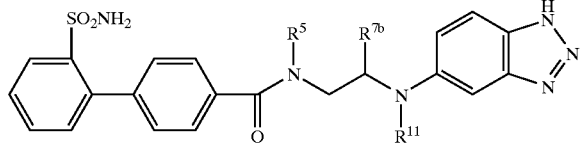 | 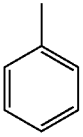 | Me |

TABLE 71-continued
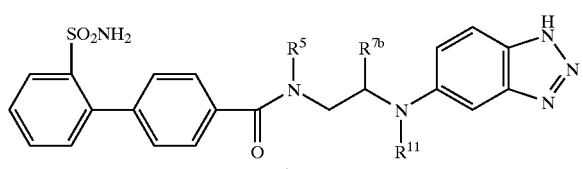
Formula LXXII
| R[5] | R[7b] | R[11] |
|---|---|---|
| 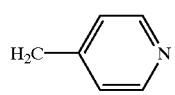 | 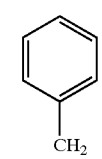 | Bn |
| 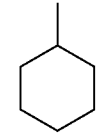 | 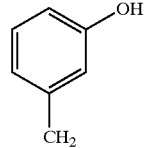 | 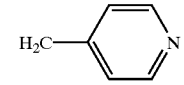 |
| 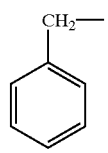 | 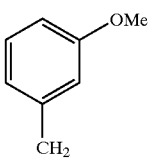 | 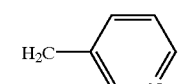 |
| H | —CH2OOH | 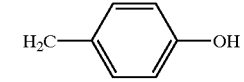 |
| Me | —CH2CH2COOMe | 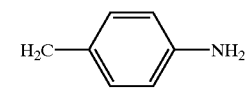 |
| Bn | —CH2CH2CONMe2 | 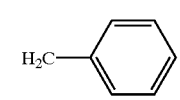 |
TABLE 72
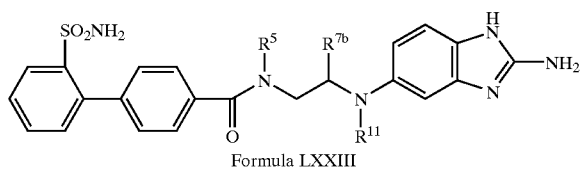
Formula LXXIII
| R[5] | R[7b] | R[11] |
|---|---|---|
| H | H | H |
| Me | Me | H |
| 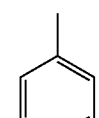 | 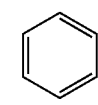 | Me |

TABLE 72-continued

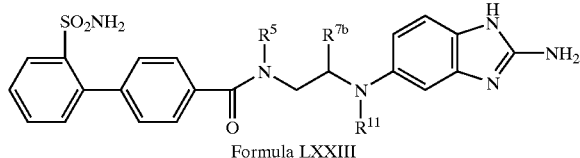

Formula LXXIII

| R⁵ | R⁷ᵇ | R¹¹ |
|---|---|---|
| 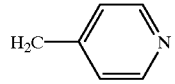 |  | Bn |
| 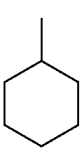 | 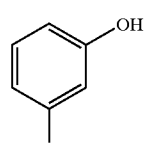 |  |
| 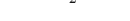 | 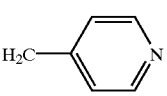 | 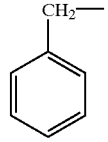 |
| H | —CH2OOH | 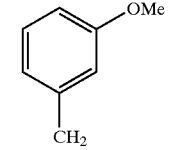 |
| Me | —CH2CH2COOMe |  |
| Bn | —CH2CH2CONMe2 | 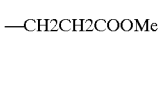 |
| | | 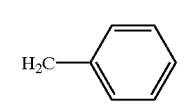 |

This invention also encompasses all pharmaceutically acceptable isomers, salts, hydrates and solvates of the compounds of formulas I, II and III. In addition, the compounds of formulas I, II and III can exist in various isomeric and tautomeric forms, and all such forms are meant to be included in the invention, along with pharmaceutically acceptable salts, hydrates and solvates of such isomers and tautomers.

The compounds of this invention may be isolated as the free acid or base or converted to salts of various inorganic and organic acids hand bases. Such salts are within the scope of this invention. Non-toxic and physiologically compatible salts are particularly useful although other less desirable salts may have use in the processes of isolation and purification.

A number of methods are useful for the preparation of the salts described above and are known to those skilled in the art. For example, the free acid or free base form of a compound of one of the formulas above can be reacted with one or more molar equivalents of the desired acid or base in a solvent or solvent mixture in which the salt is insoluble, or in a solvent like water after which the solvent is removed by evaporation, distillation or freeze drying. Alternatively, the free acid or base form of the product may be passed over an ion exchange resin to form the desired salt or one salt form of the product may be converted to another using the same general process.

Prodrug Derivatives of Compounds

This invention also encompasses prodrug derivatives of the compounds contained herein. The term "prodrug" refers to a pharmacologically inactive derivative of a parent drug molecule that requires biotransfornation, either spontaneous or enzymatic, within the organism to release the active drug. Prodrugs are variations or derivatives of the compounds of this invention which have groups cleavable under metabolic conditions. Prodrugs become the compounds of the invention which are pharmaceutically active in vivo, when they undergo solvolysis under physiological conditions or undergo enzymatic degradation. Prodrug compounds of this invention may be called single, double, triple etc., depending on the number of biotransformation steps required to release the active drug within the organism, and indicating the number of fanctionalities present in a precursor-type form. Prodrug forms often offer advantages of solubility, tissue compatibility, or delayed release in the mammalian organism (see, Bundgard, Design of Prodrugs, pp. 7–9, 21–24, Elsevier, Amsterdam 1985 and Silverman, The Organic Chemistry of Drug Design and Drug Action, pp. 352–401, Academic Press, San Diego, Calif., 1992). Prodrugs commonly known in the art include acid derivatives well known to practitioners of the art, such as, for example, esters prepared by reaction of the parent acids with a suitable alcohol, or amides prepared by reaction of the parent acid compound with an amine, or basic groups reacted to form an acylated base derivative. Moreover, the prodrug derivatives of this invention may be combined with other features herein taught to enhance bioavailability.

As mentioned above, the compounds of this invention find utility as therapeutic agents for disease states in mammals which have disorders of coagulation such as in the treatment or prevention of unstable angina, refractory angina, myocardial infarction, transient ischemic attacks, thrombotic stroke, embolic stroke, disseminated intravascular coagulation including the treatment of septic shock, deep venous thrombosis in the prevention of pulmonary embolism or the treatment of reocclusion or restenosis of reperfused coronary arteries. Further, these compounds are useful for the treatment or prophylaxis of those diseases which involve the production and/or action of factor Xa/prothrombinase complex. This includes a number of thrombotic and prothrombotic states in which the coagulation cascade is activated which include but are not limited to, deep venous thrombosis, pulmonary embolism, myocardial infarction, stroke, thromboembolic complications of surgery and peripheral arterial occlusion.

Accordingly, a method for preventing or treating a condition in a mammal characterized by undesired thrombosis comprises administering to the mammal a therapeutically effective amount of a compound of this invention. In addition to the disease states noted above, other diseases treatable or preventable by the administration of compounds of this invention include, without limitation,: occlusive coronary thrombus formation resulting from either thrombolytic therapy or percutaneous transluminal coronary angioplasty, thrombus formation in the venous vasculature, disseminated intravascular coagulopathy, a condition wherein there is rapid consumption of coagulation factors and systemic coagulation which results in the formation of life-threatening thrombi occurring throughout the microvasculature leading to widespread organ failure, hemorrhagic stroke, renal dialysis, blood oxygenation, and cardiac catheterization.

The compounds of the invention also find utility in a method for inhibiting the coagulation biological samples, which comprises the administration of a compound of the invention.

The compounds of the present invention may also be used in combination with other therapeutic or diagnostic agents. In certain preferred embodiments, the compounds of this invention may be coadministered along with other compounds typically.prescribed for these conditions according to generally accepted medical practice such as anticoagulant agents, thrombolytic agents, or other antithrombotics, including platelet aggregation inhibitors, tissue plasminogen activators, urokinase, prourokinase, streptokinase, heparin, aspirin, or warfarin. The compounds of the present invention may act in a synergistic fashion to prevent reocclusion following a successful thrombolytic therapy and/or reduce the time to reperfusion. These compounds may also allow for reduced doses of the thrombolytic agents to be used and therefore minimize potential hemorrhagic side-effects. The compounds of this invention can be utilized in vivo, ordinarily in mammals such as primates, (e.g. humans), sheep, horses, cattle, pigs, dogs, cats, rats and mice, or in vitro.

The biological properties of the compounds of the present invention can be readily characterized by methods that are well known in the art, for example by the in vitro protease activity assays and in vivo studies to evaluate antithrombotic efficacy, and effects on hemostasis and hematological parameters, such as are illustrated in the examples.

Diagnostic applications of the compounds of this invention will typically utilize formulations in the form of solutions or suspensions. In the management of thrombotic disorders the compounds of this invention may be utilized in compositions such as tablets, capsules or elixirs for oral administration, suppositories, sterile solutions or suspensions or injectable administration, and the like, or incorporated into shaped articles. Subjects in need of treatment (typically mammalian) using the compounds of this invention can be administered dosages that will provide optimal efficacy. The dose and method of administration will vary from subject to subject and be dependent upon such factors as the type of mammal being treated, its sex, weight, diet, concurrent medication, overall clinical condition, the particular compounds employed, the specific use for which these compounds are employed, and other factors which those skilled in the medical arts will recognize.

Formulations of the compounds of this invention are prepared for storage or administration by mixing the compound having a desired degree of purity with physiologically acceptable carriers, excipients, stabilizers etc., and may be provided in sustained release or timed release formulations. Acceptable carriers or diluents for therapeutic use are well known in the pharmaceutical field, and are described, for example, in Remington's Pharmaceutical Sciences, Mack Publishing Co., (A. R. Gennaro edit. 1985). Such materials are nontoxic to the recipients at the dosages and concentrations employed, and include buffers such as phosphate, citrate, acetate and other organic acid salts, antioxidants such as ascorbic acid, low molecular weight (less than about ten residues) peptides such as polyarginine, proteins, such as serum albumin, gelatin, or immunoglobulins, hydrophilic polymers such as polyvinylpyrrolidinone, amino acids such as glycine, glutamic acid, aspartic acid, or arginine, monosaccharides, disaccharides, and other carbohydrates including cellulose or its derivatives, glucose, mannose or dextrins, chelating agents such as EDTA, sugar alcohols such as mannitol or sorbitol, counterions such as sodium and/or nonionic surfactants such as Tween, Pluronics or polyethyleneglycol.

Dosage formulations of the compounds of this invention to be used for therapeutic administration must be sterile. Sterility is readily accomplished by filtration through sterile membranes such as 0.2 micron membranes, or by other conventional methods. Formulations typically will be stored in lyophilized form or as an aqueous solution. The pH of the preparations of this invention typically will be 3–11, more preferably 5–9 and most preferably 7–8. It will be understood that use of certain of the foregoing excipients, carriers, or stabilizers will result in the formation of cyclic polypeptide salts. While the preferred route of administration is by injection, other methods of administration are also anticipated such as orally, intravenously (bolus and/or infusion), subcutaneously, intramuscularly, colonically, rectally, nasally, transdermally or intraperitoneally, employing a variety of dosage forms such as suppositories, implanted pellets or small cylinders, aerosols, oral dosage formulations and topical formulations such as ointments, drops and dermal patches. The compounds of this invention are desirably incorporated into shaped articles such as implants which may employ inert materials such as biodegradable polymers or synthetic silicones, for example, Silastic, silicone rubber or other polymers commercially available.

The compounds of the invention may also be administered in the form of liposome delivery systems, such as small unilamellar vesicles, large unilamellar vesicles and multilamellar vesicles. Liposomes can be formed from a variety of lipids, such as cholesterol, stearylamine or phosphatidylcholines.

The compounds of this invention may also be delivered by the use of antibodies, antibody fragments, growth factors, hormones, or other targeting moieties, to which the compound molecules are coupled. The compounds of this invention may also be coupled with suitable polymers as targetable drug carriers. Such polymers can include polyvinylpyrrolidinone, pyran copolymer, polyhydroxypropyl-methacrylamide-phenol, polyhydroxyethyl-aspartamide-phenol, or polyethyleneoxide-polylysine substituted with palmitoyl residues. Furthermore, compounds of the invention may be coupled to a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like.

Therapeutic compound liquid formulations generally are placed into a container having a sterile access port, for example, an intravenous solution bag or vial having a stopper pierceable by hypodermic injection needle.

Therapeutically effective dosages may be determined by either in vitro or in vivo methods. For each particular compound of the present invention, individual determinations may be made to determine the optimal dosage required. The range of therapeutically effective dosages will be influenced by the route of administration, the therapeutic objectives and the condition of the patient. For injection by hypodermic needle, it may be assumed the dosage is delivered into the body's fluids. For other routes of administration, the absorption efficiency must be individually determined for each compound by methods well known in pharmacology. Accordingly, it may be necessary for the therapist to titer the dosage and modify the route of administration as required to obtain the optimal therapeutic effect. The determination of effective dosage levels, that is, the dosage levels necessary to achieve the desired result, will be readily determined by one skilled in the art. Typically, applications of compound are commenced at lower dosage levels, with dosage levels being increased until the desired effect is achieved.

The compounds of the invention can be administered orally or parenterally in an effective amount within the dosage range of about 0.1 to 100 mg/kg, preferably about 0.5 to 50 mg/kg and more preferably about 1 to 20 mg/kg on a regimen in a single or 2 to 4 divided daily doses and/or continuous infusion.

Typically, about 5 to 500 mg of a compound or mixture of compounds of this invention, as the free acid or base form or as a pharmaceutically acceptable salt, is compounded with a physiologically acceptable vehicle, carrier, excipient, binder, preservative, stabilizer, dye, flavor etc., as called for by accepted pharmaceutical practice. The amount of active ingredient in these compositions is such that a suitable dosage in the range indicated is obtained.

Typical adjuvants which may be incorporated into tablets, capsules and the like are binders such as acacia, corn starch or gelatin, and excipients such as microcrystalline cellulose, disintegrating agents like corn starch or aiginic acid, lubricants such as magnesium stearate, sweetening agents such as sucrose or lactose, or flavoring agents. When a dosage form is a capsule, in addition to the above materials it may also contain liquid carriers such as water, saline, or a fatty oil. Other materials of various types may be used as coatings or as modifiers of the physical form of the dosage unit. Sterile compositions for injection can be formulated according to conventional pharmaceutical practice. For example, dissolution or suspension of the active compound in a vehicle such as an oil or a synthetic fatty vehicle like ethyl oleate, or into a liposome may be desired. Buffers, preservatives, antioxidants and the like can be incorporated according to accepted pharmaceutical practice.

Preparation of Compounds

The compounds of the present invention may be synthesized by either solid or liquid phase methods described and referenced in standard textbooks, dr by a combination of both methods. These methods are well known in the art. See, Bodanszky, "The Principles of Peptide Synthesis", Hafnler, et al., Eds., Springer-Verlag, Berlin, 1984.

Starting materials used in any of these methods are commercially available from chemical vendors such as Aldrich, Sigma, Nova Biochemicals, Bachem Biosciences, and the like, or may be readily synthesized by known procedures.

Reactions are carried out in standard laboratory glassware and reaction vessels under reaction conditions of standard temperature and pressure, except where otherwise indicated.

During the synthesis of these compounds, the functional groups of the amino acid derivatives used in these methods are protected by blocking groups to prevent cross reaction during the coupling procedure. Examples of suitable blocking groups and their use are described in "The Peptides: Analysis, Synthesis, Biology"., Academic Press, Vol. 3 (Gross, et al., Eds., 1981) and Vol. 9 (1987), the disclosures of which are incorporated herein by reference.

Non-limiting exemplary synthesis schemes are outlined directly below, and specific steps are described in the Examples. The reaction products are isolated and purified by conventional methods, typically by solvent extraction into a compatible solvent. The products may be further purified by column chromatography or other appropriate methods.

Scheme 1

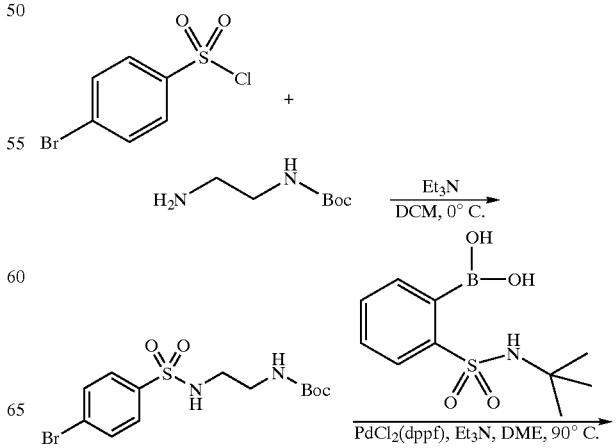

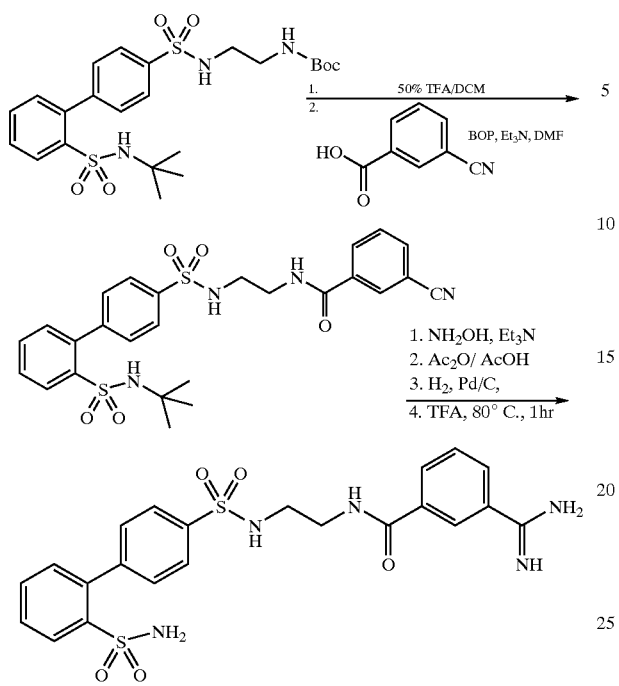

Scheme 2

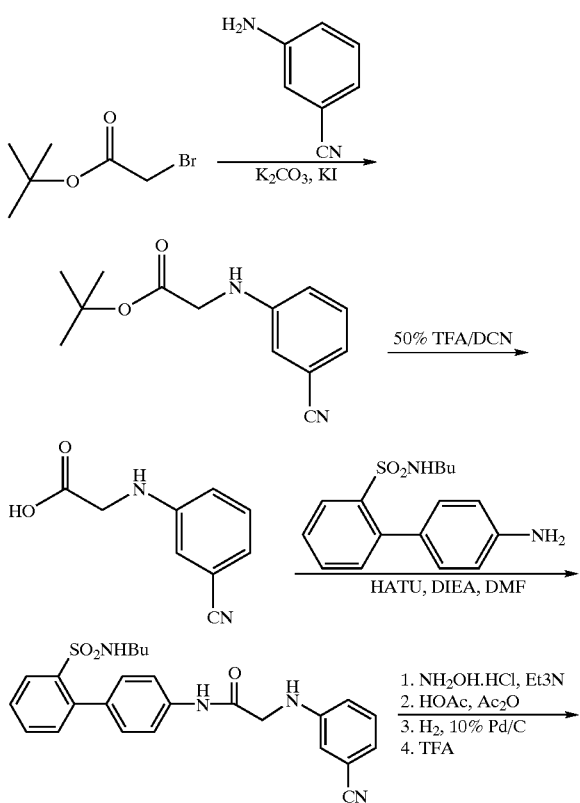

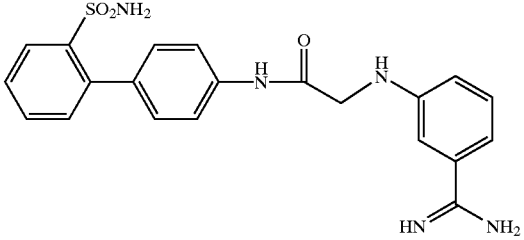

Compositions and Formulations

The compounds of this invention may be isolated as the free acid or base or converted to salts of various inorganic and organic acids and bases. Such salts are within the scope of this invention. Non-toxic and physiologically compatible salts are particularly useful although other less desirable salts may have use in the processes of isolation and purification.

A number of methods are useful for the preparation of the salts described above and are known to those skilled in the art. For example, reaction of the free acid or free base form of a compound of the structures recited above with one or more molar equivalents of the desired acid or base in a solvent or solvent mixture in which the salt is insoluble, or in a solvent like water after which the solvent is removed by evaporation, distillation or freeze drying. Alternatively, the free acid or base form of the product may be passed over an ion exchange resin to form the desired salt or one salt form of the product may be converted to another using the same general process.

Diagnostic applications of the compounds of this invention will typically utilize formulations such as solution or suspension. In the management of thrombotic disorders the compounds of this invention may be utilized in compositions such as tablets, capsules or elixirs for oral administration, suppositories, sterile solutions or suspensions or injectable administration, and the like, or incorporated into shaped articles. Subjects in need of treatment (typically mammalian) using the compounds of this invention can be administered dosages that will provide optimal efficacy. The dose and method of administration will vary from subject to subject and be dependent upon such factors as the type of mammal being treated, its sex, weight, diet, concurrent medication, overall clinical condition, the particular compounds employed, the specific use for which these compounds are employed, and other factors which those skilled in the medical arts will recognize.

Formulations of the compounds of this invention are prepared for storage or administration by mixing the compound having a desired degree of purity with physiologically acceptable carriers, excipients, stabilizers etc., and may be provided in sustained release or timed release formulations. Acceptable carriers or diluents for therapeutic use are well known in the pharmaceutical field, and are described, for example, in *Remington's Pharmaceutical Sciences*, Mack Publishing Co., (A. R. Gennaro edit. 1985). Such materials are nontoxic to the recipients at the dosages and concentrations employed, and include buffers such as phosphate, citrate, acetate and other organic acid salts, antioxidants such as ascorbic acid, low molecular weight (less than about ten residues) peptides such as polyarginine, proteins, such as serum albumin, gelatin, or immunoglobulins, hydrophilic polymers such as polyvinalpyrrolidinone, amino acids such as glycine, glutamic acid, aspartic acid, or arginine, monosaccharides, disaccharides, and other carbohydrates including cellulose or its derivatives, glucose, mannose or dextrins, chelating agents such as EDTA, sugar alcohols such as mannitol or sorbitol, counterions such as sodium and/or nonionic surfactants such as Tween, Pluronics or polyethyleneglycol.

Dosage formulations of the compounds of this invention to be used for therapeutic administration must be sterile. Sterility is readily accomplished by filtration through sterile membranes such as 0.2 micron membranes, or by other conventional methods. Formulations typically will be stored in lyophilized form or as an aqueous solution. The pH of the preparations of this invention typically will be between 3 and 11, more preferably from 5 to 9 and most preferably from 7 to 8. It will be understood that use of certain of the foregoing excipients, carriers, or stabilizers will result in the formation of cyclic polypeptide salts. While the preferred route of administration is by injection, other methods of administration are also anticipated such as intravenously (bolus and/or infusion), subcutaneously, intramuscularly, colonically, rectally, nasally or intraperitoneally, employing a variety of dosage forms such as suppositories, implanted pellets or small cylinders, aerosols, oral dosage formulations and topical formulations such as ointments, drops and dermal patches. The compounds of this invention are desirably incorporated into shaped articles such as implants which may employ inert materials such as biodegradable polymers or synthetic silicones, for example, Silastic, silicone rubber or other polymers commercially available.

The compounds of this invention may also be administered in the form of liposome delivery systems, such as small unilamellar vesicles, large unilamellar vesicles and multilamellar vesicles. Liposomes can be formed from a variety of lipids, such as cholesterol, stearylamine or phosphatidylcholines.

The compounds of this invention may also be delivered by the use of antibodies, antibody fragments, growth factors, hormones, or other targeting moieties, to which the compound molecules are coupled. The compounds of this invention may also be coupled with suitable polymers as targetable drug carriers. Such polymers can include polyvinylpyrrolidone, pyran copolymer, polyhydroxypropyl-methacrylamide-phenol, polyhydroxyethyl-aspartamide-phenol, or polyethyleneoxide-polylysine substituted with palmitoyl residues. Furthermore, the factor Xa inhibitors of this invention may be coupled to a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like.

Therapeutic compound liquid formulations generally are placed into a container having a sterile access port, for example, an intravenous solution bag or vial having a stopper pierceable by hypodermic injection needle.

Therapeutically effective dosages may be determined by either in vitro or in vivo methods. For each particular compound of the present invention, individual determinations may be made to determine the optimal dosage required. The range of therapeutically effective dosages will naturally be influenced by the route of administration, the therapeutic objectives, and the condition of the patient. For injection by hypodermic needle, it may be assumed the dosage is delivered into the body's fluids. For other routes of administration, the absorption efficiency must be individually determined for each inhibitor by methods well known in pharmacology. Accordingly, it may be necessary for the therapist to titer the dosage and modify the route of administration as required to obtain the optimal therapeutic effect. The determination of effective dosage levels, that is, the dosage levels necessary to achieve the desired result, will be within the ambient of one skilled in the art. Typically, applications of compound are commenced at lower dosage levels, with dosage levels being increased until the desired effect is achieved.

A typical dosage might range from about 0.001 mg/kg to about 1000 mg/kg, preferably from about 0.01 mg/kg to about 100 mg/kg, and more preferably from about 0.10 mg/kg to about 20 mg/kg. Advantageously, the compounds of this invention may be administered several times daily, and other dosage regimens may also be useful.

Typically, about 0.5 to 500 mg of a compound or mixture of compounds of this invention, as the free acid or base form or as a pharmaceutically acceptable salt, is compounded with a physiologically acceptable vehicle, carrier, excipient, binder, preservative, stabilizer, dye, flavor etc., as called for by accepted pharmaceutical practice. The amount of active ingredient in these compositions is such that a suitable dosage in the range indicated is obtained.

Typical adjuvants which may be incorporated into tablets, capsules and the like are a binder such as acacia, corn starch or gelatin, and excipient such as microcrystalline cellulose, a disintegrating agent like corn starch or alginic acid, a lubricant such as magnesium stearate, a sweetening agent such as sucrose or lactose, or a flavoring agent. When a dosage form is a capsule, in addition to the above materials it may also contain a liquid carrier such as water, saline, a fatty oil. Other materials of various types may be used as coatings or as modifiers of the physical form of the dosage unit. Sterile compositions for injection can be formulated according to conventional pharmaceutical practice. For example, dissolution or suspension of the active compound in a vehicle such as an oil or a synthetic fatty vehicle like ethyl oleate, or into a liposome may be desired. Buffers, preservatives, antioxidants and the like can be incorporated according to accepted pharmaceutical practice.

In practicing the methods of this invention, the compounds of this invention may be used alone or in combination, or in combination with other therapeutic or diagnostic agents. In certain preferred embodiments, the compounds of this inventions may be coadministered along with other compounds typically prescribed for these conditions according to generally accepted medical practice, such as anticoagulant agents, thrombolytic agents, or other antithrombotics, including platelet aggregation inhibitors, tissue plasminogen activators, urokinase, prourokinase, streptokinase, heparin, aspirin, or warfarin. The compounds of this invention can be utilized in vivo, ordinarily in mammals such as primates, such as humans, sheep, horses, cattle, pigs, dogs, cats, rats and mice, or in vitro.

The preferred compounds of the present invention are characterized by their ability to inhibit thrombus formation with acceptable effects on classical measures of coagulation parameters, platelets and platelet function, and acceptable levels of bleeding complications associated with their use. Conditions characterized by undesired thrombosis would include those involving the arterial and venous vasculature.

With respect to the coronary arterial vasculature, abnormal thrombus formation characterizes the rupture of an established atherosclerotic plaque which is the major cause of acute myocardial infarction and unstable angina, as well as also characterizing the occlusive coronary thrombus formation resulting from either thrombolytic therapy or percutaneous transluminal coronary angioplasty (PTCA).

With respect to the venous vasculature, abnormal thrombus formation characterizes the condition observed in patients undergoing major surgery in the lower extremities or the abdominal area who often suffer from thrombus formation in the venous vasculature resulting in reduced blood flow to the affected extremity and a predisposition to pulmonary embolism. Abnormal thrombus formation further characterizes disseminated intravascular coagulopathy commonly occurs within both vascular systems during septic shock, certain viral infections and cancer, a condition wherein there is rapid consumption of coagulation factors and systemic coagulation which results in the formation of life-threatening thrombi occurring throughout the microvasculature leading to widespread organ failure.

The compounds of this present invention, selected and used as disclosed herein, are believed to be useful for preventing or treating a condition characterized by undesired thrombosis, such as (a) the treatment or prevention of any thrombotically mediated acute coronary syndrome including myocardial infarction, unstable angina, refractory angina, occlusive coronary thrombus occurring post-thrombolytic therapy or post-coronary angioplasty, (b) the treatment or prevention of any thrombotically mediated cerebrovascular syndrome including embolic stroke, thrombotic stroke or transient ischemic attacks, (c) the treatment or prevention of any thrombotic syndrome occurring in the venous system including deep venous thrombosis or pulmonary embolus occurring either spontaneously or in the setting of malignancy, surgery or trauma, (d) the treatment or prevention of any coagulopathy including disseminated intravascular coagulation (including the setting of septic shock or other infection, surgery, pregnancy, trauma or malignancy and whether associated with multi-organ failure or not), thrombotic thrombocytopenic purpura, thromboangiitis obliterans, or thrombotic disease associated with heparin induced thrombocytopenia, (e) the treatment or prevention of thrombotic complications associated with extracorporeal circulation (e.g. renal dialysis, cardiopulmonary bypass or other oxygenation procedure, plasmapheresis), (f) the treatment or prevention of thrombotic complications associated with instrumentation (e.g. cardiac or other intravascular catheterization, intra-aortic balloon pump, coronary stent or cardiac valve), and (g) those involved with the fitting of prosthetic devices.

Anticoagulant therapy is also useful to prevent coagulation of stored whole blood and to prevent coagulation in other biological samples for testing or storage.

Thus the compounds of this invention can be added to or contacted with any medium containing or suspected to contain factor Xa and in which it is desired that blood coagulation be inhibited, e.g., when contacting the mammal's blood with material such as vascular grafts, stents, orthopedic prostheses, cardiac stents, valves and prostheses, extra corporeal circulation systems and the like.

Without further description, it is believed that one of ordinary skill in the art can, using the preceding description and the following illustrative examples, make and utilize the compounds of the present invention and practice the claimed methods. The following working examples therefore, specifically point out preferred embodiments of the present invention, and are not to be construed as limiting in any way the remainder of the disclosure.

EXAMPLES

Example 1

Preparation of (tert-Butoxy)-N-(2-{[(4-bromophenyl)sulfonyl]amino}ethyl)carboxamide

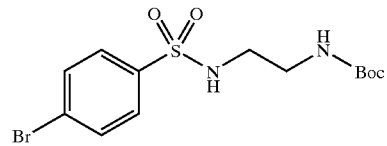

To a solution of N-(2-Aminoethyl)carbamic acid tert-butyl ester (1.86 g, 11.5 mmol) and triethyl amine (3 mL) in $CH_2Cl_2$ (100 mL) at 0° C., was added (4-bromophenyl)chlorosulfone (2.93 g, 11.5 mmol). The mixture was stirred for 3 hours, before the solvent was removed. The residue was dissolved in EtOAc (150 mL), washed with sat. $NaHCO_3$ (50 mL), sat. NaCl (50 mL), 1N HCl (50 mL), sat. NaCl (2×50 mL), dried over $MgSO_4$, and evaporated to give 3.8 g of the title compound as a white solid in 100% yield.

Example 2

Preparation of (tert-Butoxy)-N-[2-({[4-(2-{[(tert-butyl)amino]sulfonyl}phenyl)phenyl]sulfonyl}amino)ethyl]carboxamide

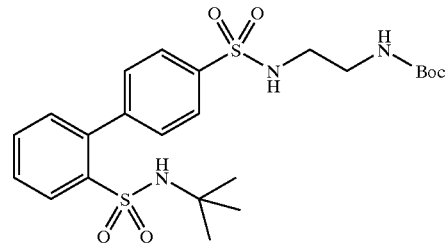

A mixture of the compound in example 1 (380 mg, 1.0 mmol), 2-{[(tert-butyl)amino]sulfonyl}phenyl boronic acid (308 mg, 1.2 mmol), triethyl amine (0.7 mL, 5.0 mmol), and $PdCl_2(dppf)$ (40 mg, 0.05 mmol) in DME (15 mL), was heated at 90° C. overnight. Upon completion of reaction, the mixture was filtered through a short plug of silica gel. The silica gel was washed with a mixture of EtOAc:Hexane (1:1), and the combined filtrate was evaporated to give 500 mg of the titled compound as a brown solid in 98% yield.

Example 3

Preparation of N-[2-({[4-(2-{[(tert-Butyl)amino]sulfonyl}phenyl)phenyl]sulfonyl}amino)ethyl](3-cyanophenyl)carboxamide

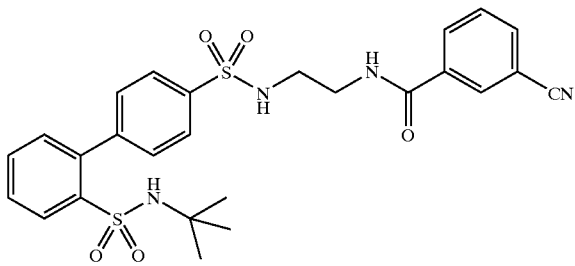

The compound in example 2 (100 mg, 0.18 mmol) was treated with 50% TFA in CH$_2$Cl$_2$ (2 mL) at 0° C. for 1 hour, before the solvent was removed by rotary evaporation. The residue, together with 3-cyanobenzoic acid (35 mg, 0.24 mmol), was dissolved in DMF (2 mL), neutralized with triethyl amine, before BOP (115 mg, 0.26 mmol) was added. The mixture was stirred at ambient temperature for two hour. Upon completion of reaction, the mixture was diluted with EtOAc (60 mL), washed with sat. NaHCO$_3$ (2×15 mL), sat. NaCl (2×15 mL), evaporated, and purified by HPLC to give 90 mg of the title compound.

Example 4

Preparation of 3-{N-[2-({[4-(2-Sulfamoylphenyl)phenyl]sulfonyl}amino)ethyl]carbamoyl}benzenecarboxamidine

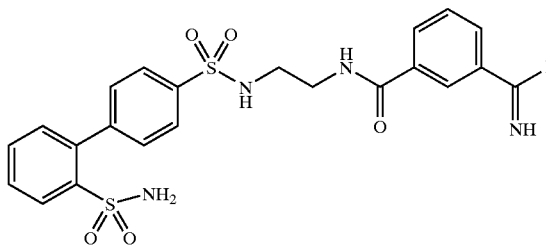

A mixture of the compound in example 3 (50 mg, 0.09 mmol), hydroxyamine hydrochloride (20 mg, 0.28 mmol), and triethyl amine (50 µL, 0.4 mmol) in EtOH (2 mL) was stirred at 45C overnight. The solvent was removed, and the residue was dissolved in AcOH (2 mL). To this solution, acetic anhydride was added, and the mixture was stirred at ambient temperature. After stirring for 30 min, 5 mg of 10% Pd/C was added, and the mixture was subjected to 1 atmospheric hydrogen gas for 1 hour. The catalyst was filtered and the solvent was evaporated. The residue was treated with TFA (1 mL) at 80° C. for 1 hour. After evaporation of TFA, the crude reaction mixture was purified by HPLC to give the title compound. ES-MS: (M+H)+=502.1.

Example 5

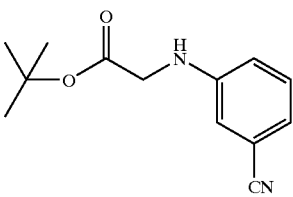

To a solution of t-butyl bromoacetate (6.1 mL, 37.5 mmol), 3-aminobenzonitrile (2.95 g, 25 mmol), potassium carbonate (10.4 g, 75 mmol) in CH$_3$CN (50 mL), was added KI (0.83 g, 5 mmol). The mixture was heated to reflux for 2 hrs. The mixture was cooled to room temperature and solvent was removed in vacuo. Ether and water were added to the mixture and organic layer was washed with 2N NaOH, brine, dried over NASO$_4$, filtered and the filtrated were concentrated in vacuo to give the title compound (5.7 g, 98.3%). ES-MS (M+H)+=233.1.

Example 6

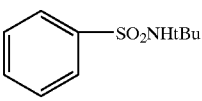

To a solution of tert-Butylamine (41.4 g, 566 mmol) and triethylamine (118 mL, 849 mmol) in DCM (1000 mL) in an ice bath, was added benzenesulfonyl chloride (100 g, 566 mmol) dropwise. The mixture was stirred at room temperature overnight. Water was added to the mixture and organic layer was washed with water, brine, dried over Na$_2$SO$_4$, filtered and filtrated evaporated in vacuo to give the title compound as light yellowish solid (117.63 g, 97.6%). ES-MS (M+H)+=214.1.

Example 7

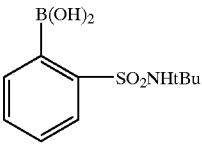

To a solution of compound of example 6 (53.25 g, 250 mmol) in THF (600 mL) in an ice bath, was added n-butyllithium in hexane (200 mL, 500 mmol) dropwise. A thick precipitate was formed when the reaction mixture was warmed up to 10° C. Triisopropylborate was added keeping the temperature below 35° C. After 1 hr., the mixture was cooled in an ice bath, 1N HCl (405 mL) was added, and the mixture was stirred overnight. The mixture was extracted with ether (100 mL) three times. The combined organic extracts were extracted with 1N NaOH (130 mL) three times. The aqueous extracts were acidified to pH 1 with 12 N HCl, and then extracted with ether three times (140 ML). The combined ether extracts were dried over MgSO$_4$, and solvents evaporated in vacuo. Hexane and ether were added and a white precipitate was formed. The solid was collected and washed with 10% ether/hexane to give the title compound. ES-MS (M+H)+=258.1.

Example 8

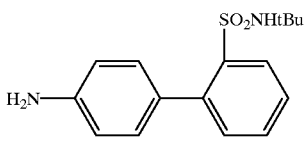

To a solution of compound of example 7 (6.4 g, 25 mmol) in toluene (120 mL) was added water (15 mL), 5N NaOH solution (38.5 mL), isopropanol (60 mL), 4-bromoaniline and tetrakis(triphenylphosphine)palladium(0). The mixture was refluxed for six hours, cooled to room temperature, diluted with EtOAc. The organic layer was washed with water, dried with $MgSO_4$, filtered and concentrated. This was purified by silica gel column chromatography using solvent system 30% EtOAc in hexane as eluent to give the title compound (5 g, 66%). ES-MS M+H=305.1.

Example 9

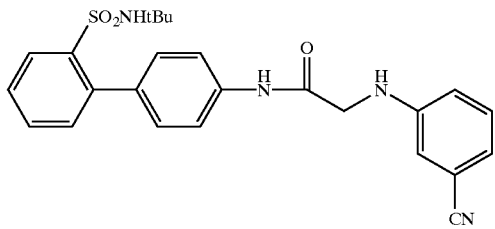

The compound of example 5 (0.75 mmol) was treated with 50% TFA in DCM (4 mL). The mixture was stirred at room temperature for 30 minutes and solvent evaporated to give a white solid. This was dissolved in DMF (2 mL) and cooled to 0° C. The solution was neutralized with DIEA (0.26 mL, 1.5 mmol) followed by the addition of compound of example 8 (108 mg, 0.35 mmol) and coupling reagent HATU (285 mg, 0.75 mmol). The solution was stirred at room temperature for 15 hours. The reaction mixture was diluted in a mixture of $EtOAc/H_2O$ (10 mL:5 mL). The organic layer was washed with sat. $NaHCO_3$ (2×10 mL), sat. NaCl (2×10 mL), dried over $MgSO_4$, filtered and solvent evaporated to give the crude product. This was purified by silica gel column chromatography using solvent system 50% EtOAc in hexane as eluent to give the title compound (60 mg, 37.2%). ES-MS (M+Na)+=485.1.

Example 10

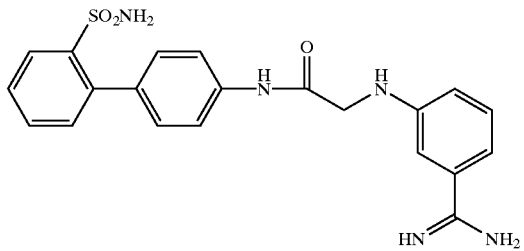

A solution of the compound of example 9 (60 mg, 0.13 mmol), hydroxylamine hydrochloride (18.1 mg, 0.26 mmol), TEA (54.3 μL, 0.39 mmol) in absolute ethanol (4 mL) was heated up to 60° C. and stirred for 15 hrs. The solution was cooled and solvent evaporated. The residue was dissolved in AcOH (2 mL). $Ac_2O$ (49 μL, 0.52 mmol) was added. The mixture was stirred at room temperature for 50 min. and the solvent evaporated. The residue was dissolved in MeOH (2–3 mL) and 10% Pd/C (catalytic amount) was added. The mixture was hydrogenated under balloon overnight, filtered through Celite to remove the catalyst and the filtrate was evaporated. TFA (2–3 mL) was added to the residue and the mixture was stirred at room temperature for 2–3 hrs. TFA was removed under reduced pressure to give the crude product. The obtained residue was purified by RP-HPLC to give the title compound as a white powder. ES-MS (M+H)+=424.1.

Example 11

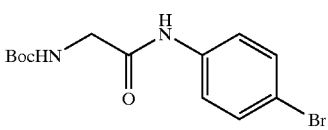

Boc-Gly-OH (1.75 g, 10 mmol) and 4-bromoaniline (1.89 g, 11 mmol) were dissolved in DMF (25 mL). DIEA (3.48 mL, 20 mmol) was added followed by the addition of the coupling reagent BOP (4.87 g, 11 mmol). The solution was stirred at room temperature for 12 hours. The reaction mixture was diluted in a mixture of $EtOAc/H_2O$ (100 mL:40 mL). The organic layer was washed with water, saturated $NaCO_3$, water, 1M $KHSO_4$, brine, dried over $MgSO_4$, filtered and solvent evaporated to give the title compound (1.123 g, 34%). ES-MS (M+Na)+=353.

Example 12

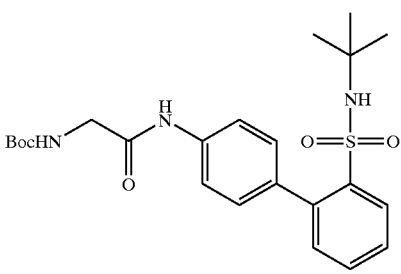

A mixture of compound of example 11 (328 mg, 1 mmol) and 2-(t-butylamino)sulfonyl-phenylboronic acid (262 mg, 1.02 mmol), tetrakis(triphenylphosphine)palladium(0) (58 mg, 0.05 mmol), tetrabutylammonium bromide (16 mg, 0.05 mmol), and potassium carbonate (147 mg, 2.13 mmol in 0.64 mL water) were refluxed with toluene (6 mL) under $N_2$ for 6 h. The toluene was removed in vacuo and the residue was dissolved in methylene chloride and water. The two phases were separated and organic phase was washed with water and brine, dried over $MgSO_4$ and concentrated to give the title compound (445 mg, 96.5%). (M+H)+=462.1.

Example 13

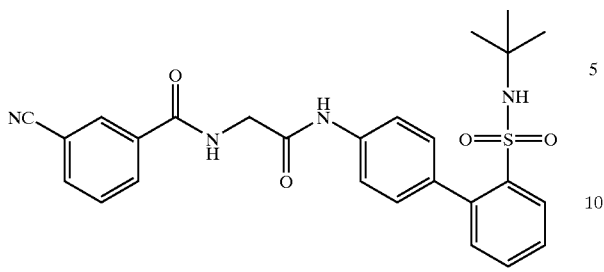

The compound of example 12 (386 mg, 0.84 mmol) was treated with 50% TFA in DCM (2 mL). The mixture was stirred at room temperature for 30 minutes then solvent evaporated to give a white solid. This was dissolved in DMF (5 mL) and cooled to 0° C. The solution was neutralized with DIEA (0.44 mL, 2.52 mmol) followed by addition of 3-cyano-benzoic acid (147 mg, 1 mmol) and coupling reagent BOP (442.5 mg, 1 mmol). The solution was stirred at room temperature for 15 hours. The reaction mixture was diluted in a mixture of EtOAc/H$_2$O (10 mL:5 mL). The organic layer was washed with sat. NaHCO$_3$ (2×20 mL), sat. NaCl (2×20 mL), dried over MgSO$_4$, filtered and solvent evaporated to give the crude product. This was purified by silica gel column chromatography using solvent system 50% EtOAc in hexane as eluent to give the title compound (148 mg, 30%). ES-MS (M+Na)+=513.

Example 14

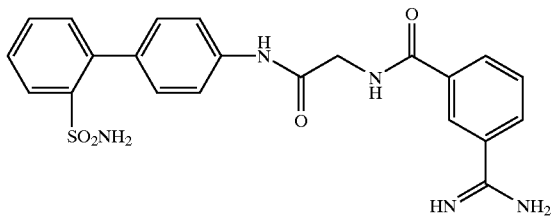

A solution of the compound of example 13 (61.3 mg, 0.125 mmol), hydroxylamine hydrochloride (17.4 mg, 0.25 mmol), TEA (52 μL, 0.375 mmol) in absolute ethanol (4 mL) was heated up to 60° C. and stirred for 15 hrs. The solution was cooled and solvent evaporated. The residue was dissolved in AcOH (2 mL). Ac$_2$O (47 μL, 0.5 mmol) was added. The mixture was stirred at room temperature for 50 min. and the solvent evaporated. The residue was dissolved in MeOH (2–3 mL) and 10% Pd/C (catalytic amount) was added. The mixture was hydrogenated under balloon overnight, filtered through Celite to remove the catalyst and the filtrate was evaporated. TFA (2–3 mL) was added to the residue and the mixture was stirred at room temperature for 2–3 hrs. TFA was removed under reduced pressure to give the crude product. The obtained residue was purified by RP-HPLC to give the title compound as a white powder. ES-MS (M+H)+=452.1.

Example 15

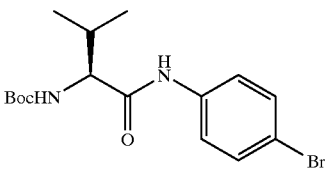

Boc-Val-OH (2.17 g, 10 mmol) and 4-bromoaniline (1.89 g, 11 mmol) were dissolved in DMF (25 mL). DIEA (3.48 mL, 20 mmol) was added followed by the addition of the coupling reagent BOP (4.87 g, 11 mmol). The solution was stirred at room temperature for 12 hours. The reaction mixture was diluted in a mixture of EtOAc/H$_2$O (100 mL:40 mL). The organic layer was washed with water, sat. NaCO$_3$, water, 1M KHSO$_4$, brine, dried over MgSO$_4$, filtered and solvent evaporated to give the title compound (3.53 g, 95.4%). ES-MS (M+H)+=371.

Example 16

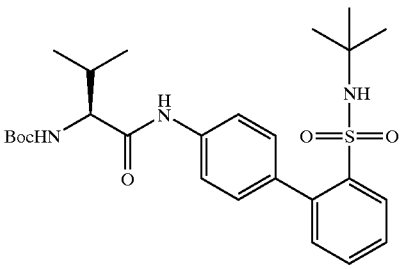

A mixture of compound of example 15 (740 mg, 2 mmol) and 2-(t-butylamino)sulfonyl-phenylboronic acid (616 mg, 2.4 mmol), tetrakis(triphenylphosphine)palladium(0) (115.5 mg, 0.1 mmol), tetrabutylammonium bromide (32.2 mg, 0.1 mmol), and potassium carbonate (691 mg, 5 mmol in 1.5 mL water) were refluxed with toluene (12 mL) under N$_2$ for 6 h. The toluene was removed in vacuo and the residue was dissolved in methylene chloride and water. The two phases were separated and organic phase was washed with water and brine, dried over MgSO$_4$ and concentrated to give the title compound (1.156 g, 100%). (M+H)+=504.1.

Example 17

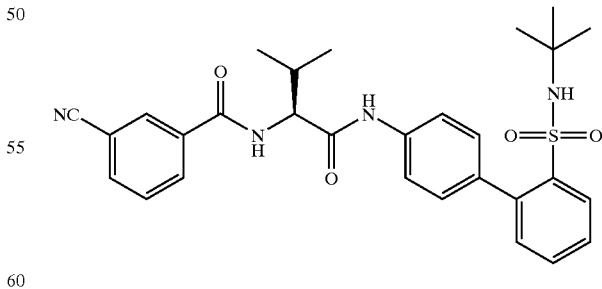

The compound of example 16 (0.7 mmol) was treated with 50% TFA in DCM (2 mL). The mixture was stirred at room temperature for 30 minutes then solvent evaporated to give a white solid. This was dissolved in DMF (2 mL) and cooled to 0° C. The solution was neutralized with DIEA (0.37 mL, 2.1 mmol) followed by addition of 3-cyanobenzoic acid (124 mg, 0.84 mmol) and coupling reagent BOP (371.7 mg, 0.84 mmol). The solution was stirred at room temperature for 15 hours. The reaction mixture was diluted in a mixture of EtOAc/H$_2$O (10 mL:5 mL). The organic layer was washed with sat. NaHCO$_3$ (2×20 mL), sat. NaCl (2×20 mL), dried over MgSO$_4$, filtered and solvent evaporated to give the crude product. This was purified by silica gel column chromatography using solvent system 40% EtOAc in hexane as eluent to give the title compound (204 mg, 55%). ES-MS (M+Na)+=555.2.

Example 18

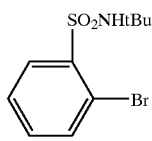

To a solution of 2-bromobenzenesulfonyl chloride (2.951 g, 0.0115 mol), t-butylamine (1.2 mL, 0.0138 mol), and triethylamine (3.2 mL, 0.023 mol) in CH$_2$Cl$_2$ (10 mL) was stirred at 0° C. under argon for 6 h. The reaction mixture was diluted with CH$_2$Cl$_2$ (100 mL) washed with saturated NaHCO$_3$, and saturated NaCl. The CH$_2$Cl$_2$ layer was dried over anhydrous MgSO$_4$, filtered and concentrated. The crude product was dried in vacuo to give 3.1 g of a white solid as the title compound (92.3%).

Example 19

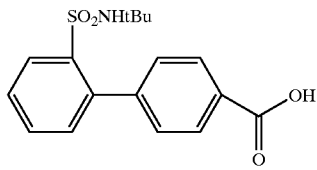

The mixture of the compound of Example 18 (4.995 g, 0.017 mol), 4-carboxyphenylboronic acid (7 g, 0.0427 mol), palladium acetate (0.095 g, 0.425 mmol), potassium carbonate (5.87 g, 0.0425 mol), and tetrabutylammonium bromide (5.48 g, 0.017 mol) was purged under argon for 5 min. Water (60 mL) was added. The reaction mixture was heated to 85° C. and stirred under argon for 1 day. The resulting mixture was cooled to room temperature, filtered through celite and extracted with EtOAc. The EtOAc layers were combined, dried over anhydrous MgSO$_4$, filtered and concentrated to give 9.93 g crude product as the titled compound in quantitative yield. The purity was satisfactory for the next step.

Example 20

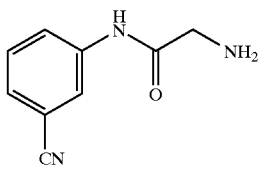

To a solution of 3-aminobenzonitrile (5 g, 0.042 mol) and Boc-gly-OH (7.4 g, 0.042 mol) in DMF (15 mL) was added DIEA (11 mL, 0.063 mol), followed by BOP (22.3 g, 0.05 mol). The reaction mixture was stirred at room temperature overnight, diluted with EtOAc (100 mL), washed with saturated NaHCO$_3$, and saturated NaCl. The EtOAc layer was dried over MgSO$_4$, filtered and concentrated to give a white solid compound in quantitative yield. This crude product was dissolved in CH$_2$Cl$_2$ (30 mL), followed by the addition of TFA (10 mL). The reaction mixture was stirred at room temperature overnight, concentrated to give the title compound as a white solid in quantitative yield (7.35 g). The purity was satisfactory for the next step.

Example 21

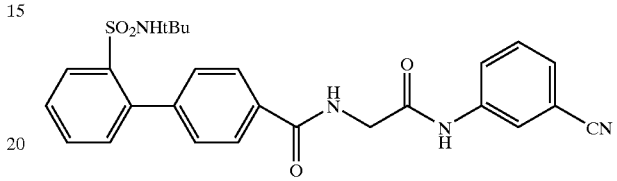

To a solution of the compound of Example 20 (800 mg, 4.57 mmol), and the compound of Example 19 (1.52 g, 4.57 mmol) in DMF (3 mL) was added DIEA (1.18 mL, 6,86 mmol), followed by BOP (2.42 g, 5.48 mmol). The reaction mixture was stirred at room temperature overnight, diluted with EtOAc (100 mL), washed with saturated NaHCO$_3$, and saturated NaCl. The EtOAc layer was dried over MgSO$_4$, filtered and concentrated to give the title compound as a white solid (2.12 g, 94.6%). ES-MS (M+H-tBu)+=435.0.

Example 22

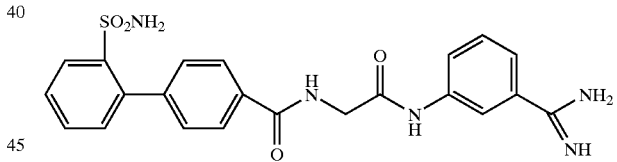

To the solution of the compound of example 21 (2.1 g, 4.3 mmol) in absolute EtOH (25 mL) was added hydroxylamine hydrochloride (0.598 g, 8.6 mmol) and triethyl amine (2 mL, 12.9 mmol). The reaction was stirred at 50° C. overnight, concentrated and purified via preparative HPLC to give the white solid hydroxyamidine compound. It was dissolved in acetic acid (10 mL), followed by the addition of acetic anhydride (0.5 mL). The reaction was completed in one hour and the product concentrated to dryness. The resulting solid was dissolved in anhydrous MeOH (4 mL). Palladium (10% Wt. On activated carbon, 20 mg) was added. The reaction mixture was stirred at room temperature under hydrogen (1 atm) for 4 hours, filtered through celite and concentrated to give a pale yellow residue. It was dissolved in TFA, stirred for 5 hours, concentrated and purified by preparative HPLC to give the title compound as a white solid (0.28 g, 15% overall yield). ES-MS (M+H)+=452.1.

Example 23

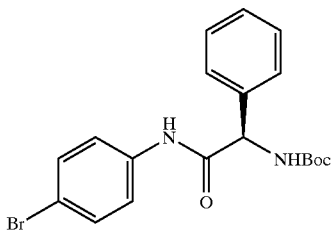

Boc-Phg-OH (1.19 g, 4.73 mmol) and 4-bromoaniline (0.895 g, 5.2 mmol) were dissolved in DMF (25 mL). DIEA (1.65 mL, 9.46 mmol) was added followed by the addition of the coupling reagent BOP (2.3 g, 5.2 mmol). The solution was stirred at room temperature for 12 hours. The reaction mixture was diluted in a mixture of EtOAc/$H_2O$ (100 mL:40 mL). The organic layer was washed with water, sat. $Na_2CO_3$, water, 1M $KHSO_4$, brine, dried over $MgSO_4$, filtered and solvent evaporated to give the title compound. ES-MS (M+H)+=405.

Example 24

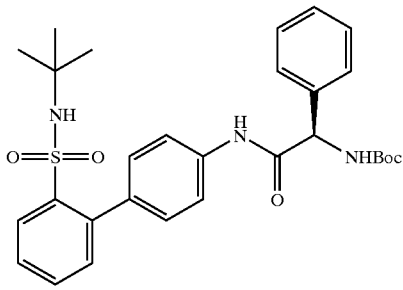

A mixture of compound of example 23 (472 mg, 1.17 mmol) and 2-(t-butylamino)sulfonyl-phenylboronic acid (359.5 mg, 1.4 mmol), tetrakis(triphenylphosphine)palladium(0) (67.6 mg, 0.0585 mmol), tetrabutylammonium bromide (18.9 mg, 0.0585 mmol), and potassium carbonate (404 mg, 2.93 mmol in 0.88 mL water) were refluxed with toluene (6 mL) under $N_2$ for 6 hrs. The toluene was removed in vacuo and the residue was dissolved in methylene chloride and water. The two phases were separated and organic phase was washed with water and brine, dried over $MgSO_4$ and concentrated to give the title compound (435 mg, 69.2%). (M+H)+=538.1.

Example 25

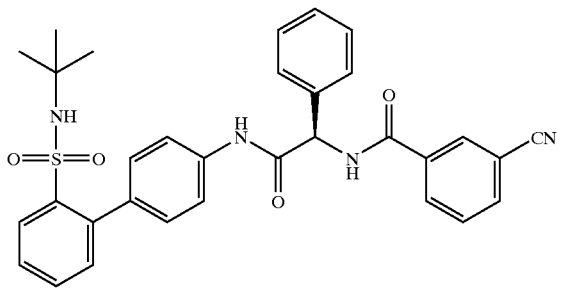

The compound of example 24 (362 mg, 0.67 mmol) was treated with 50% TFA in DCM (2 mL). The mixture was stirred at room temperature for 30 minutes then solvent evaporated to give a white solid. This was dissolved in DMF (5 mL) and cooled to 0° C. The solution was neutralized with DIEA (0.35 mL, 2.02 mmol) followed by addition of 3-CN-benzoic acid (119 mg, 0.81 mmol) and coupling reagent BOP (358 mg, 0.81 mmol). The solution was stirred at room temperature for 15 hours. The reaction mixture was diluted in a mixture of EtOAc/$H_2O$ (10 mL:5 mL). The organic layer was washed with sat. $NaHCO_3$ (2×20 mL), sat. NaCl (2×20 mL), dried over $MgSO_4$, filtered and solvent evaporated to give the crude product. This was purified by silica gel column chromatography using solvent system 40% EtOAc in hexane as eluent to give the title compound (137 mg, 36%). ES-MS (M+Na)+=589.

Example 26

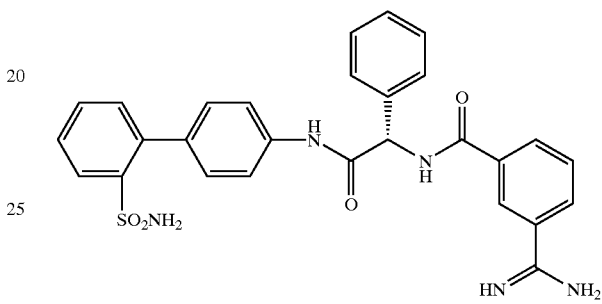

A solution of the compound of example 25 (36.9 mg, 0.065 mmol), hydroxylamine hydrochloride (9 mg, 0.13 mmol), TEA (27 µL, 0.20 mmol) in absolute ethanol (4 mL) was heated up to 60° C. and stirred at room temperature for 15 hrs. The solution was cooled and solvent evaporated. The residue was dissolved in AcOH (2 mL). $Ac_2O$ (24.5 µL, 0.26 mmol) was added. The mixture was stirred at room temperature for 50 min. and the solvent evaporated. The residue was dissolved in MeOH (2–3 mL) and 10% Pd/C (catalytic amount) was added. The mixture was hydrogenated under balloon overnight, filtered through Celite to remove the catalyst and the filtrate was evaporated. TFA (2–3 mL) was added to the residue and the mixture was stirred at room temperature for 2–3 hrs. TFA was removed under reduced pressure to give the crude product. The obtained residue was purified by RP-HPLC to give the title compound as a white powder. ES-MS (M+H)+=528.1.

Example 27

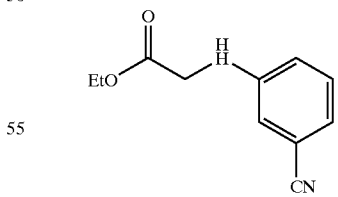

To a solution of ethyl bromoacetate (10.6 g, 60 mmol), 3-aminobenzonitrile (5 g, 40 mmol), and potassium carbonate (17.5 g, 120 mmol) in acetonitrile (30 ml) was added potassium iodide (1.4 g, 8 mmol). The mixture was heated to reflux for 6 hrs. The mixture was cooled to room temperature, and solvent was removed in vacuo. Ether and water were added to the mixture. Organic layer was washed with 1N hydrochloride and brine, and dried over magnesium

Example 28

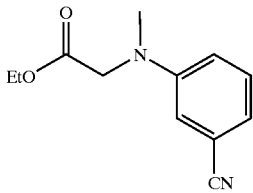

To a solution of the compound of example 27 (200 mg, 1 mmol) and cesium carbonate (650 mg, 2 mmol) in dimethylformamide (5 ml) was added iodomethane (75 ul, 1.2 mmol). The mixture was stirred at 90° C. for 2 hrs. After the filtration of the solid, the filtrate was concentrated in vacuo, and the residue was purified by silica gel column chromatography using solvent system 15% ethyl acetate in hexane as eluent to give the title compound as an oil (270 mg, 100%). ES-MS (M+H)+=219.

Example 29

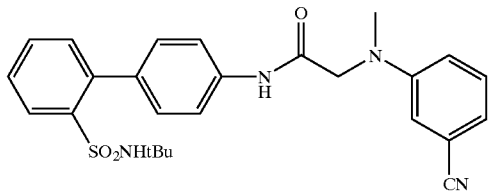

To a solution of the compound of example 19 (126 mg, 0.41 mmol) in dichloromethane (5 ml) was added 2.0M trimethylaluminum in hexane (0.62 ml, 1.24 mmol). The mixture was stirred at room temperature for 30 minutes, methane gas evolved. A solution of the compound of example 28 (90 mg, 0.41 mmol) in dichlodomethiane (1 ml) was added. The mixture was stirred at room temperature overnight. 1N hydrochloride was added to acidify the solution to pH=2. After the addition of water and dichloromethane, the organic layer was separated and the aqueous layer was extracted with dichloromethane. The combined organic extracts were dried over magnesium sulfate, and concentrated in vacuo. The crude residue was purified by silica gel column chromatography using solvent system 30% ethyl acetate in hexane as eluent to give the title compound as a solid (70 mg, 36%). ES-MS (M+H)+=477.

Example 30

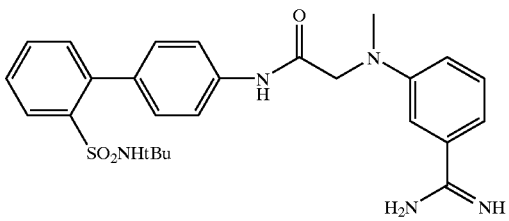

A solution of the compound of example 29 (70 mg, 0.15 mmol), hydroxylamine hydrochloride (26 mg, 0.37 mmol) and triethylamine (52 ul, 0.37 mmol) in absolute ethanol (3 ml) was stirred at 40° C. for 15 hrs. After the evaporation of the solvent in vacuo, the residue was dissolved in acetic acid (3 ml), and acetic anhydride (28 ul, 0.3 mmol) was added. The mixture was stirred at room temperature for 3 hrs. It was diluted with absolute methanol (5 ml), and 10% Pd/C (catalytic amount) was added. The mixture was applied with 50 psi hydrogen for 6 hrs. After the filtration through Celite to remove the catalyst, the filtrate was concentrated in vacuo. The crude residue was purified by RP-HPLC to give the title compound as a white powder. ES-MS (M+H)+=494.

Example 31

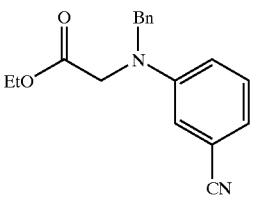

To a solution of the compound of example 27 (200 mg, 1 mmol) and cesium. carbonate (650 mg, 2 mmol) in dimethylformamide (5 ml) was added benzyl bromide (180 ul, 1.5 mmol). The mixture was stirred at 90° C. for 2 hrs. After the filtration of the solid, the filtrate was concentrated in vacuo and the residue was purified by silica gel column chromatography using solvent system 10% ethyl acetate in hexane as eluent to give the title compound as an oil (210 mg, 71%). ES-MS (M+H)+=295.

Example 32

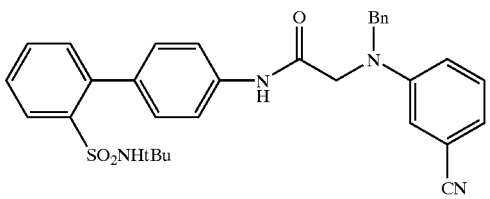

To a solution of the compound of example 19 (126 mg, 0.41 mmol) in dichloromethane (5 ml) was added 2.0M trimethylaluminum in hexane (0.62 ml, 1.24 mmol). The mixture was stirred at room temperature for 30 minutes, methane gas evolved. A solution of the compound of example 31 (120 mg, 0.41 mmol) in dichlodomethane (1 ml) was added. The mixture was stirred at room temperature overnight. 1N hydrochloride was added to acidify the solution to pH=2. After the addition of water and dichloromethane, the organic layer was separated, and the aqueous layer was extracted with dichloromethane. The combined organic extracts were dried over magnesium sulfate, and concentrated in vacuo. The crude residue was purified by silica gel column chromatography using solvent system 20% ethyl acetate in hexane as eluent to give the title compound as a solid (172 mg, 76%). ES-MS (M+H)+=553.

Example 33

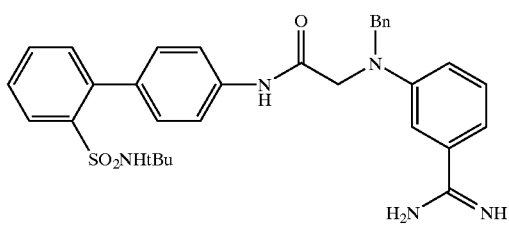

To a solution of the compound of example 32 (100 mg, 0.18 mmol) and absolute methanol (73 ul, 1.8 mmol) in ethyl acetate (3 ml) in an ice bath was saturated with hydrochloride gas for 10 minutes. The mixture was stirred at room temperature for 3 hrs. After the evaporation of the solvent in vacuo, the residue was dissolved in absolute methanol (3 ml), and ammonia acetate (83 mg, 1.08 mmol) was added. The mixture was refluxed for 3 hrs. The solvent was evaporated in vacuo. The crude residue was purified by RP-HPLC to give the title compound as white powder. ES-MS (M+H)+=514.

Example 34

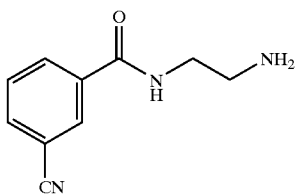

To a solution of t-Butyl N-(aminoethyl)-carbamate (250 mg, 1.56 mmol), and 4-cyanobenzoyl chloride (258 mg, 1.56 mmol) in CH$_2$Cl$_2$ was added triethylanine (0.685 mL, 4.68 mmol). The reaction mixture was stirred at room temperature overnight. Concentration under reduced pressure gave a white solid. To the suspension of this solid compound in CH$_2$Cl$_2$ (10 mL) was added trifloroacetic acid (5 mL), the reaction was completed after 4 hours at room temperature. The title compound was obtained in quantitative yield as a white solid after removal of the solvent and excess TFA.

Example 35

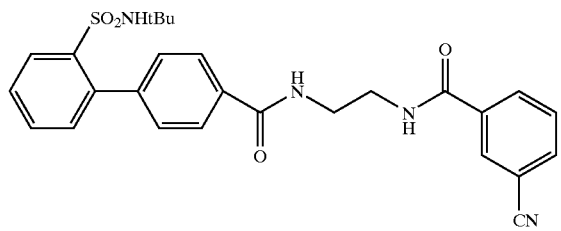

To a solution of the compound of example 19 (518.5 mg, 1.56 mmol) and the compound of example 34 (295 mg, 1.56 mmol) in DMF (5 mL) was added DIEA (0.4 mL, 2.34 mmol), followed by BOP (828 mg, 1.87 mmol). The reaction mixture was stirred at room temperature under argon overnight. The reaction mixture was diluted with EtOAc (100 mL), washed with saturated NaHCO$_3$, and saturated NaCl. The EtOAc layer was dried over anhydrous MgSO$_4$, filtered and concentrated to give the crude title compound in quantitative yield.

Example 36

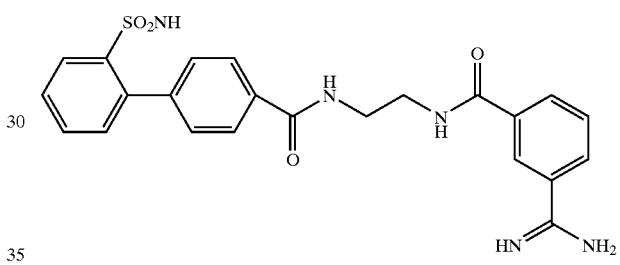

The solution of the compound of example 35 (1.24 g, theoretical 1.56 mmol) in anhydrous MeOH (10 mL) was bubbled in HCl gas for 10 minutes at 0° C. The reaction flask as capped and stirred at room temperature overnight. The mixture was concentrated to dryness. To the resulting residue in anhydrous MeOH (5 mL) was added ammonium acetate 1.2 g, 15.6 mmol). The reaction mixture was heated at refluxing temperature for 5 hours, concentrated and purified via preparative HPLC to give the title compound as a white solid (96.4%). ES-MS (M+H)+=466.1.

Example 37

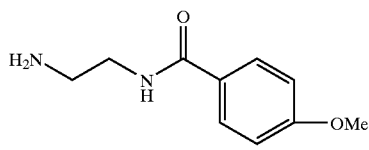

To a solution of t-Butyl N-(aminoethyl)-carbamate (277 mg, 1.73 mmol), and 4-methoxybenzoic acid (263 mg, 1.73 mmol) in DMF (3 mL) was added DIEA (0.452 mL, 2.6 mmol). The reaction mixture was stirred at room temperature overnight, diluted with EtOAc (100 mL), washed with saturated NaHCO$_3$, and saturated NaCl. The EtOAc layer was dried over anhydrous MgSO$_4$, filtered and concentrated to give a white solid. To the solution of this solid compound in CH$_2$Cl$_2$ (10 mL) was added TFA (10 mL). The reaction was complete after stirring at room temperature overnight.

The title compound was obtained in quantitative yield (100%) after removal of the solvent and excess TFA.

Example 38

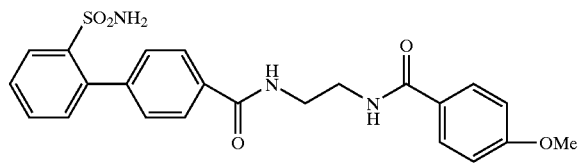

The solution of the compound of example 19 (1.86 g, 0.56 mmol) and the compound of example 37 (0.11 g, 0.56 mmol) in DMF (5 mL) was added DIEA (0.15 mL, 0.84 mmol), followed by BOP (0.3 g, 0.67 mmol). The reaction solution was diluted with EtOAc (100 mL), washed with saturated NaHCO$_3$, and saturated NaCl. The EtOAc layer was dried over anhydrous MgSO$_4$, filtered, concentrated and purified via preparative HPLC to give a white solid. It was dissolved in TFA (2 mL). The resulting was stirred at room temperature overnight, concentrated and purified via preparative HPLC to give 59.6 mg of the title compound as a white solid (24%). ES-MS (M+H)+=454.1.

BIOLOGICAL ACTIVITY EXAMPLES

Evaluation of the compounds of this invention is guided by in vitro protease activity assays (see below) and in vivo studies to evaluate antithrombotic efficacy, and effects on hemostasis and hematological parameters.

The compounds of the present invention are dissolved in buffer to give solutions containing concentrations such that assay concentrations range from 0 to 100 $\mu$M. In the assays for thrombin, prothrombinase and factor Xa, a synthetic chromogenic substrate is added to a solution containing test compound and the enzyme of interest and the residual catalytic activity of that enzyme is determined spectrophotometrically. The IC$_{50}$ of a compound is determined from thesubstrate turnover. The IC$_{50}$ is the concentration of test compound giving 50% inhibition of the substrate turnover. The compounds of the present invention desirably have an IC$_{50}$ of less than 500 nM in the factor Xa assay, preferably less than 200 nM, and more preferred compounds have an IC$_{50}$ of about 100 nM or less in the factor Xa assay. The compounds of the present invention desirably have an IC$_{50}$ of less than 4.0 $\mu$M in the prothrombinase assay, preferably less than 200 nM, and more preferred compounds have an IC$_{50}$ of about 10 nM or less in the prothrombinase assay. The compounds of the present invention desirably have an IC$_{50}$ of greater than 1.0 $\mu$M in the thrombin assay, preferably greater than 10.0 $\mu$M, and more preferred compounds have an IC$_{50}$ of greater than 100.0 $\mu$M in the thrombin assay.

Amidolytic Assays for Determining Protease Inhibition Activity

The factor Xa and thrombin assays are performed at room temperature, in 0.02 M Tris.HCl buffer, pH 7.5, containing 0.15 M NaCl. The rates of hydrolysis of the para-nitroanilide substrate S-2765 (Chromogenix) for factor Xa, and the Isubstrate Chromozym TH (Boehringer Mannheim) for thrombin following preincubation of the enzyme with inhibitor for 5 minutes at room temperature, and were determined using the Softmax 96-well plate reader (Molecular Devices), monitored at 405 nm to measure the time dependent appearance of p-nitroaniline.

The prothrombinase inhibition assay is performed in a plasma free system with modifications to the method described by Sinha, U. et al., Thromb. Res., 75, 427–436 (1994). Specifically, the activity of the prothrombinase complex is determined by measuring the time course of thrombin generation using the p-nitroanilide substrate Chromozym TH. The assay consists of preincubatidn (5 minutes) of selected compounds to be tested as inhibitors with the complex formed from factor Xa (0.5 nM), factor Va (2 nM), phosphatidyl serine:phosphatidyl choline (25:75, 20 $\mu$M) in 20 mM Tris.HCl buffer, pH 7.5, containing 0.15 M NaCl, 5 mM CaCl$_2$ and 0.1% bovine serum albumin. Aliquots from the complex-inhibitor mixture are added to prothrombin (1 nM) and Chromozym TH (0.1 mM). The rate of substrate cleavage is monitored at 405 nm for two minutes. Eight different concentrations of inhibitor are assayed in duplicate. A standard curve of thrombin generation by an equivalent amount of untreated complex are used for determination of percent inhibition.

Antithrombotic Efficacy in a Rabbit Model of Venous Thrombosis

A rabbit deep vein thrombosis model as described by Hollenbach, S. et al., Thromb. Haemost. 71, 357–362 (1994), is used to determine the in-vivo antithrombotic activity of the test compounds. Rabbits are anesthetized with I.M. injections of Ketamine, Xylazine, and Acepromazine cocktail. A standardized protocol consists of insertion of a thrombogenic cotton thread and copper wire apparatus into the abdominal vena cava of the anesthetized rabbit. A non-occlusive thrombus is allowed to develop in the central venous circulation and inhibition of thrombus growth is used as a measure of the antithrombotic activity of the studied compounds. Test agents or control saline are administered through a marginal ear vein catheter. A femoral vein catheter is used for blood sampling prior to and during steady state infusion of test compound. Initiation of thrombus formation begins immediately after advancement of the cotton thread apparatus into the central venous circulation. Test compounds are administered from time=30 min to time=150 min at which the experiment is terminated. The rabbits are euthanized and the thrombus excised by surgical dissection and characterized by weight and histology. Blood samples are analyzed for changes in hematological and coagulation parameters.

Effects of Compounds in Rabbit Venous Thrombosis Model

Administration of compounds in the rabbit venous thrombosis model demonstrates antithrombotic efficacy at the higher doses evaluated. There are no significant effects of the compound on the aPTT and PT prolongation with the highest dose (100 $\mu$g/kg+2.57 $\mu$g/kg/min). Compounds have no significant effects on hematological parameters as compared to saline controls. All measurements are an average of all samples after steady state administration of vehicle or (D)-Arg-Gly-Arg-thiazole. Values are expressed as mean±SD.

Without further description, it is believed that one of ordinary skill in the art can, using the preceding description and the following illustrative examples, make and utilize the compounds of the present invention and practice the claimed methods.

What is claimed is:
1. A compound according to the formula I:

A—Y—D—E—G—J—Z—L wherein:
A is selected from the group consisting of:
  (a) phenyl, which is independently substituted with 0–2 $R^1$ substituents; and
  (b) naphthyl, which is independently substituted with 0–2 $R^1$ substituents;
each $R^1$ is independently selected from the group consisting of:
  Halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN, —$NO_2$, $(CH_2)_m NR^2 R^3$, $SO_2 NR^2 R^3$, $SO_2 R^2$, $CF_3$, $OR^2$, and a 5–6 membered aromatic heterocyclic system containing from 1–4 heteroatoms selected from the group consisting of N, O and S, wherein from 1–4 hydrogen atoms on the aromatic heterocyclic system may be independently replaced with a member selected from the group consisting of halo, $C_1$-$C_4$-alkyl, —CN, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl and —$NO_2$;
$R^2$ and $R^3$ are independently selected from the group consisting of:
  H, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, $C_{0-4}$alkylphenyl and $C_{0-4}$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN, and —$NO_2$;
m is an integer of 0–2;
Y is a direct link;
D is a member selected from the group consisting of:
  (a) phenyl, which is independently substituted with 0–2 $R^{1a}$ substituents; and
  (b) naphthyl, which is independently substituted with 0–2 $R^{1a}$ substituents;
each $R^{1a}$ is independently selected from the group consisting of:
  Halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN, —$NO_2$, $(CH_2)_m NR^{2a} R^{3a}$, $SO_2 NR^{2a} R^{3a}$, $SO_2 R^{2a}$, $CF_3$, $OR^{2a}$, and a 5–6 membered aromatic heterocyclic system containing from 1–4 heteroatoms selected from the group consisting of N, O and S, wherein from 1–4 hydrogen atoms on the aromatic heterocyclic system may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN and —$NO_2$;
$R^{2a}$ and $R^{1a}$ are independently selected from the group consisting of:
  H, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, $C_{0-4}$alkylphenyl and $C_{0-4}$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN and —$NO_2$;
E is —$N(R^5)$—$C(=O)$—;
$R^5$ is selected from the group consisting of:
  H, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, $C_{0-4}$alkylphenyl, $C_{0-4}$alkylnaphthyl, $C_{0-4}$alkylheteroaryl, $C_{1-4}$alkylCOOH and $C_{1-4}$alkylCOO$C_{1-4}$alkyl, wherein from 1–4 hydrogen atoms on the ring atoms of the phenyl, naphthyl and heteroaryl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN and —$NO_2$;
G is —$CR^7 R^8$—
wherein $R^7$ and $R^8$ are independently a member selected from the group consisting of:
  hydrogen, $C_{1-4}$alkyl, $C_{2-6}$alkenyl, $C_{2-6}$alkynyl, $C_{3-8}$cycloalkyl, $C_{0-4}$alkyl-$C_{3-8}$cycloalkyl, $C_{0-4}$alkylphenyl, $C_{0-4}$alkylnaphthyl, —$C_{0-4}$alkylCOO$R^9$, —$C_{0-4}$alkylC$(=O)NR^9 R^{10}$, —$C_{0-4}$alkylC$(=O)NR^9$—$CH_2$—$CH_2$—O—$R^{10}$, —$C_{0-4}$alkylC$(=O)NR^9$(—$CH_2$—$CH_2$—O—$R^{10}$—$)_2$, —$N(R^9)COR^{10}$, —$N(R^9)C(=O)R^{10}$, —$N(R^9)SO_2 R^{10}$, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl-$C_{3-8}$cycloalkyl, —CN and —$NO_2$;
$R^9$ and $R^{10}$ are independently selected from the group consisting of:
  H, $C_{1-4}$alkyl, $C_{0-4}$alkylphenyl and $C_{0-4}$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl-$C_{3-8}$cycloalkyl, —CN and —$NO_2$, and wherein $R^9$ and $R^{10}$ taken together can form a 5–8 membered heterocylic ring;
J is a member selected from the group consisting of:
  —$C(=O)$—$N(R^{11})$—$(CH_2)_{0-2}$, —$N(R^{11})$—$(CH_2)_{0-2}$—$C(=O)$—, and —$N(R^{11})$—$(CH_2)_{0-2}$;
$R^{11}$ is a member selected from the group consisting of:
  hydrogen, $C_{1-4}$alkyl, $C_{2-6}$alkenyl, $C_{2-6}$alkynyl, $C_{3-8}$cycloalkyl, $C_{0-4}$alkyl-$C_{3-8}$cycloalkyl, $C_{0-4}$alkylphenyl, $C_{0-4}$alkylnaphthyl, $C_{0-4}$alkylheterocyclic ring having from 1 to 4 hetero ring atoms selected from the group consisting of N, O and S, $CH_2 COOC_{1-4}$alkyl, $CH_2 COOC_{1-4}$alkylphenyl and $CH_2 COOC_{1-4}$alkylnaphthyl;
Z is a member selected from the group consisting of:
  (a) phenyl, which is independently substituted with 0–2 $R^{1b}$ substituents; and
  (b) naphthyl, which is independently substituted with 0–2 $R^{1b}$ substituents;
each $R^{1b}$ is independently selected from the group consisting of:
  Halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —$NO_2$, $NR^{2b} R^{3b}$, $SO_2 NR^{2b} R^{3b}$, $SO_2 R^{2b}$, $CF_3$, $OR^{2b}$, —O—$CH_2$Ph, O—$CH_2$—OPh, O—$CH_2$—$CH_2$—$OR^{2b}$, O—$CH_2$—COO$R^{2b}$, $N(R^{2b})$—$CH_2$—$CH_2$—$OR^{2b}$, $N(—CH_2$—$CH_2$—$OR^{2b})_2$, $N(R^{2b})$—$C(=O)R^{3b}$, $N(R^{2b})SO_2$—$R^{3b}$, and a 5–6 membered aromatic heterocyclic system containing from 1–4 heteroatoms selected from the group consisting of N, O and S, wherein from 1–4 hydrogen atoms on the aromatic heterocyclic system may be independently replaced with a member selected from the group consisting of halo, $C_{1-4}$alkyl, $C_{2-4}$alkenyl, $C_{2-6}$alkynyl, $C_{3-8}$cycloalkyl, $C_{0-4}$alkyl$C_{3-8}$cycloalkyl, —CN and —NO$_2$;

$R^{2b}$ and $R^{3b}$ are independently selected from the group consisting of:

H, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, $C_{0-4}$alkylphenyl and $C_{0-4}$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN and —NO$_2$;

L is $C(=NR^{12})NR^{12}R^{13}$;

each $R^{12}$ and $R^{13}$ are independently selected from the group consisting of:

hydrogen, —OR$^{14}$, —NR$^{14}$R$^{15}$, $C_{1-4}$alkyl, $C_{0-4}$alkylphenyl, $C_{0-4}$alkylnaphthyl, COOC$_{1-4}$alkyl, COO—$C_{0-4}$alkylphenyl and COO—$C_{0-4}$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN, and —NO$_2$;

$R^{14}$ and $R^{15}$ are independently selected from the group consisting of:

H, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, $C_{0-4}$alkylphenyl and $C_{0-4}$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN, and —NO$_2$;

or all pharmaceutically acceptable salts or prodrug derivatives thereof.

2. A compound of claim 1 wherein:

A is selected from the group consisting of:
(a) phenyl, which is independently substituted with 0–2 $R^1$ substituents; and
(b) naphthyl, which is independently substituted with 0–2 $R^1$ substituents; each $R^1$ is independently selected from the group consisting of:

halo, $C_{1-4}$alkyl, —CN, $(CH_2)_m NR^2R^3$, SO$_2$NR$^2$R$^3$, SO$_2$R$^2$, CF$_3$, OR$^2$, and a 5–6 membered aromatic heterocyclic system containing from 1–4 heteroatoms selected from the group consisting of N, O and S;

$R^2$ and $R^3$ are independently selected from the group consisting of:
H, $C_{1-4}$alkyl, $C_{0-4}$alkylphenyl and $C_{0-4}$alkylnaphthyl;

m is an integer of 0–2;

Y is a direct link;

D is a member selected from the group consisting of:
(a) phenyl, which is independently substituted with 0–2 $R^{1a}$ substituents; and
(b) naphthy, which is independently substituted with 0–2 $R^{1a}$ substituents;

each $R^{13}$ is independently selected from the group consisting of:
Halo, $C_{1-4}$alkyl, —CN, —NO$_2$, $(CH_2)_m NR^{2a}R^{3a}$, SO$_2$NR$^{2a}$R$^{3a}$, SO$_2$R$^{2a}$, CF$_3$, OR$^{2a}$, and a 5–6 membered aromatic heterocyclic ring containing from 1–4 heteroatoms selected from the group consisting of N, O and S;

$R^{2a}$ and $R^{3a}$ are independently selected from the group consisting of:
H, $C_{1-4}$alkyl, $C_{0-4}$alkylphenyl and $C_{0-4}$alkylnaphthyl;

E is —N(R$^5$)—C(=O)—;

$R^5$ is selected from the group consisting of:
H, $C_{1-4}$alkyl, $C_{0-4}$alkylphenyl, $C_{0-4}$alkylnaphthyl, $C_{0-4}$alkylheteroaryl, $C_{1-4}$alkylCOOH and $C_{1-4}$alkylCOOC$_{1-4}$alkyl;

G is —CR$^7$R$^8$— wherein $R^7$ and $R^8$ are independently a member selected from the group consisting of:
hydrogen, $C_{1-4}$alkyl, $C_{0-4}$alkyl-$C_{3-8}$cycloalkyl, $C_{0-4}$alkylphenyl, $C_{0-4}$alkylnaphthyl, —$C_{0-4}$alkylCOOR$^9$, —$C_{0-4}$alkylC(=O)NR$^9$R$^{10}$, —N(R$^9$)COR$^{10}$, —N(R$^9$)C(=O)R$^{10}$ and —N(R$^9$)SO$_2$R$^{10}$;

$R^9$ and $R^{10}$ are independently selected from the group consisting of:
H, $C_{1-4}$alkyl, $C_{0-4}$alkylphenyl and $C_{0-4}$alkylnaphthyl;

J is a member selected from the group consisting of:
—C(=O)—N(R$^{11}$)—(CH$_2$)$_{0-2}$, —N(R$^{11}$)—(CH$_2$)$_{0-2}$—C(=O)—, and —N(R$^{11}$)—(CH$_2$)$_{0-2}$;

$R^{11}$ is a member selected from the group consisting of:
hydrogen, $C_{1-4}$alkyl, $C_{2-6}$alkenyl, $C_{2-6}$alkynyl, $C_{3-8}$cycloalkyl, $C_{0-4}$alkylphenyl, $C_{0-4}$alkylnaphthyl, $C_{0-4}$alkylheterocyclics, CH$_2$COOC$_{1-4}$alkyl, CH$_2$COOC$_{1-4}$alkylphenyl and CH$_2$COOC$_{1-4}$alkylnaphthyl;

Z is a member selected from the group consisting of:
(a) phenyl, which is independently substituted with 0–2 $R^{1b}$ substituents; and
(b) naphthyl, which is independently substituted with 0–2 $R^{1b}$ substituents;

each $R^{1b}$ is independently selected from the group consisting of:
halo, $C_{1-4}$alkyl, —CN, —NO$_2$, NR$^{2b}$R$^{3b}$, SO$_2$N$^{2b}$R$^{3b}$, SO$_2^{2b}$, CF$_3$, OR$^{2b}$, —O—CH$_2$—CH$_2$—OR$^{2b}$, O—CH$_2$—COOR$^{2b}$, N(R$^{2b}$)—CH$_2$—CH$_2$—OR$^{2b}$, N(—CH$_2$—CH$_2$—OR$^{2b}$)$_2$, N(R$^{2b}$)—C(=O)R$^{3b}$, N(R$^{2b}$)SO$_2$—R$^{3b}$, and a 5–6 membered aromatic heterocyclic ring containing from 1–4 heteroatoms selected from the group consisting of N, O and S;

$R^{2b}$ and $R^{3b}$ are independently selected from the group consisting of
H, $C_{1-4}$alkyl, $C_{0-4}$alkylphenyl and $C_{0-4}$alkylnaphthyl;

L is $C(=NR^{12})NR^{12}R^{13}$;

each $R^{12}$ and $R^{13}$ are independently selected from the group consisting of:
hydrogen, —OR$^{14}$, —NR$^{14}$R$^{15}$, $C_{1-4}$alkyl, $C_{0-4}$alkylphenyl, $C_{0-4}$alkylnaphthyl, COOC$_{1-4}$alkyl, COO—$C_{0-4}$alkylphenyl and COO—$C_{0-4}$alkylnaphthyl; and $R^{14}$ and $R^{15}$ are independently selected from the group consisting of:
H and $C_{1-4}$alkyl.

3. A compound of claim 1, wherein:

A is phenyl, which is independently substituted with 0–2 $R^1$ substituents;

each $R^1$ is independently selected from the group consisting of:
halo, $(CH_2)_m NR^2R^3$, SO$_2$NR$^2$R$^3$ and SO$_2$R$^2$;

$R^2$ and $R^3$ are independently selected from the group consisting of:
H and $C_{1-4}$alkyl;

Y is a direct link;

D is a phenyl, which is independently substituted with 0–2 $R^{1a}$ substituents;

each $R^{1a}$ is independently selected from the group consisting of:
Halo and $C_{1-4}$alkyl;

E is —N($R^5$)—C(=O)—;

$R^5$ is selected from the group consisting of:
H, $C_{1-4}$alkyl, $C_{0-4}$alkylphenyl, $C_{0-4}$alkylnaphthyl and $C_{0-4}$alkylheteroaryl;

G is —C$R^7R^8$— wherein $R^7$ and $R^8$ are independently a member selected from the group consisting of:
hydrogen, $C_{1-4}$alkyl, $C_{0-4}$alkyl-$C_{3-8}$cycloalkyl, $C_{0-4}$alkylphenyl, $C_{0-4}$alkylnaphthyl, —$C_{0-4}$alkylCOO$R^9$, —$C_{0-4}$alkylC(=O)N$R^9R^{10}$, —$C_{0-4}$alkylC(=O)N$R^9$—CH$_2$—CH$_2$—O—$R^{10}$, —$C_{0-4}$alkylC(=O)N$R^9$(—CH$_2$—CH$_2$—O—$R^{10}$—)$_2$, —N($R^9$)CO$R^{10}$, —N($R^9$)C(=O)$R^{10}$, —N($R^9$)SO$_2R^{10}$;

$R^9$ and $R^{10}$ are independently selected from the group consisting of:
H and $C_{1-4}$alkyl, wherein the N$R^9R^{10}$ group of $R^7$ and $R^8$ is optionally cyclized to form a 5–8 membered heterocyclic group;

J is a member selected from the group consisting of:
—C(=O)—N($R^{11}$)—(CH$_2$)$_{0-2}$, —N($R^{11}$)—(CH$_2$)$_{0-2}$—C(=O)—, and —N($R^{11}$)—(CH$_2$)$_{0-2}$;

$R^{11}$ is a member selected from the group consisting of:
hydrogen, $C_{1-4}$alkyl, $C_{2-6}$alkenyl, $C_{0-4}$alkylphenyl, $C_{0-4}$alkylnaphthyl and a $C_{0-4}$alkylheterocyclic ring;

Z is a phenyl, which is independently substituted with 0–2 $R^{1b}$ substituents;

each $R^{1b}$ is independently selected from the group consisting of:
halo, $C_{1-4}$alkyl, OH, OBn, O—CH$_2$—CH$_2$—OH, O—CH$_2$—CH$_2$—OCH$_3$, O—CH$_2$—COOH, O—CH$_2$—C(=O)—O—CH$_3$, NH$_2$, NH—CH$_2$—CH$_2$—O—CH$_3$, NH—C(=O)—O—CH$_3$, and NH—SO$_2$—CH$_3$;

L is C(=N$R^{12}$)N$R^{12}R^{13}$; and each $R^{12}$ and $R^{13}$ are independently selected from the group consisting of:
hydrogen and $C_{1-4}$alkyl.

4. A compound of claim 1, wherein

A is a member selected from the group consisting of:

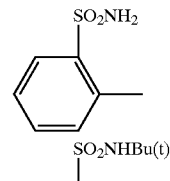

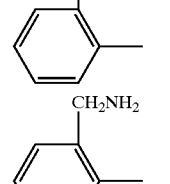

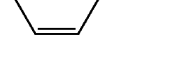

;

D is a member selected from the group consisting of:

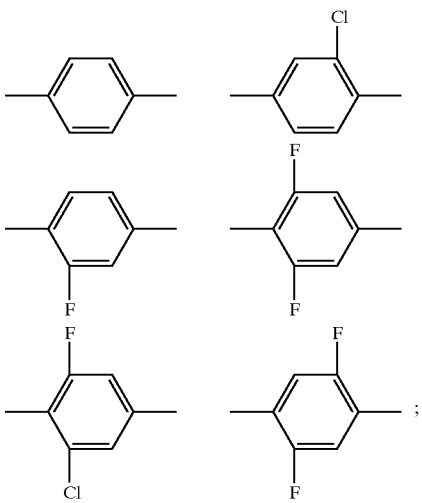

E is —NH—C(=O);

G is selected from the group consisting of:
—CH—(C(=O)—O$R^8$)— and —CH(—$R^7$)—;

$R^7$ is a member selected from the group consisting of:
H, phenyl, Bn, and cyclohexyl;

$R^8$ is a member selected from the group consisting of:
H, $C_{1-4}$alkyl, and $C_{3-6}$cycloalkyl;

J is a member selected from the group consisting of;
—C(=O)—N($R^{11}$)—(CH$_2$)$_{0-2}$, —N($R^{11}$)—(CH$_2$)$_{0-2}$—C(=O)—, and —N($R^{11}$)—(CH$_2$)$_{0-2}$;

$R^{11}$ is a member selected from the group consisting of:
H, methyl, phenyl and benzyl;

Z is a member selected from the group consisting of:

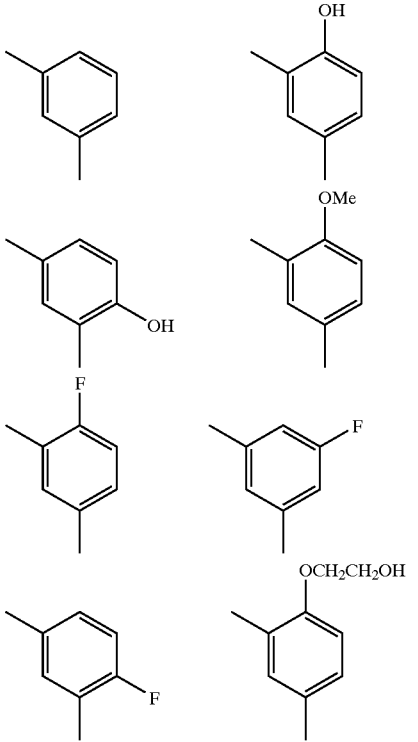

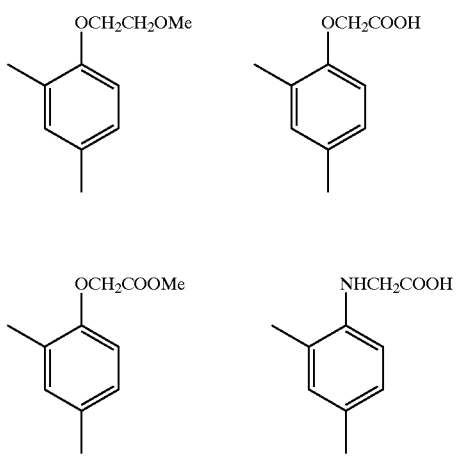
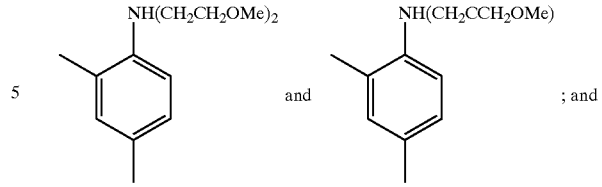

L is C(=NH)—NH$_2$.

5. A pharmaceutical composition for treating a condition in a mammal characterized by undesired thrombosis comprising a pharmaceutically acceptable carrier and a compound of claim 1.

6. A pharmaceutical composition for treating a condition in a mammal characterized by undesired thrombosis comprising a pharmaceutically acceptable carrier and a compound of claim 2.

* * * * *

UNITED STATES PATENT AND TRADEMARK OFFICE
CERTIFICATE OF CORRECTION

PATENT NO. : 6,545,055 B1
DATED : April 8, 2003
INVENTOR(S) : Zhu et al.

It is certified that error appears in the above-identified patent and that said Letters Patent is hereby corrected as shown below:

<u>Column 133,</u>
Line 54, replace "$R^{1a}$" with -- $R^{3a}$ --;

<u>Column 135,</u>
Line 61, replace "$R^{13}$" with -- $R^{1a}$ --;

<u>Column 136,</u>
Line 1, replace "$R_{2a}$" with -- $R^{2a}$ --; and
Line 15, replace "$-C_{0-4}alkylC(=O)NR^9R^9R^{10}$" with -- $-C_{0-4}alkylC(=O)NR^9R^{10}$ --.

Signed and Sealed this

Thirtieth Day of September, 2003

JAMES E. ROGAN
*Director of the United States Patent and Trademark Office*